(12) United States Patent
Lundquist et al.

(10) Patent No.: US 10,570,450 B2
(45) Date of Patent: Feb. 25, 2020

(54) INTEGRATED ILLUMINATION OF OPTICAL ANALYTICAL DEVICES

(71) Applicant: Pacific Biosciences of California, Inc., Menlo Park, CA (US)

(72) Inventors: Paul Lundquist, San Francisco, CA (US); Stephen Turner, Seattle, WA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 16/208,421

(22) Filed: Dec. 3, 2018

(65) Prior Publication Data

US 2019/0256911 A1 Aug. 22, 2019

Related U.S. Application Data

(63) Continuation of application No. 15/489,655, filed on Apr. 17, 2017, now Pat. No. 10,144,963, which is a
(Continued)

(51) Int. Cl.
*C12Q 1/6874* (2018.01)
*G01N 21/64* (2006.01)
(Continued)

(52) U.S. Cl.
CPC ......... *C12Q 1/6874* (2013.01); *G01N 21/648* (2013.01); *G01N 21/6428* (2013.01);
(Continued)

(58) Field of Classification Search
CPC ............... C12Q 1/6874; G02B 6/0229; G02B 2006/12147; G01N 21/7746;
(Continued)

(56) References Cited

U.S. PATENT DOCUMENTS

| 5,082,629 A | 1/1992 | Burgess et al. |
| 5,094,517 A | 3/1992 | Franke |

(Continued)

FOREIGN PATENT DOCUMENTS

| EP | 1105529 B1 | 11/2005 |
| EP | 1871902 B1 | 10/2006 |

(Continued)

OTHER PUBLICATIONS

Yariv, A. et al. (1977) IEEE J Quantum Elec QE-13(4):233-253.
(Continued)

*Primary Examiner* — Dennis White
(74) *Attorney, Agent, or Firm* — VLP Law Group LLP

(57) ABSTRACT

Optical analytical devices and their methods of use are provided. The devices are useful in the analysis of highly multiplexed optical reactions in large numbers at high densities, including biochemical reactions, such as nucleic acid sequencing reactions. The devices include integrated illumination elements and optical waveguides for illumination of the optical reactions. The devices further provide for the efficient coupling of optical excitation energy from the waveguides to the optical reactions. Optical signals emitted from the reactions can thus be measured with high sensitivity and discrimination using features such as spectra, amplitude, and time resolution, or combinations thereof. The devices of the invention are well suited for miniaturization and high throughput.

22 Claims, 33 Drawing Sheets

Related U.S. Application Data continuation of application No. 14/187,198, filed on Feb. 21, 2014, now Pat. No. 9,624,540.

(60) Provisional application No. 61/768,053, filed on Feb. 22, 2013.

(51) Int. Cl.
  *G01N 21/77* (2006.01)
  *G02B 6/02* (2006.01)
  *G02B 6/12* (2006.01)

(52) U.S. Cl.
  CPC ..... *G01N 21/6454* (2013.01); *G01N 21/7746* (2013.01); *G02B 6/0229* (2013.01); *G01N 2021/7789* (2013.01); *G01N 2201/08* (2013.01); *G02B 2006/12147* (2013.01)

(58) Field of Classification Search
  CPC ............. G01N 21/648; G01N 21/6428; G01N 21/6454; G01N 2201/08; G01N 2021/7789
  See application file for complete search history.

(56) References Cited

U.S. PATENT DOCUMENTS

| | | |
|---|---|---|
| 5,135,876 A | 8/1992 | Andrade et al. |
| 5,157,262 A | 10/1992 | Marsoner et al. |
| 5,159,661 A | 10/1992 | Ovshinsky et al. |
| 5,173,747 A | 12/1992 | Boiarski et al. |
| 5,192,502 A | 3/1993 | Attridge et al. |
| 5,233,673 A | 8/1993 | Vali et al. |
| 5,239,178 A | 8/1993 | Derndinger et al. |
| 5,439,647 A | 8/1995 | Saini |
| 5,446,534 A | 8/1995 | Goldman |
| 5,470,710 A | 11/1995 | Weiss et al. |
| 5,545,531 A | 8/1996 | Rava et al. |
| 5,578,832 A | 11/1996 | Trulson et al. |
| 5,605,662 A | 2/1997 | Heller et al. |
| 5,631,734 A | 5/1997 | Stern et al. |
| 5,677,196 A | 10/1997 | Herron et al. |
| 5,695,934 A | 12/1997 | Brenner |
| 5,744,305 A | 4/1998 | Fodor et al. |
| 5,821,058 A | 5/1998 | Smith et al. |
| 5,812,709 A | 9/1998 | Arai et al. |
| 5,832,165 A | 11/1998 | Reichert et al. |
| 5,835,458 A | 11/1998 | Bischel et al. |
| 5,867,266 A | 2/1999 | Craighead |
| 5,919,712 A | 7/1999 | Herron et al. |
| 6,071,748 A | 6/2000 | Modlin et al. |
| 6,192,168 B1 | 2/2001 | Feldstein et al. |
| 6,210,896 B1 | 4/2001 | Chan |
| 6,236,945 B1 | 5/2001 | Simpson et al. |
| 6,263,286 B1 | 7/2001 | Gilmanshin et al. |
| 6,285,020 B1 | 9/2001 | Kim et al. |
| 6,325,977 B1 | 12/2001 | Theil |
| 6,388,788 B1 | 5/2002 | Harris et al. |
| 6,437,345 B1 | 8/2002 | Bruno-Raimondi et al. |
| 6,438,279 B1 | 8/2002 | Craighead et al. |
| 6,603,537 B1 | 8/2003 | Dietz et al. |
| 6,611,634 B2 | 8/2003 | Herron et al. |
| 6,690,002 B2 | 2/2004 | Kuroda et al. |
| 6,699,655 B2 | 3/2004 | Nikiforov |
| 6,784,982 B1 | 8/2004 | Blumenfeld et al. |
| 6,800,860 B2 | 10/2004 | Dietz et al. |
| 6,818,395 B1 | 11/2004 | Quake et al. |
| 6,867,851 B2 | 3/2005 | Blumenfeld et al. |
| 6,917,726 B2 | 7/2005 | Levene et al. |
| 6,919,211 B1 | 7/2005 | Fodor et al. |
| 6,979,830 B2 | 12/2005 | Dietz et al. |
| 6,982,146 B1 | 1/2006 | Schneider et al. |
| 7,012,687 B2 | 3/2006 | Blumberg et al. |
| 7,022,515 B2 | 4/2006 | Herron et al. |
| 7,056,661 B2 | 6/2006 | Korlach et al. |
| 7,057,832 B2 | 6/2006 | Wu et al. |
| 7,075,695 B2 | 7/2006 | Gronbach |
| 7,081,954 B2 | 7/2006 | Sandstrom |
| 7,083,914 B2 | 8/2006 | Seul et al. |
| 7,130,041 B2 | 10/2006 | Bouzid et al. |
| 7,135,667 B2 | 11/2006 | Oldham et al. |
| 7,139,074 B2 | 11/2006 | Reel |
| 7,145,645 B2 | 12/2006 | Blumenfeld et al. |
| 7,150,997 B2 | 12/2006 | Kovacs |
| 7,170,050 B2 | 1/2007 | Turner et al. |
| 7,175,811 B2 | 2/2007 | Bach et al. |
| 7,181,122 B1 | 2/2007 | Levene et al. |
| 7,189,361 B2 | 3/2007 | Carson et al. |
| 7,197,196 B2 | 3/2007 | Lin et al. |
| 7,199,357 B1 | 4/2007 | Oldham et al. |
| 7,209,836 B1 | 4/2007 | Schermer et al. |
| 7,227,128 B2 | 6/2007 | Sagatelyan |
| RE39,772 E | 8/2007 | Herron et al. |
| 7,257,141 B2 | 8/2007 | Chua |
| 7,302,348 B2 | 11/2007 | Ghosh et al. |
| 7,315,019 B2 | 1/2008 | Turner et al. |
| 7,323,681 B1 | 1/2008 | Oldham et al. |
| 7,400,380 B2 | 7/2008 | Hahn |
| 7,537,734 B2 | 5/2009 | Reichert et al. |
| 7,709,808 B2 | 5/2010 | Reel et al. |
| 7,767,441 B2 | 8/2010 | Chiou et al. |
| 7,811,810 B2 | 10/2010 | Chiou et al. |
| 7,817,281 B2 | 10/2010 | Kiesel et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 7,907,800 B2 | 3/2011 | Foquet et al. |
| 7,935,310 B2 | 5/2011 | Korlach |
| 8,053,742 B2 | 11/2011 | Lundquist et al. |
| 8,149,657 B2 | 4/2012 | Huang et al. |
| 8,207,509 B2 | 6/2012 | Lundquist et al. |
| 8,247,216 B2 | 8/2012 | Zaccarin et al. |
| 8,274,040 B2 | 9/2012 | Zhong et al. |
| 8,465,699 B2 | 6/2013 | Fehr et al. |
| 8,467,061 B2 | 6/2013 | McCaffrey et al. |
| 8,471,219 B2 | 6/2013 | Lundquist et al. |
| 8,471,230 B2 | 6/2013 | Zhong et al. |
| 8,618,507 B1 | 12/2013 | Lundquist et al. |
| 8,906,320 B1 | 12/2014 | Eltoukhy et al. |
| 9,029,802 B2 | 5/2015 | Lundquist et al. |
| 9,372,308 B1 | 6/2016 | Saxena et al. |
| 9,658,161 B2 | 5/2017 | Saxena et al. |
| 2002/0034457 A1 | 3/2002 | Reichert et al. |
| 2002/0110839 A1 | 8/2002 | Bach et al. |
| 2002/0113213 A1 | 8/2002 | Amirkhanian et al. |
| 2002/0146047 A1 | 10/2002 | Bendett et al. |
| 2003/0044781 A1 | 3/2003 | Korlach et al. |
| 2003/0132406 A1 | 7/2003 | Waldhausl et al. |
| 2003/0138180 A1 | 7/2003 | Kondo et al. |
| 2003/0174324 A1 | 9/2003 | Sandstrom |
| 2003/0174992 A1 | 9/2003 | Levene et al. |
| 2004/0040868 A1 | 3/2004 | Denuzzio et al. |
| 2004/0046128 A1 | 3/2004 | Abel et al. |
| 2004/0197793 A1 | 10/2004 | Hassibi et al. |
| 2004/0249227 A1 | 12/2004 | Klapproth et al. |
| 2005/0014178 A1 | 1/2005 | Holm-Kennedy |
| 2005/0135974 A1 | 6/2005 | Harvey et al. |
| 2005/0175273 A1 | 8/2005 | Iida et al. |
| 2005/0201899 A1 | 9/2005 | Weisbuch |
| 2005/0206895 A1 | 9/2005 | Salmelainen |
| 2006/0060766 A1 | 3/2006 | Turner et al. |
| 2006/0103850 A1 | 5/2006 | Alphonse et al. |
| 2007/0036511 A1 | 2/2007 | Lundquist et al. |
| 2007/0099212 A1 | 5/2007 | Harris |
| 2007/0146701 A1 | 6/2007 | Kiesel et al. |
| 2007/0188746 A1 | 8/2007 | Kraus et al. |
| 2007/0196815 A1 | 8/2007 | Lappe et al. |
| 2008/0002929 A1 | 1/2008 | Bowers et al. |
| 2008/0020938 A1 | 1/2008 | Kaplan |
| 2008/0039339 A1 | 2/2008 | Hassibi et al. |
| 2008/0056950 A1 | 3/2008 | Weisbuch et al. |
| 2008/0128627 A1 | 6/2008 | Lundquist et al. |
| 2008/0161195 A1 | 7/2008 | Turner et al. |
| 2008/0212960 A1 | 9/2008 | Lundquist et al. |

(56) References Cited

U.S. PATENT DOCUMENTS

| | | |
|---|---|---|
| 2009/0146076 A1 | 6/2009 | Chiou et al. |
| 2009/0247414 A1 | 10/2009 | Obradovic et al. |
| 2009/0311774 A1 | 12/2009 | Chiou et al. |
| 2010/0065726 A1 | 3/2010 | Zhong et al. |
| 2010/0121582 A1 | 5/2010 | Pan et al. |
| 2010/0163521 A1 | 7/2010 | Balamane et al. |
| 2010/0255488 A1 | 10/2010 | Kong et al. |
| 2010/0256918 A1 | 10/2010 | Chen et al. |
| 2011/0117637 A1 | 5/2011 | Gray et al. |
| 2011/0210094 A1 | 9/2011 | Gray et al. |
| 2011/0223590 A1 | 9/2011 | Chiou et al. |
| 2011/0306039 A1 | 12/2011 | Chiou et al. |
| 2011/0306143 A1 | 12/2011 | Chiou et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0058469 A1 | 3/2012 | Shen |
| 2012/0085894 A1 | 4/2012 | Zhong et al. |
| 2012/0156100 A1 | 6/2012 | Tsai et al. |

FOREIGN PATENT DOCUMENTS

| | | |
|---|---|---|
| EP | 2362209 A2 | 8/2011 |
| KR | 1020050088782 A | 9/2005 |
| WO | 1991006678 A1 | 5/1991 |
| WO | 2001016375 A2 | 3/2001 |
| WO | 2004100068 A2 | 11/2004 |
| WO | 2006116726 A2 | 2/2006 |
| WO | 2006135782 A2 | 12/2006 |
| WO | 2007002367 A2 | 1/2007 |
| WO | 2007011549 A1 | 1/2007 |
| WO | 2008002765 A2 | 1/2008 |
| WO | 2009056065 A1 | 5/2009 |
| WO | 2009131535 A1 | 10/2009 |
| WO | 2009149125 A2 | 12/2009 |
| WO | 2010051773 A1 | 5/2010 |
| WO | 2010102567 A1 | 9/2010 |
| WO | 2011076132 A2 | 6/2011 |
| WO | 2014031157 A1 | 2/2014 |

OTHER PUBLICATIONS

Boiarski et al. (1992) Proc. SPIE 1793:199-211.
Mortazavi et al. (1994) Optics Letters 19:1290.
Fink, Y. et al. (1998) Science 282:1679-1682.
Budach et al. (1999) Anal. Chem. 71(16):3347-3355.
Feldstein et al. (1999) J. Biomed Microdev. 1:139-153.
Weissman et al. (1999) Proc. SPIE 3596:210-216.
Deopura, M. et al. (2001) Optics Lett 26(15):1197-1199.
Cottier et al. (2002) Proc. SPIE 4616:53-63.
Duveneck et al. (2002) Anal Chem Acta 469:49-61.
Herron et al. (2003) Biopolymers at Interfaces 2nd Ed. Surfactant Science Series vol. 110, Marcel Dekker, NY pp. 115-163.
Levene, M.J. et al. (2003) Science 299:682-686.
Salama et al. (2004) Biosensors & Bioelectronics 19:1377-1386.
Bernini et al. (2005) Proc. SPIE 5728:101-111.
Feng et al. (2006) IEEE J. Quantum Electron. 42:885.
Psaltis et al. (2006) Nature 442:381.
Wu et al. (2006) Biosensors and Bioelectronics 21:1252-1263.
Barrios et al. (2007) Optics Letters 32:3080.
Feng et al. (2007) Optics Letters 32:2131.
Sun et al. (2007) Optics Express 15:17967.
Barrios et al. (2008) Optics Letters 33:708.
Robinson et al. (2008) Optics Express 16:4296.
Eid et al. (2009) Science 323:133.
Nava et al. (2010) Electronics Letters 46:1686.
Abbas et al. (2011) Sens. Actuators B Chem. 156:169-175.
Pan et al. (2011) Optics Communications 284:429.
Sahin et al. (2011) J. Nanophoton. 5:051812.
Chen et al. (2012) Optics Letters 37:2814.
Laurell et al. (2012) Optics Express 20:22308.
Song et al. (2012) Optics Express 20:22290.
Yao et al. (2012) Nonlinear Optics and Solid-State Lasers, Springer-Verlag Berlin Heidelberg, Chapter 5.
Barrios (2006) IEEE Photon Technol. Lett. 18:2419.
Jun. 30, 2016 Extended European Search Report in counterpart EP 14 754 479.5.

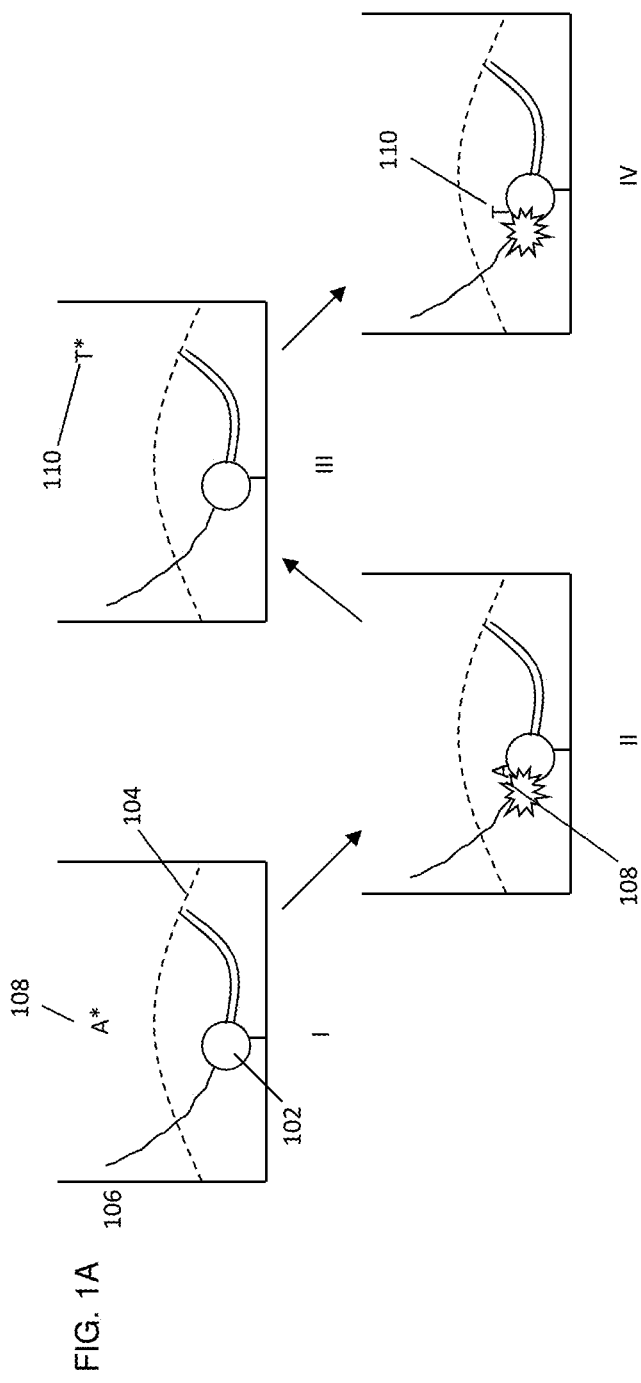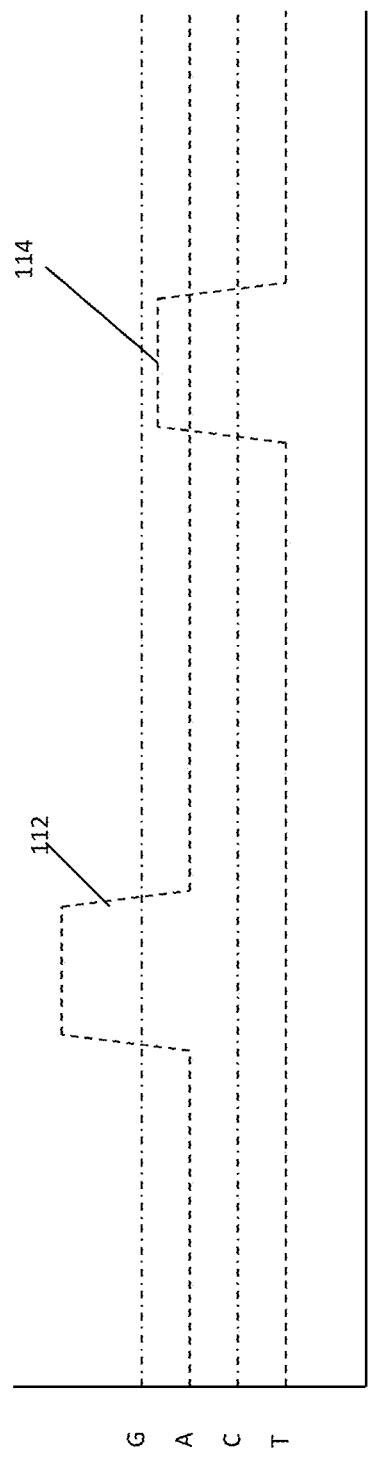
FIG. 1A
FIG. 1B

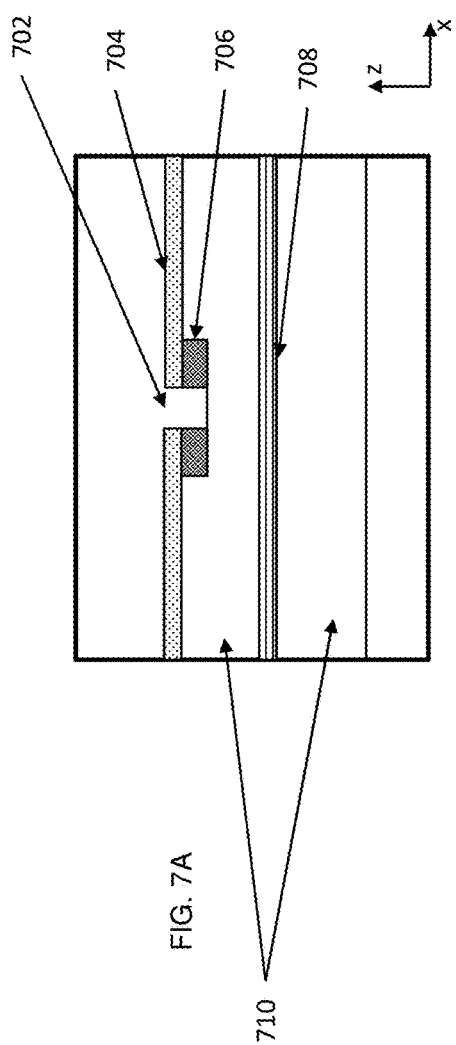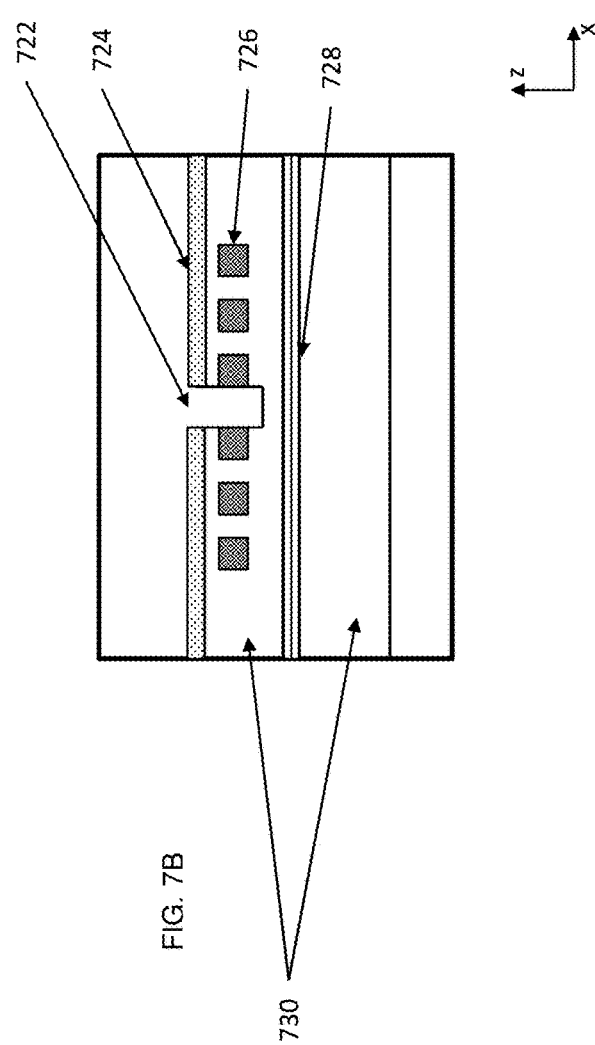

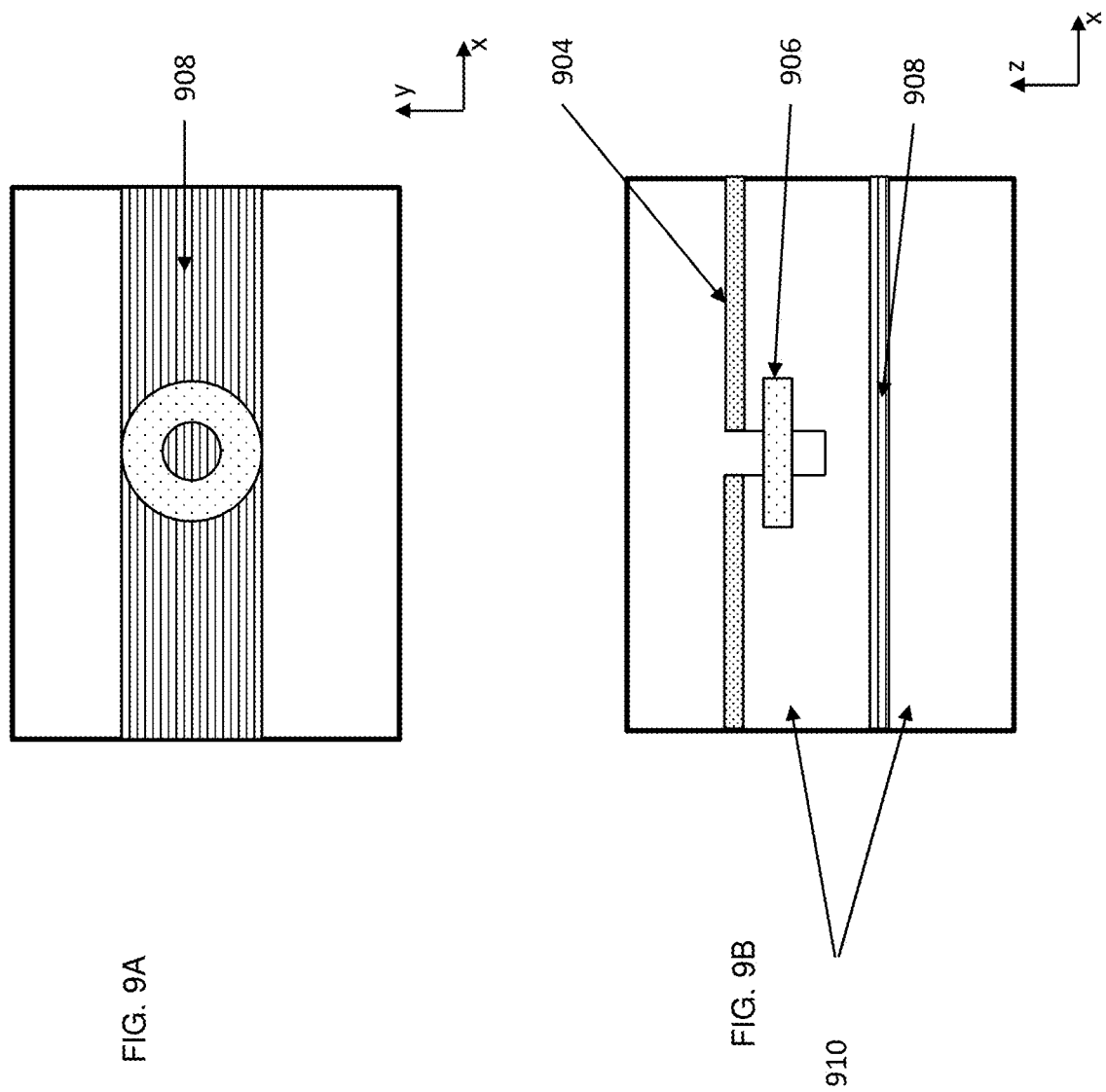

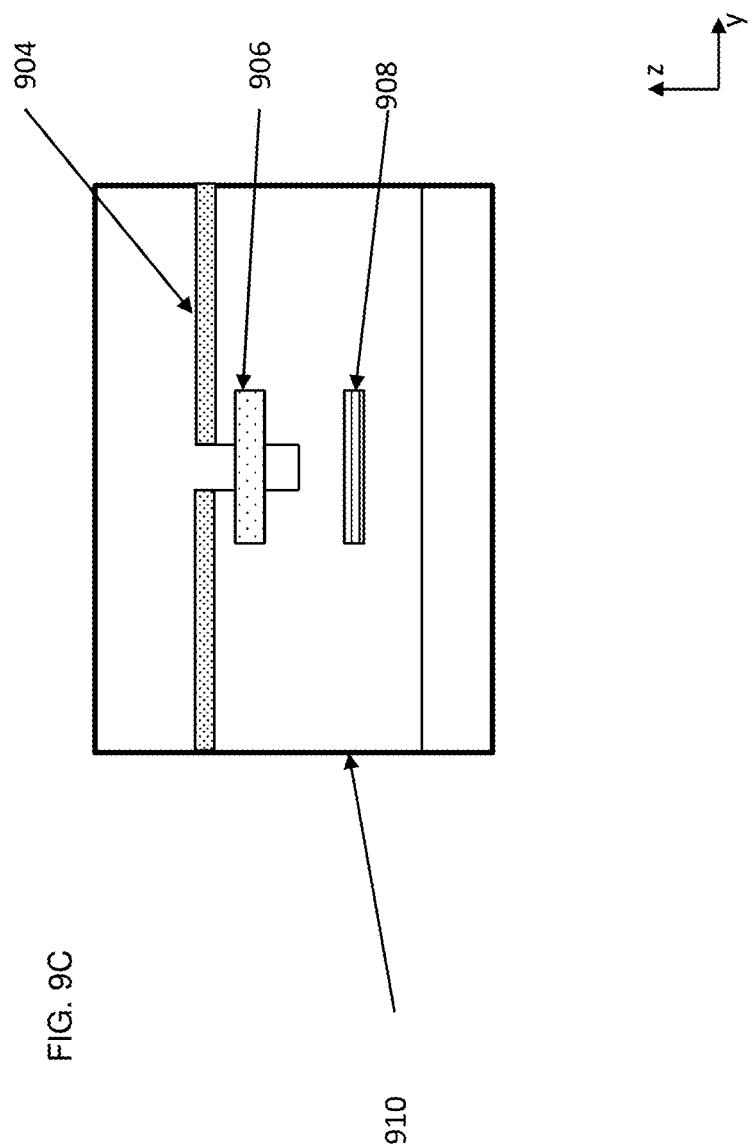

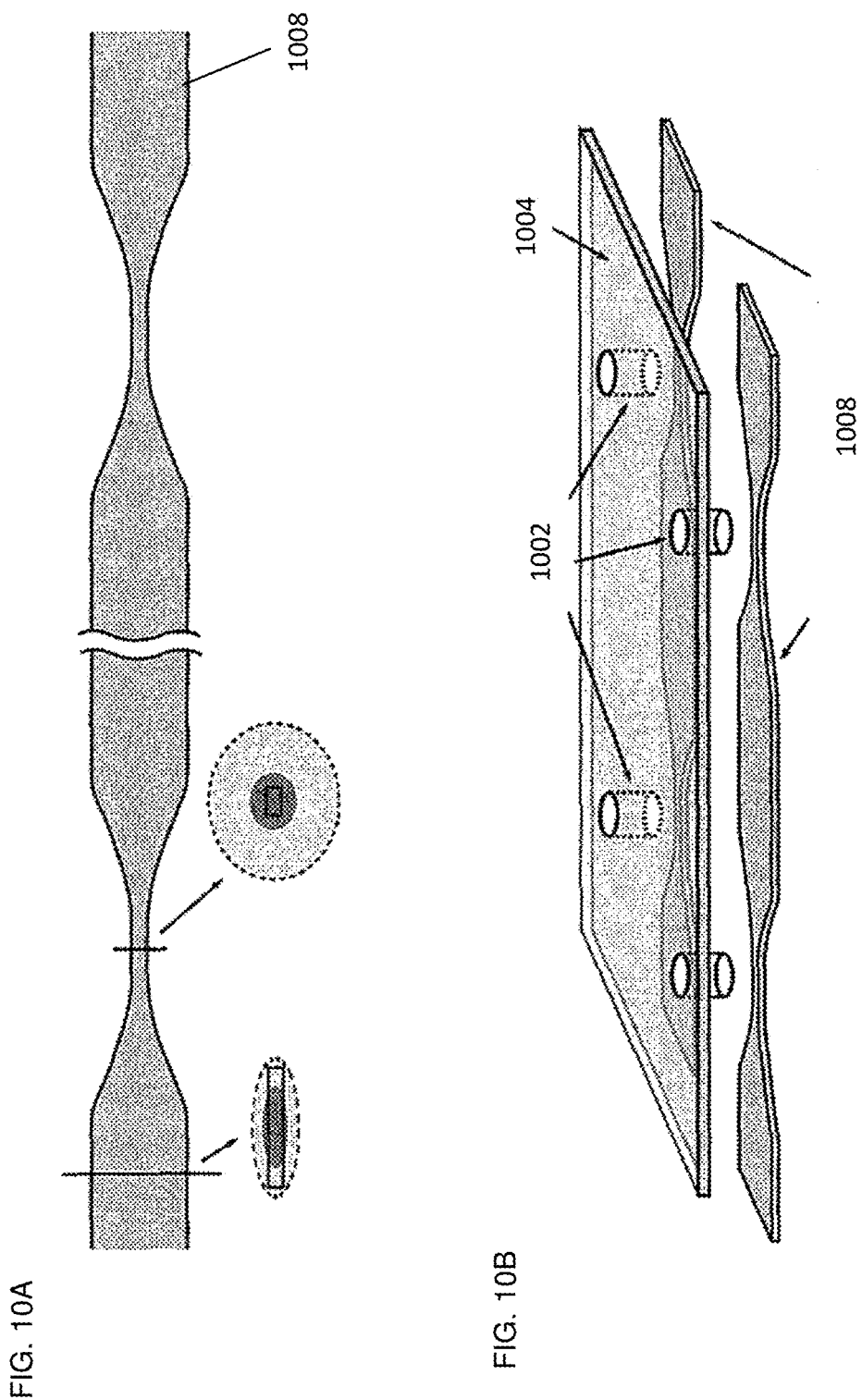

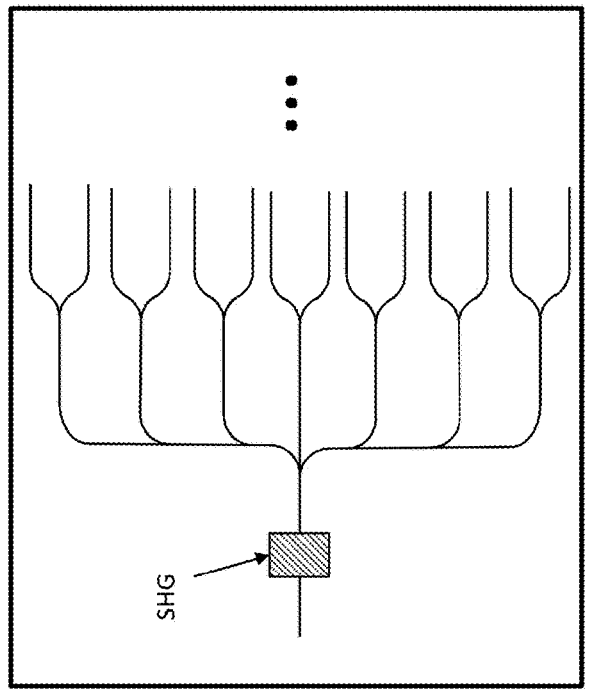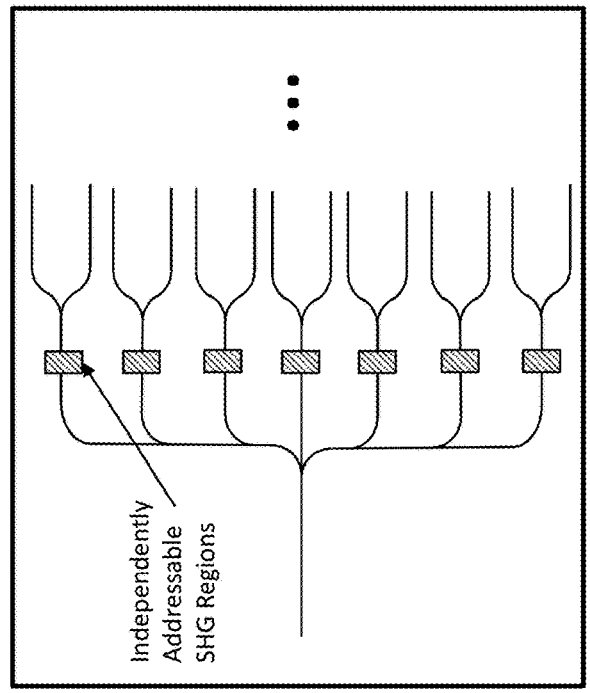
FIG. 14A
FIG. 14B

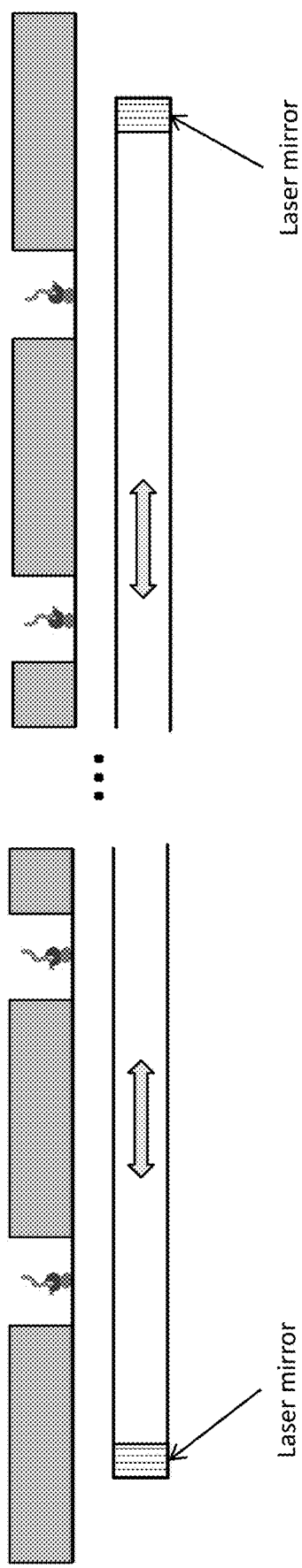
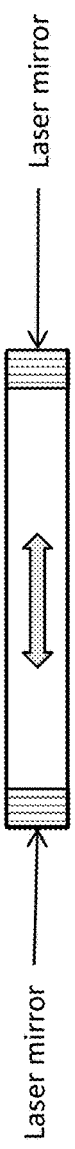
FIG. 15A
FIG. 15B

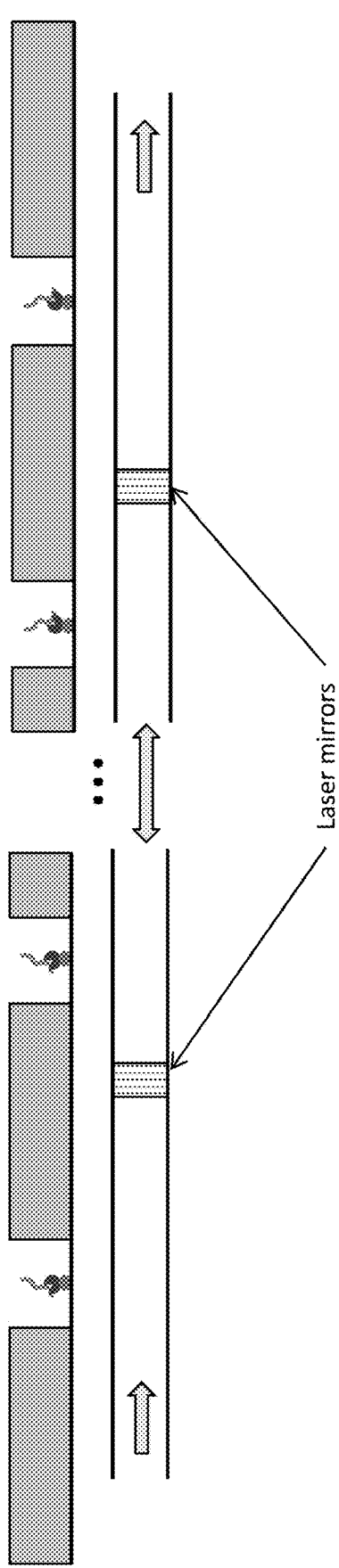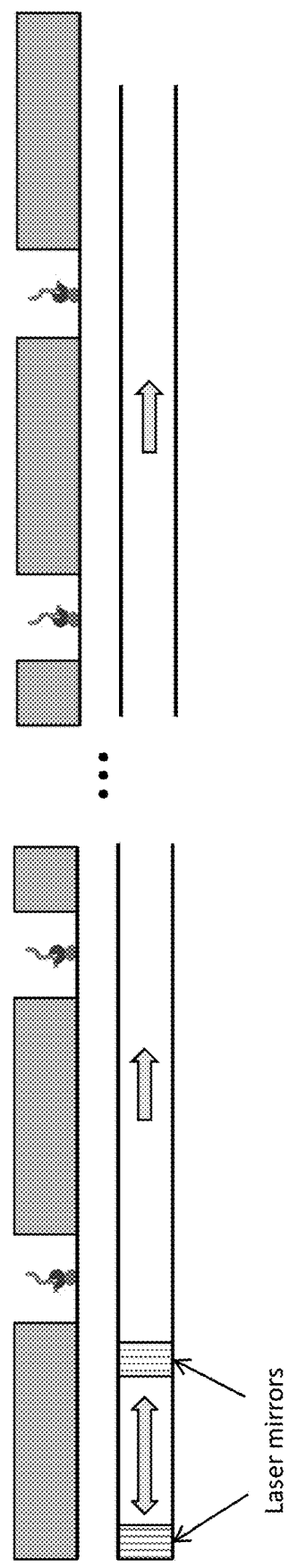

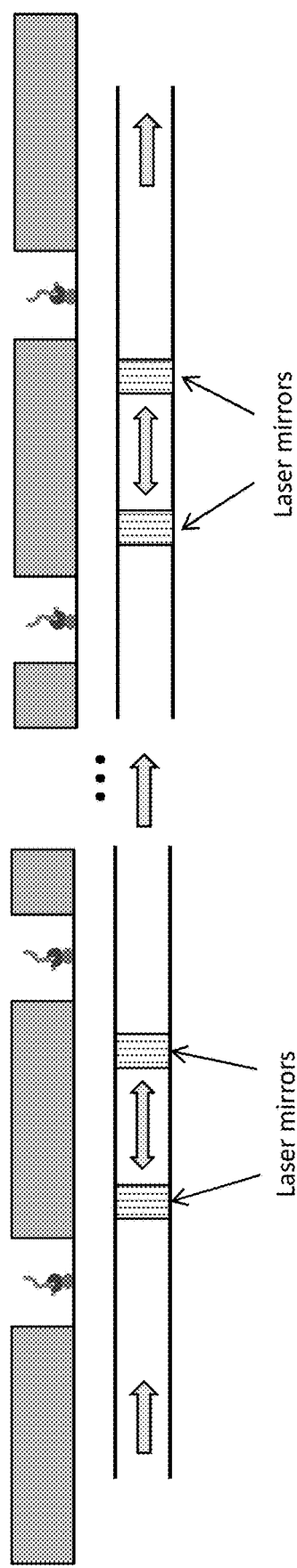
FIG. 15E
FIG. 15F
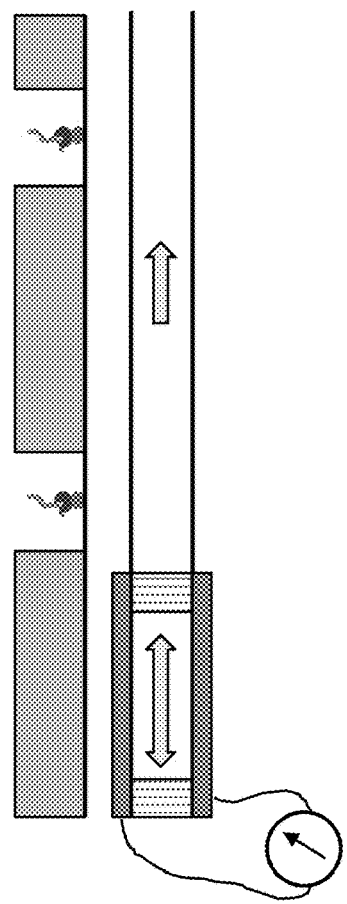
FIG. 15G
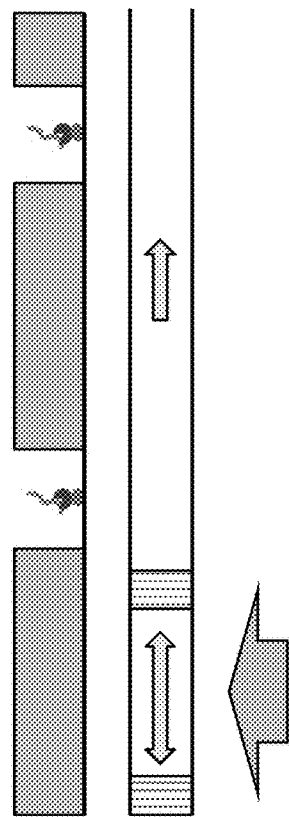

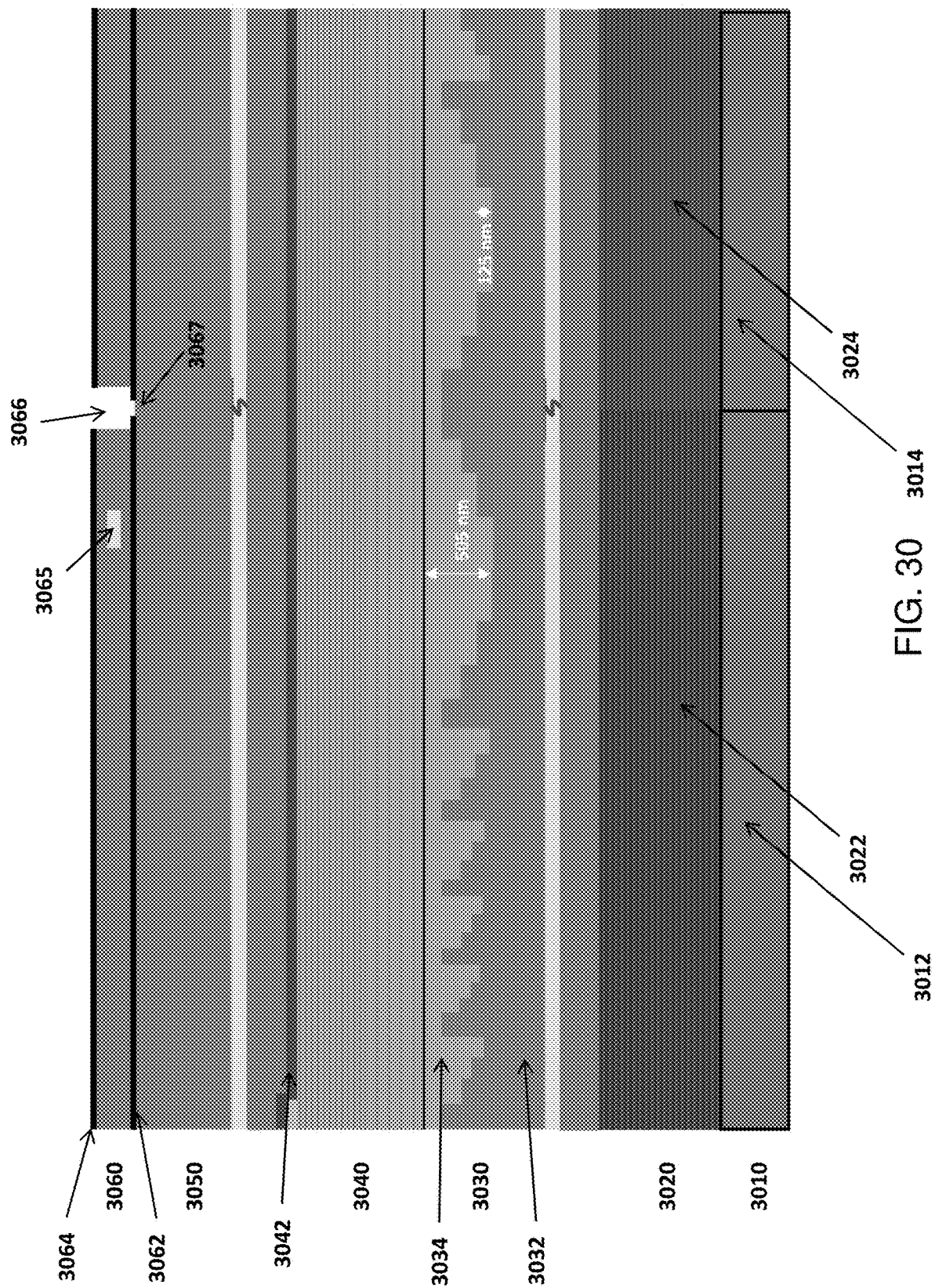

INTEGRATED ILLUMINATION OF OPTICAL ANALYTICAL DEVICES

CROSS-REFERENCE TO RELATED APPLICATION

This application is a continuation of U.S. patent application Ser. No. 15/489,655, filed on Apr. 17, 2017, which is a continuation of U.S. patent application Ser. No. 14/187,198, filed on Feb. 21, 2014, now U.S. Pat. No. 9,624,540 B2, and claims the benefit under 35 U.S.C. § 119(e) of U.S. Provisional Application No. 61/768,053, filed on Feb. 22, 2013, the disclosures of which are each incorporated herein by reference in their entireties.

BACKGROUND OF THE INVENTION

In analytical systems, the ability to increase the number of analyses being carried out at any given time by a given system has been a key component to increasing the utility and extending the lifespan of such systems. In particular, by increasing the multiplex factor of analyses with a given system, one can increase the overall throughput of the system, thereby increasing its usefulness while decreasing the costs associated with that use.

In optical analyses, increasing multiplex often poses increased difficulties, as it may require more complex optical systems, increased illumination or detection capabilities, and new reaction containment strategies. In some cases, systems seek to increase multiplex by many fold, and even orders of magnitude, which further implicate these considerations. Likewise, in certain cases, the analytical environment for which the systems are to be used is so highly sensitive that variations among different analyses in a given system may not be tolerable. These goals are often at odds with a brute force approach of simply making systems bigger and of higher power, as such steps often give rise to even greater consequences, e.g., in inter reaction cross-talk, decreased signal to noise ratios resulting from either or both of lower signal and higher noise, and the like. It would therefore be desirable to provide analytical systems that have substantially increased multiplex for their desired analysis, and particularly for use in highly sensitive reaction analyses, and in many cases, to do so while minimizing negative impacts of such increased multiplex.

Conventional optical systems employ complex optical trains that direct, focus, filter, split, separate, and detect light to and/or from the sample materials. Such systems typically employ an assortment of different optical elements to direct, modify, and otherwise manipulate light directed to and/or received from a reaction site. Such systems are typically complex and costly and tend to have significant space requirements. For example, typical systems employ mirrors and prisms in directing light from its source to a desired destination. Additionally, such systems may include light-splitting optics such as beam-splitting prisms to generate two or more beams from a single original beam.

There is a continuing need to increase the performance of analytical systems and reduce the cost associated with manufacturing and using the system. In particular, there is a continuing need to increase the throughput of analytical systems. There is a continuing need to reduce the size and complexity of analytical system. There is a continuing need for analytical systems that have flexible configurations and are easily scalable.

SUMMARY OF THE INVENTION

The present disclosure addresses these and other needs by providing an analytical device comprising:

a substrate;
an integrated illumination element;
a plurality of illumination volumes; and
a plurality of detector elements.

In one aspect, the disclosure provides an analytical device wherein the integrated illumination element is disposed in the substrate, the integrated illumination element comprises an optical resonator within a waveguide, the optical resonator comprises a laser medium and a first and a second mirror disposed within the waveguide, and the plurality of illumination volumes are contained in a plurality of nanowells disposed on a surface of the substrate, wherein at least a first nanowell is optically coupled to the waveguide and to one of the detector elements.

In some embodiments of this aspect of the invention, the first nanowell is optically coupled to the waveguide by evanescent illumination emanating from the waveguide.

In some embodiments, the first mirror and the second mirror are 100% reflection mirrors, and the first nanowell is optically coupled to the waveguide at a region directly adjacent to the optical resonator.

In some embodiments, no more than one nanowell or row of nanowells is coupled to the waveguide.

In some embodiments, the first mirror is a high reflector mirror and the second mirror is a partial reflector mirror.

In some embodiments, the optical resonator amplifies optical energy in the waveguide.

In some embodiments, the first nanowell is optically coupled to the waveguide at a region remote from the optical resonator.

In some embodiments, the analytical device further comprises a second nanowell optically coupled to the waveguide by evanescent illumination emanating from the waveguide, wherein the first nanowell is optically coupled to the waveguide at a region directly adjacent to the optical resonator and the second nanowell is optically coupled to the waveguide at a region remote from the optical resonator.

In some embodiments, the integrated illumination element of the device comprises a plurality of optical resonators within a waveguide, each optical resonator comprising a laser medium and a first and a second mirror disposed within the waveguide; and wherein the first nanowell is optically coupled to the integrated illumination element.

In some embodiments, at least one of the optical resonators amplifies optical energy in the waveguide, and in some embodiments, the first nanowell is optically coupled to the waveguide at a region remote from the optical resonators.

In some embodiments of the device, at least one optical resonator is optically pumped, and in some embodiments, at least one optical resonator is electrically pumped.

In another aspect, the disclosure provides an analytical device wherein the integrated illumination element is disposed on the surface of the substrate, the plurality of detector elements are disposed below the surface of the substrate, the integrated illumination element is partly surrounded by an opaque layer, and the plurality of illumination volumes are contained in a plurality of nanowells disposed on a surface of the substrate, wherein at least a first nanowell is optically coupled to the integrated illumination element and to one of the detector elements.

In certain embodiments according to this aspect of the device, the first nanowell comprises a bottom surface and a first side surface. The first nanowell in these embodiments may be optically coupled to the integrated illumination element through the first side surface of the first nanowell, and the opaque layer may partly cover the first side surface of the first nanowell. In other embodiments, the opaque layer does not cover the first side surface of the first nanowell.

In some embodiments, the first nanowell is optically coupled to the integrated illumination element through the bottom surface of the first nanowell, and the opaque layer may completely cover the first side surface of the first nanowell.

In some embodiments of the device, the first nanowell is optically coupled to the integrated illumination element through a transfer waveguide disposed in the substrate, and the transfer waveguide may, in some embodiments, illuminate no more than one of the nanowells, whereas in other embodiments, the transfer waveguide may illuminate more than one of the nanowells.

In some embodiments, the first nanowell of the analytical device may be optically coupled to the detector element through the bottom surface of the first nanowell, and the first nanowell may further comprise a second side surface, wherein the second side surface comprises a micromirror. In some of these embodiments, the micromirror may increase the optical coupling of an illumination volume contained in the first nanowell to the integrated illumination element.

In some embodiments, the second side surface may have a concave shape or may be angled toward the bottom surface of the first nanowell.

In some embodiments of the device, the opaque layer partly surrounding the integrated illumination element comprises a micromirror, which may, in some embodiments, increase the optical coupling of an illumination volume contained in the first nanowell to the integrated illumination element.

In some embodiments, the opaque layer partly surrounding the integrated illumination element is cylindrical.

In some embodiments, the analytical device further comprises a filter layer disposed between the surface of the substrate and the plurality of detector elements, and the filter layer may decrease the transmission of optical energy from the integrated illumination element to the plurality of detector elements.

In some embodiments, at least one detector element of the plurality of detector elements in the device further comprises a microlens or a light redirection cone.

In some embodiments of the analytical device, the integrated illumination element comprises a waveguide, a discrete light source, or a light-emitting diode or a semiconductor laser diode.

In yet another aspect, the disclosure provides an analytical device wherein the integrated illumination element comprises a plurality of discrete light sources disposed on the surface of the substrate.

According to some embodiments, the device further comprises an opaque layer disposed on the surface of the substrate.

In some embodiments, the plurality of detector elements are disposed below the surface of the substrate, whereas in other embodiments, the plurality of detector elements are disposed above the opaque layer. In some embodiments, the device further comprises a cover slip disposed between the opaque layer and the plurality of detector elements.

In some embodiments, the plurality of illumination volumes are contained in a plurality of nanowells disposed on a surface of the substrate, wherein at least a first nanowell is optically coupled to one of the discrete light sources and to one of the detector elements. In some of these devices, the device further comprises an opaque layer disposed on the surface of the substrate, wherein the plurality of nanowells are disposed in the opaque layer, and wherein the first nanowell comprises a bottom surface and a first side surface. In some embodiments, the first nanowell is optically coupled to a first discrete light source through the bottom surface of the first nanowell, and in some embodiments, the first nanowell is optically coupled to the first discrete light source through the first side surface of the first nanowell.

In some embodiments, the device further comprises a conductor element and an insulator element associated with the first discrete light source, wherein the insulator element is disposed between the conductor element and the opaque layer.

According to some embodiments, the plurality of discrete light sources in the analytical device is a plurality of light-emitting diodes or a plurality of semiconductor laser diodes. In some embodiments, the plurality of semiconductor laser diodes is a plurality of vertical cavity surface-emitting lasers. In some embodiments, the plurality of vertical cavity surface-emitting lasers are tuned to emit an evanescent illumination from an upper reflector.

According to some embodiments, the analytical device further comprises an analyte disposed within at least one illumination volume. In some embodiments, the analyte comprises a biological sample, and, in some embodiments, the biological sample comprises a nucleic acid and/or a polymerase enzyme.

In some embodiments, the analytical device comprises at least 1,000, at least 10,000, at least 100,000, at least 1,000,000, or at least 10,000,000 illumination volumes.

In some embodiments of the device, at least one detector element of the plurality of detector elements further comprises a spectral diversion element, and in some embodiments, at least one detector element of the plurality of detector elements further comprises a light redirection cone.

BRIEF DESCRIPTION OF THE DRAWINGS

FIGS. 1A-1B schematically illustrate an exemplary nucleic acid sequencing process that can be carried out using aspects of the invention.

FIG. 7A illustrates an analytical device containing a waveguide core, cladding, metallic/opaque layer, and a material of high dielectric or metal in the vicinity of the nanometer-scale aperture, as viewed in the x-z plane. FIG. 7B illustrates an alternative device structure, having a geometric pattern of high dielectric material or metal surrounding the aperture.

FIG. 8A shows a top view in the x-y plane with the opaque, metallic layer omitted from the view. FIG. 8B shows a cross-sectional view in the y-z plane.

FIGS. 9A-9C provide a schematic of the design used in simulations of coupling efficiencies. FIG. 9A shows a top view of the simulated device in the x-y plane with the opaque, metallic layer omitted from the view. FIG. 9B shows a side view of the simulated device in the x-z plane. FIG. 9C shows a cross-sectional view of the simulated device in the y-z plane.

FIGS. 10A-10B illustrate an example of the dimensional modulation of the waveguides.

FIG. 11A: cross-sectional view; FIG. 11B: top-down view.

FIGS. 14A-14B schematically illustrate a waveguide containing a wavelength conversion element just after the coupler (FIG. 14A) and another exemplary waveguide with independently addressable SHG elements (FIG. 14B).

FIGS. 15A-15G illustrate examples of devices containing optical resonators integrated into waveguides disposed within the substrate. In each case, the waveguide is integrated into the device in a layer below the layer containing the nanowells. Double-headed arrows within the waveguide represent the confinement of optical energy along the cavity direction. The optical energy is confined inside the cavity as a standing wave. Single-headed arrows within the waveguide represent transmission of optical energy along the waveguide. The large arrow in FIG. 15F represents an optical pump having equal or shorter wavelength. The device shown attached to the left end of the waveguide in FIG. 15G represents an electrical pump.

FIG. 30 illustrates a cross-sectional view of a portion of an exemplary device in which the waveguides and the nanowells are disposed in the same layer of the device. The waveguides thus provide illumination from the side of the nanowells.

DETAILED DESCRIPTION OF THE INVENTION

Integrated Optical Detection Devices

Figure 2:
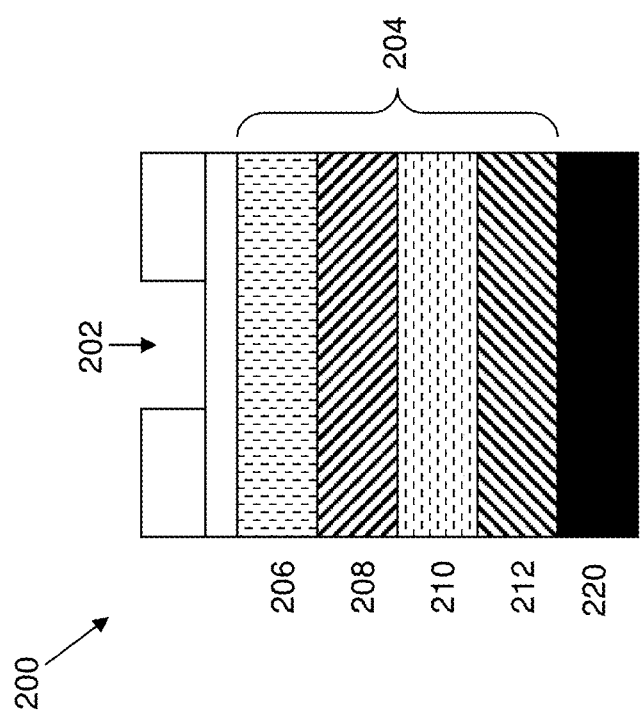
FIG. 2 provides a schematic block diagram of an integrated analytical device.

Multiplexed optical analytical systems are used in a wide variety of different applications. Such applications can include the analysis of single molecules, and can involve observing, for example, single biomolecules in real time as they carry out reactions. For ease of discussion, such multiplexed systems are discussed herein in terms of a preferred application: the analysis of nucleic acid sequence information, and particularly, single molecule nucleic acid sequence analysis. Although described in terms of a particular application, it should be appreciated that the applications for the devices and systems described herein are of broader application.

In the context of single molecule nucleic acid sequencing analyses, a single immobilized nucleic acid synthesis complex, comprising a polymerase enzyme, a template nucleic acid, whose sequence is being elucidated, and a primer sequence that is complementary to a portion of the template sequence, is observed in order to identify individual nucleotides as they are incorporated into the extended primer sequence. Incorporation is typically monitored by observing an optically detectable label on the nucleotide, prior to, during, or following its incorporation. In some cases, such single molecule analyses employ a "one base at a time approach", whereby a single type of labeled nucleotide is introduced to and contacted with the complex at a time. Upon reaction, unincorporated nucleotides are washed away from the complex, and the labeled incorporated nucleotides are detected as a part of the immobilized complex.

In some instances, only a single type of nucleotide is added to detect incorporation. These methods then require a cycling through of the various different types of nucleotides (e.g., A, T, G and C) to be able to determine the sequence of the template. Because only a single type of nucleotide is contacted with the complex at any given time, any incorporation event is, by definition, an incorporation of the contacted nucleotide. These methods, while somewhat effective, generally suffer from difficulties when the template sequence includes multiple repeated nucleotides, as multiple bases may be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but the nucleotides are distinguishable by the presence on each type of nucleotide a different optical label. Accordingly, such methods can use a single step to identify a given base in the sequence. In particular, all four nucleotides, each bearing a distinguishable label, are added to the immobilized complex. The complex is then interrogated to identify which type of base was incorporated, and as such, the next base in the template sequence.

In some cases, these methods only monitor the addition of one base at a time, and as such, they (and in some cases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

In another example, single molecule primer extension reactions are monitored in real time, to identify the continued incorporation of nucleotides in the extension product to elucidate the underlying template sequence. In such single molecule real time (or SMRT™) sequencing, the process of incorporation of nucleotides in a polymerase-mediated template-dependent primer extension reaction is monitored as it occurs. In preferred aspects, the template/polymerase primer complex is provided, typically immobilized, within an optically-confined region, such as a zero mode waveguide (ZMW), or proximal to the surface of a transparent substrate, optical waveguide, or the like (see e.g., U.S. Pat. Nos. 6,917,726, 7,170,050, and 7,935,310, the full disclosures of which are hereby incorporated by reference herein in their entirety for all purposes). The optically-confined region is illuminated with an appropriate excitation radiation for the fluorescently-labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated.

A schematic illustration of this sequencing process is shown in FIGS. 1A-1B. As shown in FIG. 1A, an immobilized complex 102 of a polymerase enzyme, a template nucleic acid and a primer sequence are provided within an observation volume (as shown by dashed line 104) of an optical confinement, of e.g., a zero mode waveguide 106. As an appropriate nucleotide analog, e.g., nucleotide 108, is incorporated into the nascent nucleic acid strand, it is illuminated for an extended period of time corresponding to the retention time of the labeled nucleotide analog within the observation volume during incorporation. The incorporation reaction thus produces a signal associated with that retention, e.g., signal pulse 112 as shown by the A trace in FIG. 1B. Once incorporated, the label that was attached to the polyphosphate component of the labeled nucleotide analog, is released. When the next appropriate nucleotide analog, e.g., nucleotide 110, is contacted with the complex, it too is incorporated, giving rise to a corresponding signal 114 in the T trace of FIG. 1B. By monitoring the incorporation of bases into the nascent strand, as dictated by the underlying complementarity of the template sequence, long stretches of sequence information of the template can be obtained.

The above sequencing reaction may be incorporated into a device, typically an integrated analytical device, that provides for the simultaneous observation of multiple sequencing reactions, ideally in real time. While the components of each device, and the configuration of the devices in the system, may vary, each integrated analytical device typically comprises, at least in part, the general structure shown as a block diagram in FIG. 2. As shown, an integrated analytical device 200 typically includes a reaction cell 202, in which the reactants are disposed and from which the optical signals emanate. The analysis system further includes a detector element 220, which is disposed in optical communication with the reaction cell 202. Optical communication between the reaction cell 202 and the detector element 220 may be provided by an optical train 204 comprised of one or more optical elements generally designated 206, 208, 210 and 212 for efficiently directing the signal from the reaction cell 202 to the detector 220. These optical elements may generally comprise any number of elements, such as lenses, filters, gratings, mirrors, prisms, refractive material, or the like, or various combinations of these, depending upon the specifics of the application. By integrating these elements into a single device architecture, the efficiency of the optical coupling between the reaction cell and the detector is improved. Examples of integrated analytical systems, including various approaches for illuminating the reaction cell and detecting optical signals emitted from the reaction cell, are described in U.S. Patent Application Publication Nos. 2012/0014837, 2012/0019828, and 2012/0021525, which are each incorporated by reference herein in their entireties for all purposes.

Conventional analytical systems typically measure multiple spectrally distinct signals or signal events and must therefore utilize complex optical systems to separate and distinctly detect those different signal events. The optical path of an integrated device may be simplified, however, by a reduction in the amount or number of spectrally distinguishable signals that are detected. Such a reduction is ideally effected, however, without reducing the number of distinct reaction events that can be detected. For example, in an analytical system that distinguishes four different reactions based upon four different detectable signal events, where a typical system would assign a different signal spectrum to each different reaction, and thereby detect and distinguish each signal event, in an alternative approach, four different signal events would be represented at fewer than four different signal spectra, and would, instead, rely, at least in part, on other non-spectral distinctions between the signal events.

For example, a sequencing operation that would conventionally employ four spectrally distinguishable signals, e.g., a "four-color" sequencing system, in order to identify and characterize the incorporation of each of the four different nucleotides, would, in the context of an alternative configuration, employ a one-color or two-color analysis, e.g., relying upon a signals having only one or two distinct or distinguished spectral signals. However, in such an alternative configuration, this reduction in reliance on signal spectral complexity does not come at the expense of the ability to distinguish signals from multiple, i.e., a larger number of different signal producing reaction events. In particular, instead of relying solely on signal spectrum to distinguish reaction events, such an alternative configuration may rely upon one or more signal characteristics other than emission spectrum, including, for example, signal intensity, excitation spectrum, or both to distinguish signal events from each other.

In one particular alternative configuration, the optical paths in an integrated analytical device may thus be simplified by utilizing signal intensity as a distinguishing feature between two or more signal events. In its simplest iteration, and with reference to an exemplary sequencing process, two different types of nucleotides would bear fluorescent labels that each emit fluorescence under the same excitation illumination, i.e., having the same or substantially overlapping spectral band, and thus would provide benefits of being excited using a single excitation source and beam. The resulting signals from each fluorescent label would have distinct signal intensities or amplitudes under that same illumination, and would be distinguishable by their respective signal amplitudes. These two signals could have partially or entirely overlapping emission spectra, but separation of the signals based upon any difference in emission spectrum would be unnecessary.

Accordingly, for analytical systems using two or more signal events that differ in signal amplitude, the integrated analytical devices of such systems can readily benefit through the removal of some or all of those components that would normally be used to separate spectrally distinct signals, such as multiple excitation sources and their associated optical trains, as well as the color separation optics, e.g., filters and dichroics, for the signal events, which in many cases, requires at least partially separate optical trains and detectors for each spectrally distinct signal. As a result, the optical paths for these integrated analytical devices are greatly simplified, allowing placement of detector elements in closer proximity to reaction regions, and improving overall performance of the detection process for these devices.

Figure 3A:
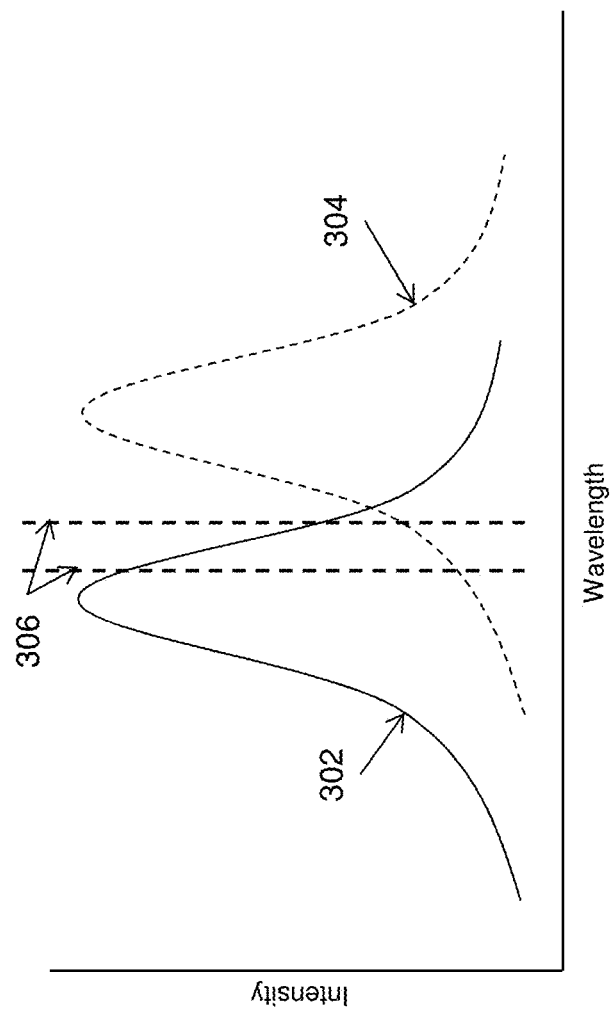
FIG. 3A provides a schematic of excitation spectra for two signal events and an indicated narrow band excitation illumination, while FIG. 3B schematically illustrates the resulting detected signal based upon the narrow band illumination of the two signal events.
Figure 3B:
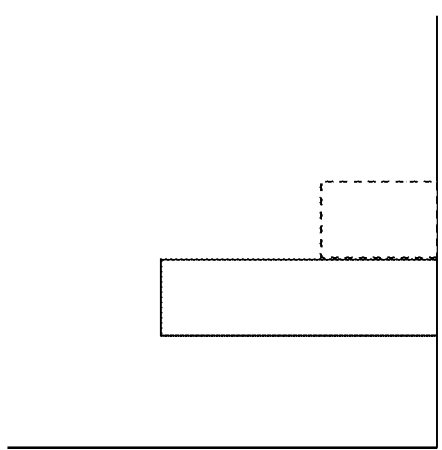

Provision of signal-producing reactants that will produce different signal amplitudes under a particular excitation illumination profile may be accomplished in a number of ways. For example, different fluorescent labels may be used that present excitation spectral profiles that overlap but include different maxima. As such, excitation at a narrow wavelength will typically give rise to differing signal intensities for each fluorescent group. This is illustrated in FIG. 3A, which shows the excitation spectra of two different fluorescent label groups (solid and dashed lines 302 and 304, respectively). When subjected to excitation illumination at the wavelength range shown by vertical lines 306, each fluorescent label will emit a signal at the corresponding amplitude. The resulting signal intensities at a given excitation wavelength are then shown in the bar chart of FIG. 3B, shown as the solid lined and dashed lined bars, respectively. The difference in intensity of these two signal-producing labels at the given excitation wavelength can then be readily used to distinguish the two signal events. As will be appreciated, such spectrally indistinct signals would not be easily distinguishable when occurring simultaneously, as they would result in an additive overlapping signal, unless, as discussed below, such spectrally indistinct signals result from spectrally distinct excitation wavelengths. As will be appreciated, this same approach may be used with more than two label groups where the resulting emission at a given excitation spectrum have distinguishable intensities or amplitudes.

Similarly, two different fluorescent labeling groups may have the same or substantially similar excitation spectra, but provide different and distinguishable signal emission intensities due to the quantum yield or extinction coefficient of those labeling groups.

Further, although described in terms of two distinct fluorescent dyes, it will be appreciated that each different labeling group may each include multiple labeling molecules. For example, each reactant may include an energy transfer dye pair that yields emissions of differing intensities upon excitation with a single illumination source. For example, a labeling group may include a donor fluorophore that is excited at a given excitation wavelength, and an acceptor fluorophore that is excited at the emission wavelength of the donor, resulting in energy transfer to the acceptor. By using different acceptors, whose excitation spectra overlap the emission spectrum of the donor to differing degrees, such an approach can produce overall labeling groups that emit at different signal amplitudes for a given excitation wavelength and level. Likewise, adjusting the energy transfer efficiency between the donor and acceptor will likewise result in differing signal intensities at a given excitation illumination. Examples of these approaches are described in U.S. Patent Application Publication No. 2010/0255488, the full disclosure of which is incorporated by reference herein in its entirety for all purposes.

Alternatively, different signal amplitudes may be provided by different multiples of signal producing label groups on a given reactant, e.g., putting a single label molecule on one reactant while putting 2, 3, 4 or more individual label molecules on a different reactant. The resulting emitted signal will be reflective of the number of labels present on a reactant and thus will be indicative of the identity of that reactant. Methods and compositions for coupling multiple labeling groups on reactants, such as nucleotide analogs, are described in, for example, U.S. patent application Ser. No. 13/218,312, filed Aug. 25, 2011, and incorporated by reference herein in its entirety for all purposes.

As described above, integrated analytical devices making use of such approaches see a reduction in complexity by elimination of spectral discrimination requirements, e.g., using signal amplitude or other non-spectral characteristics as a basis for signal discrimination. Integrated analytical devices that combine such non-spectral discrimination approaches with the more common spectral discrimination approaches may also provide advantages over more complex spectral discrimination systems. By shifting from a "four-color" discrimination system to a system that distinguishes signals based upon signal intensity and color, one can still reduce the complexity of the overall optical system relative to a conventional four-color separation scheme. For example, in an analytical operation that detects four discrete reaction events, e.g., in a nucleic acid sequencing analysis, two signal events may be provided within a given emission/detection spectrum, i.e., emitting signals within the same spectral window, and the other two events within a distinct emission/detection spectrum. Within each spectral window, the pair of signal events produce distinguishable signal intensities relative to each other.

For ease of discussion, this concept is described in terms of two groups of fluorescent signal events, where members of each group differ by fluorescent intensity, and the groups differ by virtue of their emission spectrum. As will be appreciated, the use of simplified optics systems, e.g., using two detection channels for two distinct emission spectra, does not require that the emission profiles of the two groups of signals do not overlap or that the emission spectra of members of each group perfectly overlap. Instead, in many preferred aspects, more complex signal profiles may be used where each different signal event possesses a unique emission spectrum, but in a way that each signal will present a signal profile within the two detection channels that is unique, based upon the signal intensity in each channel.

Figure 4:
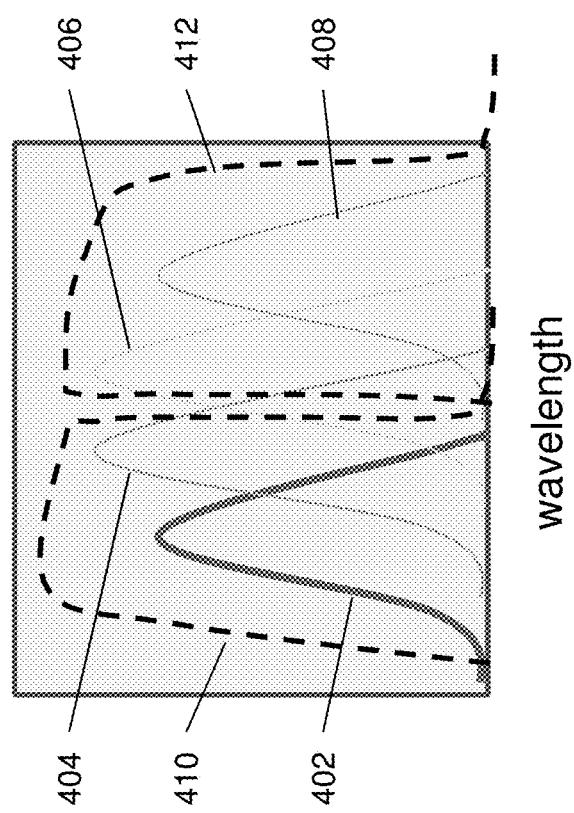
FIG. 4 schematically illustrates the signal profiles for each of four fluorescent labeling groups, overlain with each of two different filter profiles.

FIG. 4 schematically illustrates the signal profiles for each of four fluorescent labeling groups, overlain with each of two different filter profiles. As shown, four label groups yield emission spectra 402, 404, 406 and 408, respectively. While the signals from these four groups partially overlap each other, they each have different maxima. When subjected to a two channel filter scheme, as shown by pass filter lines 410 and 412, the signal from each label will produce a unique signal profile between the two detection channels. In particular, signals are routed through an optical train that includes two paths that are filtered according to the spectral profile shown. For each signal, different levels of emitted light will pass through each path and be detected upon an associated detector. The amount of signal that passes through each filter path is dictated by the spectral characteristics of the signal.

In the case of the above described mixed-mode schemes, detection systems may be provided that include at least two distinct detection channels, where each detection channel passes light within a spectrum that is different from each other channel. Such systems also include a reaction mixture within optical communication of the detection channels, where the reaction mixture produces at least three different optical signals that each produces a unique signal pattern within the two detection channels, as compared to the other optical signals.

In each case, each signal-producing reactant is selected to provide a signal that is entirely distinct from each other signal in at least one of signal intensity and signal channel. As noted above, signal intensity in a given channel is dictated, in part, by the nature of the optical signal, e.g., its emission spectrum, as well as the filters through which that signal is passed, e.g., the portion of that spectrum that is allowed to reach the detector in a given channel. However, signal intensity can also be modulated by random variables, such as orientation of a label group when it is emitting signal, or other variables of the particular reaction. Accordingly, for a signal's intensity to be assured of being entirely different from the intensity of another signal within a given channel, in preferred aspects, this variation is accounted for.

Figure 5:
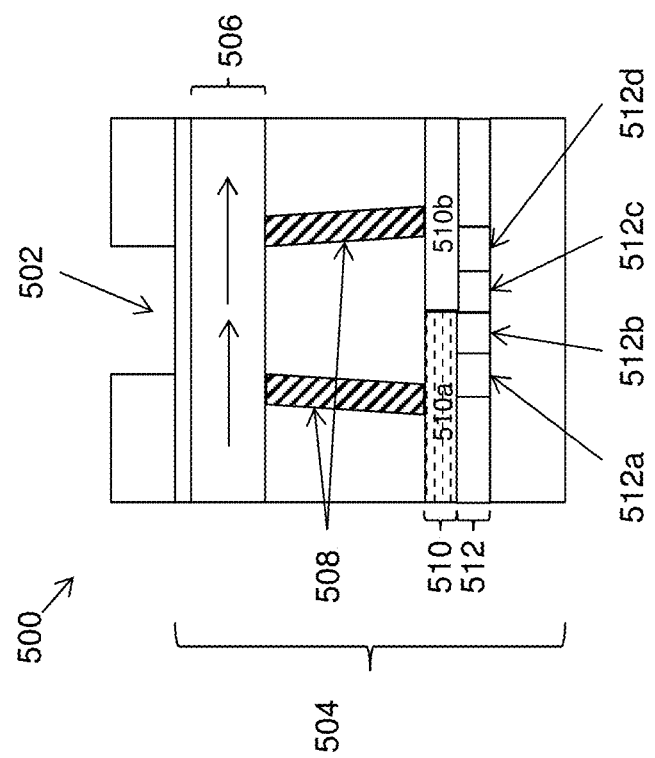
FIG. 5 schematically illustrates an integrated analytical device for detecting signals from a 4-color sequencing reaction.

With a reduced number of spectrally distinct signal events, the complexity of the optical paths for the integrated devices is also reduced. FIG. 5 illustrates a not-to-scale example device architecture for performing optical analyses, e.g., nucleic acid sequencing processes, that rely in part on non-spectral discrimination of differing signals, and optionally, in part on spectral distinction. As shown, an integrated analytical device 500 includes a reaction region 502 that is defined upon a first substrate layer 504. As shown, the reaction region comprises a well disposed in the substrate surface. Such wells may constitute depressions in a substrate surface or apertures disposed through additional substrate layers to an underlying transparent substrate, e.g., as used in zero mode waveguide arrays (See, e.g., U.S. Pat. Nos. 7,181,122 and 7,907,800).

In the device of FIG. 5, excitation illumination is delivered to the reaction region from an excitation light source (not shown) that may be separate from or also integrated into the substrate. As shown, an optical waveguide (or waveguide layer) 506 may be used to convey excitation light (shown by arrows) to the reaction region/well 502, where the evanescent field emanating from the waveguide 506 illuminates reactants within the reaction region 502. Use of optical waveguides to illuminate reaction regions is described in e.g., U.S. Pat. No. 7,820,983 and U.S. Patent Application Publication No. 2012/0085894, which are each incorporated by reference herein in their entireties for all purposes.

The integrated device 500 optionally includes light channeling components 508 to efficiently direct emitted light from the reaction regions to a detector layer 512 disposed beneath the reaction region. The detector layer typically comprises one, or preferably multiple, detector elements 512a-d, e.g., pixels in an array detector, that are optically coupled to a given reaction region. Although illustrated as a linear arrangement of pixels 512a-d, it will be appreciated that such pixels may be arranged in a grid, n×n square, annular array, or any other convenient orientation.

Emitted signals from the reaction region 502 that impinge on these pixels are then detected and recorded. As noted above, an optional single filter layer 510 is disposed between the detector layer and the reaction region, to permit different spectrally distinct signals to travel to different associated pixels 512a and 512b in the detector layer 512. For example, the portion 510a of filter layer 510 allows signals having a first emission spectrum to reach its associated pixels 512a and 512b, while filter portion 510b of filter layer 510 allows only signals having a distinct second spectrum to reach its associated pixels 512c and 512d.

In the context of a sequencing system exploiting such a configuration, incorporation of two of the four nucleotides would produce signals that would be passed through filter portion 510a to pixels 512a and 512b, and blocked by filter portion 510b. As between these two signals, one signal would have a signal intensity higher than the other such that the pixels 512a and 512b in detector layer 512 would be able to produce signal responses indicative of such differing signal intensities. Likewise, incorporation of the other two nucleotides would produce signals that would be passed through filter portion 510b to its associated pixels 512c and 512d, while filter portion 510a would block those signals from reaching pixels 510a and 510b. Again, the signals associated with these two latter signal events would differ based upon their signal intensities or amplitudes.

The detector layer is then operably coupled to an appropriate circuitry, typically integrated into the substrate, for providing a signal response to a processor that is optionally included integrated within the same device structure or is separate from but electronically coupled to the detector layer and associated circuitry. Examples of types of circuitry are described in U.S. Patent Application Publication No. 2012/0019828.

As will be appreciated from the foregoing disclosure and FIG. 5, the integrated analytical devices described herein do not require the more complicated optical paths that are necessary in systems utilizing conventional four-color optics, obviating the need for excessive signal separation optics, dichroics, prisms, or filter layers. In particular, although shown with a single filter layer, as noted, in optional aspects, the filter layer could be eliminated or could be replaced with a filter layer that blocks stray light from the excitation source rather than distinguishing different emission signals from the reaction region. Even including the filter layer 510, results in simplified and/or more efficient optics as compared to conventional four-color systems, which would require either multilayer filters, or narrow band pass filters, which typically require hybrid layers or composite approaches over each subset of pixels, thus blocking signal from reaching three of the four pixel subsets at any given emission wavelength, resulting in detection of far fewer photons from each signal event. The optics configuration shown in FIG. 5, on the other hand, only blocks a smaller portion of the overall signal light from reaching the detector. Alternatively, such conventional systems would require separation and differential direction of all four different signal types, resulting in inclusion of additional optical elements, e.g., prisms or gratings, to achieve spectral separation.

Figure 6:
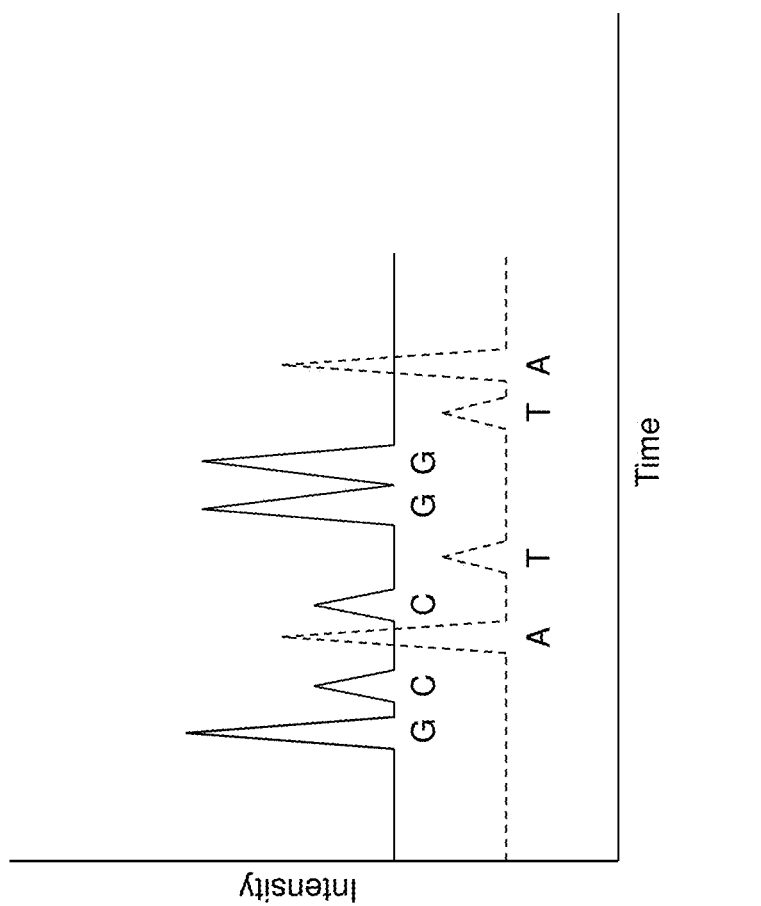
FIG. 6 schematically illustrates signal traces for a two-color, two-amplitude sequence-by-synthesis reaction.

FIG. 6 shows a schematic exemplar signal output for a real time sequencing operation using a two color/two amplitude signal set from an integrated system of the invention where one trace (dashed) denotes signals associated with incorporation of A (high intensity signal) and T (lower intensity signal) bases, while the other signal trace (solid line), denotes the signals of a different emission spectrum, associated with G (high) and C (low) bases. The timing of incorporation and the identity of the base incorporated, as derived from the color channel and intensity of the signal, are then used to interpret the base sequence.

Arrays of Integrated Optical Detection Devices

In order to obtain the volumes of sequence information that may be desired for the widespread application of genetic sequencing, e.g., in research and diagnostics, higher throughput systems are desired. By way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments.

As described above, and as shown in FIGS. 1A-1B, the template/DNA polymerase-primer complex of such a sequencing system is provided, typically immobilized, within an optically confined region, such as a zero mode waveguide (ZMW), or proximal to the surface of a transparent substrate, optical waveguide, or the like. Preferably, such reaction cells are arrayed in large numbers upon a substrate in order to achieve the scale necessary for genomic or other large-scale DNA sequencing approaches. Such arrays preferably comprise a complete integrated analytical device, such as, for example, the devices shown in the block diagrams of FIGS. 2 and 5. Examples of integrated systems comprising arrays of optical analytical devices are provided in U.S. Patent Application Publication Nos. 2012/0014837; 2012/0019828; and 2012/0021525.

Arrays of integrated analytical devices, such as arrays of devices comprising ZMWs, can be fabricated at ultra-high density, providing anywhere from 1000 ZMWs per $cm^2$, to 10,000,000 ZMWs per $cm^2$, or more. Thus, at any given time, it may be desirable to analyze the reactions occurring in 100, 1000, 3000, 5000, 10,000, 20,000, 50,000, 100,000, 1 Million, 5 Million, 10 Million, or more ZMWs or other reaction regions within a single analytical system or even on a single substrate.

In order to achieve the ultra-high density of ZMWs necessary for such arrays, the dimensions of each ZMW must be relatively small. For example, the length and width of each ZMW is typically in the range of from 50 nm to 600 nm, ideally in the range from 100 nm to 300 nm. It should be understood that smaller dimensions allow the use of smaller volumes of reagents and may, in some cases, help to minimize background signals from reagents outside the reaction zone and/or outside the illumination volume. Accordingly, in some embodiments, the depth of the ZMW may be in the range of 50 nm to 600 nm, more ideally in the range of 100 nm to 500 nm, or even more ideally in the range of 150 to 300 nm.

It should also be understood that shape of the ZMW will be chosen according to the desired properties and methods of fabrication. For example, the shape of the ZMW (e.g., when viewed from above the ZMW, for example as from the top of the drawings in FIGS. 2 and 5) may be circular, elliptical, square, rectangular, or any other desired shape. Furthermore, the walls of the ZMW may be fabricated to be vertical, for example as shown in the reaction cells of FIGS. 2 and 5. Alternatively, the walls of the ZMW may be fabricated to slope inward or outward if so desired. In the case of a circular ZMW, an inward or outward slope would result in, for example, a cone-shaped or inverted cone-shaped ZMW.

Using the foregoing systems, simultaneous targeted illumination of thousands or tens of thousands of ZMWs in an array has been described. However, as the desire for multiplex increases, the density of ZMWs on an array, and the ability to provide targeted illumination of such arrays, increases in difficulty, as issues of ZMW cross-talk (signals from neighboring ZMWs contaminating each other as they exit the array), decreased signal:noise ratios arising from higher levels of denser illumination, and the like, increase. The devices and methods of the instant invention address some of these issues.

The position on the detector upon which a given signal is incident is indicative of (1) the originating ZMW in the array, and (2) the emission characteristics of the signal component, which is used, for example, to identify the type of fluorescently labeled nucleotide analog incorporated in an extension reaction. As noted above, the detector may include in some cases multiple sensing elements, each for detecting light having a different color spectrum. For example, in the case of sequencing, the sensor for each reaction cell may have 4 elements, one for each of the four bases. In some cases, the sensor elements provide color discrimination, in other cases, color filters are used to direct the appropriate color of light to the appropriate sensor element. In some cases, the sensor elements detect intensity of signal only, without discriminating color. In some cases, the sensor elements identifies the incorporated nucleotide using a combination of emission characteristics.

Optical Waveguides

As mentioned above, the analytical devices of the instant invention, in some embodiments, comprise an optical waveguide to deliver excitation energy to a sample. For example, as shown in FIG. 5, optical waveguide 506 conveys excitation light to the reaction region/well 502, where the evanescent field emanating from the waveguide 506 illuminates reactants within the reaction region 502. The use of an optical waveguide to deliver excitation illumination is advantageous for numerous reasons. For example, because the illumination light is applied in a spatially focused manner, e.g., confined in at least one lateral and one orthogonal dimension, using efficient optical systems, e.g., fiber optics, waveguides, multilayer dielectric stacks (e.g., dielectric reflectors), etc., the approach provides an efficient use of illumination (e.g., laser) power. For example, illumination of a substrate comprising many separate reaction sites, "detection regions," or "observation regions" using waveguide arrays as described herein can reduce the illumination power ~10- to 1000-fold as compared to illumination of the same substrate using a free space illumination scheme comprising, for example, separate illumination (e.g., via laser beams) of each reaction site. In general, the higher the multiplex (i.e., the more surface regions to be illuminated on the substrate), the greater the potential energy savings offered by the waveguide illumination schemes provided herein. In addition, since waveguide illumination need not pass through a free space optical train prior to reaching the surface region to be illuminated, the illumination power can be further reduced.

In addition, because illumination is provided from within confined regions of the substrate itself (e.g., optical waveguides), issues of illumination of background or non-relevant regions, e.g., illumination of non-relevant materials in solutions, autofluorescence of substrates, and/or other materials, reflection of illumination radiation, etc., are substantially reduced.

In addition to mitigating autofluorescence of substrate materials, the systems described herein substantially mitigate autofluorescence associated with the optical train. In particular, in typical fluorescence spectroscopy, excitation light is directed at a reaction of interest through at least a portion of the same optical train used to collect signal fluorescence, e.g., the objective and other optical train components. As such, autofluorescence of such components will contribute to the detected fluorescence level and can provide signal noise in the overall detection. Because the systems provided herein direct excitation light into the substrate through a different path, e.g., through an optical fiber optically coupled to the waveguide in the substrate, this source of autofluorescence is eliminated.

Waveguide-mediated illumination is also advantageous with respect to alignment of illumination light with surface regions to be illuminated. In particular, substrate-based analytical systems, and particularly those that rely upon fluorescent or fluorogenic signals for the monitoring of reactions, typically employ illumination schemes whereby each analyte region must be illuminated by optical energy of an appropriate wavelength, e.g., excitation illumination. While bathing or flooding the substrate with excitation illumination serves to illuminate large numbers of discrete regions, such illumination may suffer from the myriad complications described above. To address those issues, targeted excitation illumination may serve to selectively direct separate beams of excitation illumination to individual reaction regions or groups of reaction regions, e.g. using waveguide arrays. When a plurality, e.g., hundreds or thousands, of analyte regions are disposed upon a substrate, alignment of a separate illumination beam with each analyte region becomes technically more challenging and the risk of misalignment of the beams and analyte regions increases. Alignment of the illumination sources and analyte regions may be built into the system, however, by integration of the illumination pattern and reaction regions into the same component of the system, e.g., a waveguide substrate. In some cases, optical waveguides may be fabricated into a substrate at defined regions of the substrate, and analyte regions are disposed upon the area(s) of the substrate occupied by the waveguides.

Finally, substrates used in the waveguides may be provided from rugged materials, e.g., silicon, glass, quartz or polymeric or inorganic materials that have demonstrated longevity in harsh environments, e.g., extremes of cold, heat, chemical compositions, e.g., high salt, acidic or basic environments, vacuum and zero gravity. As such, they provide rugged capabilities for a wide range of applications.

Waveguide substrates used in the devices and methods of the present invention generally include a matrix, e.g., a silica-based matrix, such as silicon, glass, quartz or the like, polymeric matrix, ceramic matrix, or other solid organic or inorganic material conventionally employed in the fabrication of waveguide substrates, and one or more waveguides disposed upon or within the matrix, where the waveguides are configured to be optically coupled to an optical energy source, e.g., a laser. Such waveguides may be in various conformations, including but not limited to planar waveguides and channel waveguides. Some preferred embodiments of the waveguides comprise an array of two or more waveguides, e.g., discrete channel waveguides, and such waveguides are also referred to herein as waveguide arrays. Further, channel waveguides can have different cross-sectional dimensions and shapes, e.g., rectangular, circular, oval, lobed, and the like; and in certain embodiments, different conformations of waveguides, e.g., channel and/or planar, can be present in a single waveguide substrate.

In typical embodiments, a waveguide comprises an optical core and a waveguide cladding adjacent to the optical core, where the optical core has a refractive index sufficiently higher than the refractive index of the waveguide cladding to promote containment and propagation of optical energy through the core. In general, the waveguide cladding refers to a portion of the substrate that is adjacent to and partially, substantially, or completely surrounds the optical core. The waveguide cladding layer can extend throughout the matrix, or the matrix may comprise further "non-cladding" layers. A "substrate-enclosed" waveguide or region thereof is entirely surrounded by a non-cladding layer of matrix; a "surface-exposed" waveguide or region thereof has at least a portion of the waveguide cladding exposed on a surface of the substrate; and a "core-exposed" waveguide or region thereof has at least a portion of the core exposed on a surface of the substrate. Further, a waveguide array can comprise discrete waveguides in various conformations, including but not limited to, parallel, perpendicular, convergent, divergent, entirely separate, branched, end-joined, serpentine, and combinations thereof.

A surface or surface region of a waveguide substrate is generally a portion of the substrate in contact with the space surrounding the substrate, and such space may be fluid-filled, e.g., an analytical reaction mixture containing various reaction components. In certain preferred embodiments, substrate surfaces are provided in apertures that descend into the substrate, and optionally into the waveguide cladding and/or the optical core. In certain preferred embodiments, such apertures are very small, e.g., having dimensions on the micrometer or nanometer scale, as described further below.

It is an object of devices and methods of the invention to illuminate analytes (e.g., reaction components) of interest and to detect signal emitted from such analytes, e.g., by excitation and emission from a fluorescent label on the analyte. Of particular interest is the ability to monitor single analytical reactions in real time during the course of the reaction, e.g., a single enzyme or enzyme complex catalyzing a reaction of interest. The waveguides described herein provide illumination via an evanescent field produced by the escape of optical energy from the optical core. The evanescent field is the optical energy field that decays exponentially as a function of distance from the waveguide surface when optical energy passes through the waveguide. As such, in order for an analyte of interest to be illuminated by the waveguide, it must be disposed near enough to the optical core to be exposed to the evanescent field. In preferred embodiments, such analytes are immobilized, directly or indirectly, on a surface of the waveguide substrate. For example, immobilization can take place on a surface-exposed waveguide, or within an aperture in the substrate. In some preferred aspects, analyte regions are disposed in apertures that extend through the substrate to bring the analyte regions closer to the optical core. Such apertures may extend through a waveguide cladding surrounding the optical core, or may extend into the core of the waveguide. In certain embodiments, such apertures also extend through a mask layer above the surface of the substrate. In preferred embodiments, such apertures are "nanoholes," which are nanometer-scale holes or wells that provide structural confinement of analytic materials of interest within a nanometer-scale diameter, e.g., ~10-100 nm. In some embodiments, such apertures comprise optical confinement characteristics, such as zero-mode waveguides, which are also nanometer-scale apertures and are further described elsewhere herein. Although primarily described herein in terms of channel waveguides, such apertures could also be constructed on a planar waveguide substrate, e.g., where the planar waveguide portion/layer is buried within the substrate, i.e., is not surface-exposed. Regions on the surface of a waveguide substrate that are used for illumination of analytes are generally termed "analyte regions", "reaction regions", or "reaction sites", and are preferably located on a surface of the substrate near enough to an optical core to be illuminated by an evanescent wave emanating from the optical core, e.g., on a surface-exposed waveguide or at the bottom of an aperture that extends into the substrate, e.g., into the waveguide cladding or core. The three-dimensional volume at a reaction site that is illuminated by the evanescent field of a waveguide core (e.g., to an extent capable of allowing detection of an analyte of interest) is generally termed the "observation volume" or "illumination volume". A region of a waveguide substrate that comprises one or more analyte regions is generally referred to as a "detection region" of the substrate, and a single substrate may have one or multiple detection regions. Examples of such optical waveguides are provided in U.S. Pat. No. 7,820,983 and U.S. Patent Application Publication No. 2012/0085894, as described above.

The present invention provides devices for waveguide-based illumination of analyte regions in apertures (e.g., nanoholes or ZMWs) that in some cases reduce the variation in illumination, for example, by mitigating propagation losses over the length of the waveguide. Such propagation losses can be further exacerbated by a metal layer disposed over the surface of the substrate, because it can absorb optical energy from a surface-exposed or core-exposed waveguide, or even a waveguide near to the surface of the substrate. Such metal layers are typically found in conventional ZMW arrays, presenting a challenge for combining such arrays with waveguide illumination strategies.

One of the limitations of waveguide illumination is optical attenuation as the light propagates down the guide resulting in a reduction in power at different locations in the guide. For example, a particular laser intensity coupled into the waveguide will experience a slow decrease in energy density as light travels down the guide due to propagation losses, with the highest power at the end nearest the illumination source and the lowest at the end farthest from the illumination source. The degree of the propagation loss is typically a function of the designed geometry and manufacturing tolerances, and presents a challenge to performing multiplexed analytical reactions because it constrains the spatial range of the usable waveguide structure. It is important to maximize the distance over which the laser intensity is sufficiently uniform, in order to maximize the multiplex capabilities of the system. It is therefore an object of the present invention to provide uniform power over the length of a waveguide, e.g., to promote uniform illumination of all reaction sites to be illuminated by the waveguide.

In this context, it should be understood that light may be propagated from either direction within a waveguide, and that propagation of light from each end of a waveguide simultaneously may in some circumstances help to mitigate propagation losses within the waveguide. In some circumstances it may be advantageous to propagate light from each end of a waveguide sequentially, rather than simultaneously, as would be understood by those of ordinary skill in the art.

In certain embodiments, a waveguide is tapered such that the core gradually becomes thinner along the direction of propagation. This causes the degree of light confinement to be gradually increased, which can offset the gradual reduction in the total amount of power in the guide due to propagation losses and essentially maintain a desired mode shape and field strength for the optical energy propagated over the length of the waveguide core. In principle, the sum of propagation losses is balanced by the decreasing core size such that uniformity of evanescent field strength can be held constant for an arbitrarily long distance, with limitations to the strength of the evanescent field also being dependent on the starting laser power and the starting waveguide core dimensions. For a given waveguide substrate, once the propagation loss is determined the waveguide geometry can be designed to smoothly vary, thereby modifying the degree of confinement such that the relative field strength at the point of interest increases at the same rate that propagation losses reduce the total power in the guide. For example, a tapered waveguide core can be widest at the portion most proximal to the light source, slowly narrowing along the guide, with the field localization increasing at the same rate that propagation losses are reducing the waveguide field strength. The tapering can take place in any direction including the z direction (top to bottom), the y direction (side to side), or a combination thereof.

In certain embodiments, a waveguide cladding above a waveguide core in a waveguide substrate is tapered such that the waveguide core is slowly brought closer to the reaction sites at the surface of the substrate by an ever-decreasing width of the waveguide cladding layer that separates the core from the reaction sites. As such, although there is propagation loss from the waveguide, as the field strength in the waveguide decreases, it is brought closer to the reaction sites, and this increasing proximity compensates for an overall reduced field strength. In some embodiments, both the waveguide cladding layer and waveguide core are tapered to mitigate loss of field strength due to propagation losses.

Local Field Enhancement

In certain embodiments, the waveguides used in some of the devices disclosed herein comprise a specific feature associated with each aperture, a local field enhancement element, to increase the efficiency of sample illumination. Such a feature serves to improve the coupling efficiency between the waveguide and the illumination volume, particularly when the apertures are subwavelength apertures in a metal layer disposed over the surface of the substrate. For example, in some embodiments, the local field enhancement element is a layer of a material in the vicinity of each aperture that has a higher dielectric constant than the cladding layer or that is a metal, such as, for example, copper, silver, gold, or aluminum. One example of this type of local field enhancement element is shown in FIG. 7A, where the local field enhancement element corresponds to a ring or other geometric pattern of high dielectric material or metal 706 surrounding the aperture 702, just below the opaque, metal layer 704. As shown in FIG. 7A, a pattern of high dielectric material, such as $Al_2O_3$, or a metal, couples energy from the waveguide core of high refractive index 708, such as $Si_3N_4$, through the cladding of low refractive index 710, such as $SiO_2$. Other suitable materials of high dielectric material may be substituted for $Al_2O_3$, as would be understood by those of ordinary skill in the art.

The material of high dielectric or metal surrounding the aperture may serve other purposes in addition to improving the coupling of excitation light to the illuminated volume within the aperture. For example, if this material is deposited such that it is exposed to the solution to be analyzed, it may act as a distinct surface for immobilization of biomaterials or to prevent immobilization of those materials. Specifically, there may be advantages in providing different surfaces on the bottom and sides of the aperture to allow, for example, for biased immobilization of reaction components. See, e.g., U.S. Patent Publication No. 2012/0085894. For example, as shown in FIG. 7A, the sides of the nanowell/aperture may expose a material such as, e.g., the high dielectric material or the metal, whereas the bottom of the nanowell/aperture may expose the cladding material, e.g., glass. Selective deposition of analytes is preferably effected when there are chemical differences between the surfaces, as would be understood by those of ordinary skill in the art.

The local field enhancement element may include additional features to further enhance the efficiency of sample illumination by excitation light, to further decrease propagation losses of excitation light, or to provide other functions, such as, for example, enhancing the detection of light emitted from the sample. One such additional feature is exemplified in FIG. 7B, where a pattern of high dielectric material or metal 726 surrounds the nanowell/aperture 722 below the opaque, metal layer 724. These patterns, for example a pattern of concentric rings surrounding the aperture, as shown in FIG. 7B, may act as a broad area coupler for the excitation light into the sample volume. They may additionally act to collimate light emitted from sample in the illuminated volume within the aperture, thus improving the detectability of that light. In this particular embodiment, the local enhancement element thus serves to couple light both into and out of the aperture. Also shown in FIG. 7B is the waveguide core of high refractive index 728, such as $Si_3N_4$, set within the cladding of low refractive index 730, such as $SiO_2$.

Aperture shapes, and the shape of the high dielectric material or metal surrounding the apertures, may additionally enhance the coupling of light energy from the waveguide core to the illuminated volume. See, for example, Sahin et al. (2011) *J. Nanophoton.* 5(1), 051812; doi: 10.1117/1.3599873. Subwavelength aperture shapes, including C-shaped apertures, triangle pairs, or diamond-shaped aperture structures may accordingly be usefully employed as local field enhancement elements according to this aspect of the invention.

Figure 7C:
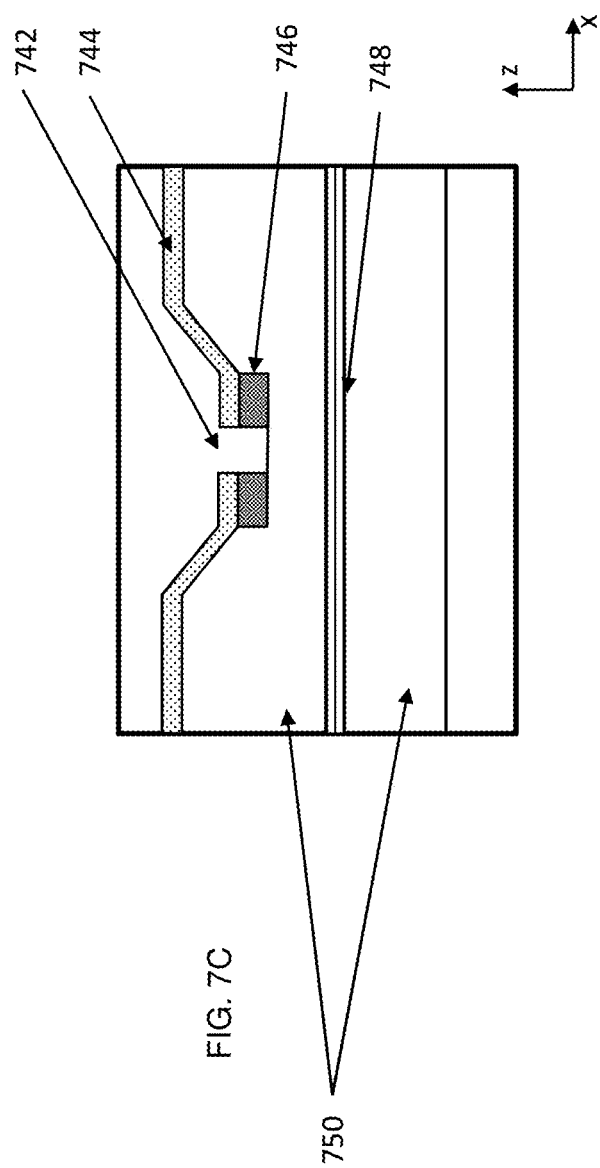
FIG. 7C illustrates another alternative device structure, having a decreased cladding thickness in the regions of the waveguide adjacent to the aperture and/or an increased cladding thickness in the regions not adjacent to the aperture. The device of FIG. 7C additionally includes a high dielectric material or metal in the vicinity of the aperture.

In yet another embodiment, the local field enhancement element corresponds to increasing the thickness of the cladding in the regions of the waveguide that are not adjacent to the aperture and/or decreasing the thickness of the cladding in the regions of the waveguide that are adjacent to the aperture. This embodiment provides, for example, for decreased propagation losses, due to the increased distance between the light beam and the metallic layer, and for increased coupling efficiency, due to the positioning of the aperture closer to the evanescent wave. As shown in FIG. 7C, decreasing the thickness of the cladding 750 (e.g., $SiO_2$) in the region around the aperture 742 by recessing the aperture improves the coupling of light energy into the illumination volume. Increasing the thickness of the cladding in regions remote from the aperture decreases propagation losses resulting from interactions of the evanescent wave with the opaque metallic layer 744. FIG. 7C also shows an additional optional local field enhancement element in the form of a ring of high dielectric material or metal 746 surrounding the aperture below the opaque metallic layer. As noted above, this element can be a ring or other pattern of high dielectric material or metal in the vicinity of the aperture, just below the opaque metallic layer. Combinations of different local field enhancement elements may thus provide synergistic improvements in the coupling of light energy from the waveguide core to the illuminated volume and are considered within the scope of the invention. Also shown in FIG. 7C is the waveguide core of high refractive index 748, such as $Si_3N_4$, set within the cladding of low refractive index 750.

Figure 8A:
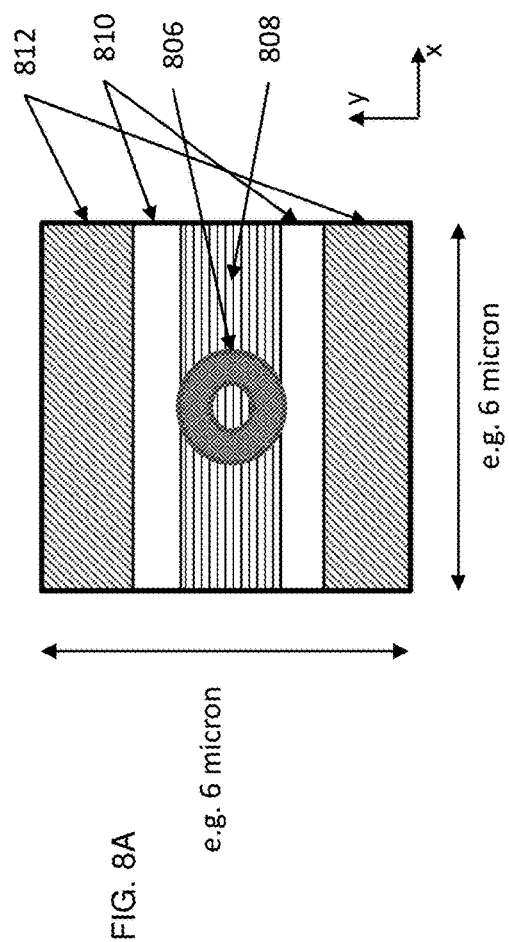
FIGS. 8A-8B illustrate an analytical device where the thickness of the cladding is decreased in the regions of waveguide adjacent to the aperture, and the device additionally contains a stray light termination material.
Figure 8B:
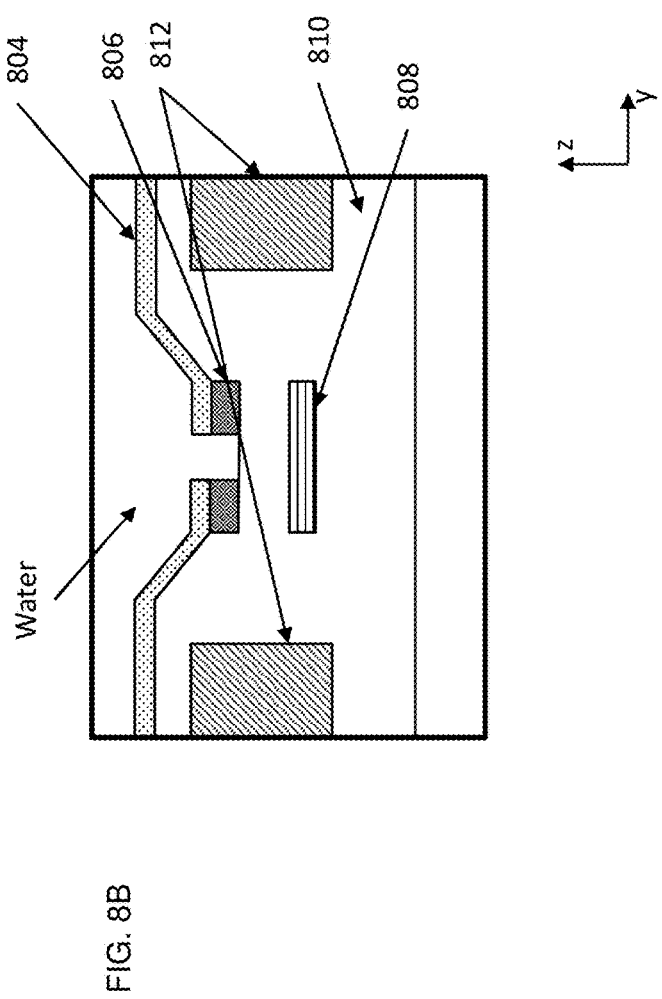

FIGS. 8A and 8B illustrate top-down and cross-sectional views of another embodiment of the analytical device, similar to the device of FIG. 7C, in which the aperture is surrounded by a ring of high dielectric or metal 806 and is recessed to bring it closer to the waveguide core. (Note that the opaque, metallic layer 804 is omitted from the top-down view shown in FIG. 8A.) This embodiment also includes an additional optional feature of this aspect of the invention, a stray-light termination element 812. Such a design feature can decrease background signal by blocking scattered light from the excitation source and potentially also autofluorescence from materials within the device. The material used in the stray-light termination element is selected from materials that selectively absorb light to be blocked from reaching the detector layer of the device, as would be understood by one of ordinary skill in the art. Also shown in FIGS. 8A-8B is the waveguide core of high refractive index 808, such as $Si_3N_4$, set within the cladding of low refractive index 810, such as $SiO_2$. Exemplary dimensions for the device are indicated in FIG. 8A.

FIGS. 9A-9C illustrate a device configuration used in a mathematical simulation of the effectiveness of the above designs, specifically increasing the cladding thickness in regions not adjacent to the aperture and including a ring of metal 906 in the vicinity of the aperture. (Note that the opaque, metallic layer 904 is omitted from the top-down view shown in FIG. 9A.) In particular, the simulations involve a finite-difference time-domain (FDTD) solution of the Maxwell equations. See Taflove and Hagness (2004) *Computational Electrodynamics: The Finite-Difference Time-Domain Method, Third Edition*. FIGS. 9A-9C also show the waveguide core of high refractive index 908, such as $Si_3N_4$, set within the cladding of low refractive index 910, such as $SiO_2$.

The simulations using the device configuration of FIGS. 9A-9C demonstrate that by increasing the cladding thickness between ZMWs by 200 nm, the propagation loss, for example, due to proximity to the metallic layer, decreases from over 100 dB/mm to ~14 dB/mm, allowing a lower laser power to illuminate several ZMWs. Overall illumination efficiency of the fluorophore is kept high, so as to keep the total laser power in the waveguide low, thus helping to limit autofluorescence generated in the waveguide. In addition, a metal ring (or cylindrical shell) in the vicinity of the aperture provides enough metal to enhance the coupling to the ZMW but not so much as to create waveguide loss. While any metal could be used, metals such as copper, silver, gold, and aluminum are preferred. Typical metal thicknesses (i.e., shell thickness) around the aperture are 100-400 nm. Since aperture diameters are preferably in the range of 100-200 nm, and most preferably approximately 140 nm, the outer diameter of the metal ring is therefore preferably from 340 nm to 1 µm, although outer ring diameters of from about 0.2 to 2 µm, or even higher, are contemplated.

Dimensional Modulation of Waveguides

As noted above, efficient coupling of excitation light into the illumination volume requires that the optical waveguide be sufficiently close to the nanometer-scaled apertures, but placement of the optical waveguide too close to the metallic layer in which the apertures are disposed may cause propagation losses. In order to overcome these limitations, in another aspect of the invention, the optical waveguide is placed sufficiently far from the metallic layer to avoid propagation losses, and the cross-sectional area of the waveguide is modulated in the vicinity of the apertures to enlarge the mode size and thus increase the coupling of light into the illuminated volume. In general, waveguide core dimensions are designed to satisfy the single-mode condition, as well as confining the mode compactly around the core region. In preferred embodiments, the cross-sectional area of the optical core is decreased at locations where the optical waveguide illuminates the apertures. In some embodiments, the decrease in cross-sectional area of the optical core is achieved using adiabatic tapers in order to avoid extra power loss. In preferred embodiments, and as illustrated in FIGS. 10A and 10B, the thickness of the optical waveguide is kept constant, while the cross-sectional area of the optical core is modulated by varying the width of the optical core. Specifically, FIG. 10A provides a top-down view of waveguide 1008 with cross-sectional views of a normal section of the waveguide with compact mode size (left cross-section) and a tapered-down section of the waveguide with expanded mode size (right cross-section). FIG. 10B provides a three-dimensional perspective of the exemplary device showing locations of nanowell/apertures 1002 within the opaque, metal layer 1004 covering the array. Also shown are dimension-modulated waveguides 1008 positioned below the nanowell/apertures. Fabrication of the core layer in this embodiment is simplified, because the core thickness is uniform. In some embodiments, the optical signal passing through the waveguide core is transverse electric (TE) polarized light. These embodiments provide advantages when the cross-sectional area of the waveguide is modulated by varying the width of the waveguide core, because the mode size of TE-polarized light is most strongly affected by the waveguide width.

In variants of the just-described aspect of the invention, the width of the optical waveguide is kept constant, while the cross-sectional area of the optical core, and thus the mode size of the transmitted light, is modulated by varying the thickness of the optical core. As above, the cross-sectional area of the optical core is decreased at locations where the optical waveguide illuminates the apertures in order to maximize coupling to the illuminated volume. In some embodiments, the optical signal passing through the waveguide core is transverse magnetic (TM) polarized light, since the mode size of TM-polarized light is most strongly affected by the waveguide thickness, as would be understood by one of ordinary skill in the art.

In some embodiments of the invention, dimensional modulation of the waveguides and local field enhancements may be usefully combined. For example, modulation of the cross-sectional area of the optical core at each aperture may be usefully combined with a pattern of high dielectric material or metal in the vicinity of each aperture, for example, below the metallic layer. Such combinations provide yet further improvement in the efficiency of coupling of optical energy from the waveguide to the illuminated volume.

By way of non-limiting example, the typical waveguide widths for use in the analytical devices of the instant invention range from 100 nm to 1000 nm. Such widths therefore correspond to roughly 0.3 to 3.0 wavelengths in a situation where the wavelength of excitation light propagated along the waveguide is 335 nm. (It should be noted that the wavelength of photons in a waveguide may be significantly shifted from that of the same photons traveling through air.) In some embodiments of the invention, the width of the waveguide optical core is decreased by 5 to 90% at locations where the evanescent field illuminates the nanometer-scale apertures, compared to locations where the evanescent field does not illuminate the apertures (in other words, the optical core is decreased from 0.15 wavelengths to 2.7 wavelengths for a core that is 3.0 wavelengths wide). In some embodiments, the width of the waveguide optical core is decreased by 5 to 50% at locations where the evanescent field illuminates the apertures, compared to locations where the evanescent field does not illuminate the apertures (i.e., from 0.15 wavelengths to 1.5 wavelengths in a 3.0 wavelength wide core). In preferred embodiments, the width of the waveguide optical core is decreased by 10 to 20% at those locations (i.e., from 0.30 wavelengths to 0.60 wavelengths). As noted above, it is desirable in the devices of this aspect of the invention for the changes in width/cross-sectional area to be gradual, preferably adiabatic, in order to avoid an additional mechanism for propagation losses. Such gradual tapering—narrower in the locations near the nanometer-scale apertures and wider in the locations away from the nanometer-scale apertures—can be readily be optimized in the design of the device, using analytical calculations, as would be understood by one of ordinary skill in the art.

Waveguide Core Positioning

In another aspect of the invention, the configuration and positioning of the waveguide core is varied in order to maximize collection of signal photons while suppressing collection of background photons (e.g., scattered light and autofluorescence). In particular, in these embodiments the waveguide core is positioned so that it is not directly between the nanometer-scaled apertures and their corresponding detectors. In preferred embodiments, the illuminated volume in each aperture is illuminated by evanescent fields emanating from two or more optical cores. In some embodiments, the device further contains an opaque layer disposed between the waveguide layer and the detector layer. The opaque layer contains a plurality of openings positioned to allow signal photons from the sample to pass unimpeded into the detector. The opaque layer would thus decrease access of photons from, for example, autofluorescence or scattering emanating from the waveguide cores, to the detector, and thus decrease background signal. As would be understood by one of ordinary skill in the art, signal photon collection is defined by photon flux through the opening in the opaque material, and collection efficiency is modulated by the dimensions of the opening and the optical distance from the signal source. Likewise, collection of autofluorescence and scattered light from the waveguide core through the opening is governed by the dimensions of the opening and the solid angle occupied by the waveguide as viewed from the opening.

By using a waveguide that is not positioned directly between the nanometer-scaled aperture and the detector, i.e., a "slot" waveguide, the waveguide core, and associated autofluorescence and scattering, is moved away from a direct path to the detector, thus increasing the angle of incidence into the detector and decreasing background signal. Furthermore, slot waveguides may provide increased optical fields in the regions of low refractive index between the high-index cores, and thus increase coupling of optical energy from the waveguides to the illuminated volume. See, for example, Feng et al. (2006) IEEE J. Quantum Electron. 42, 885; Sun et al. (2007) Optics Express 15, 17967. Optical sensing devices making use of slot waveguides have been described. See, for example, Barrios (2006) IEEE Photon Technol. Lett. 18, 2419; Barrios et al. (2007) Optics Letters 32, 3080; Barrios et al. (2008) Optics Letters 33, 708; Robinson et al. (2008) Optics Express 16, 4296. The signal-to-background ratio in devices of the instant invention that utilize a slot waveguide format may be optimized, for example, by varying the dimension of the openings in the opaque layer and by varying the configuration of the waveguide (e.g., spacing between separate optical cores and distance between waveguide core, opaque layer, and detector layer), as would be understood by those of ordinary skill in the art.

Figure 11A:
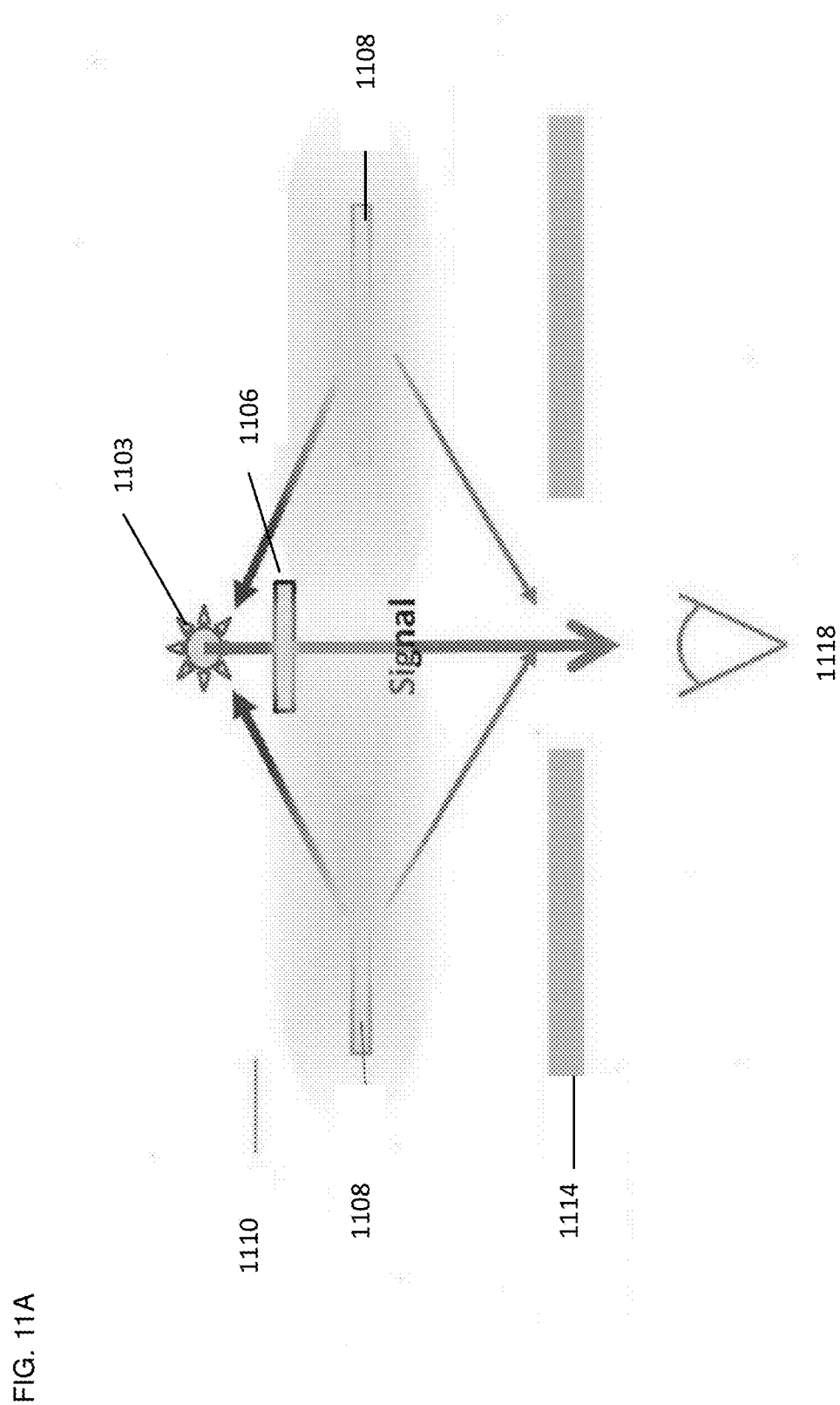
FIGS. 11A-11B illustrate an example of a device with a "slotted" waveguide.
Figure 11B:
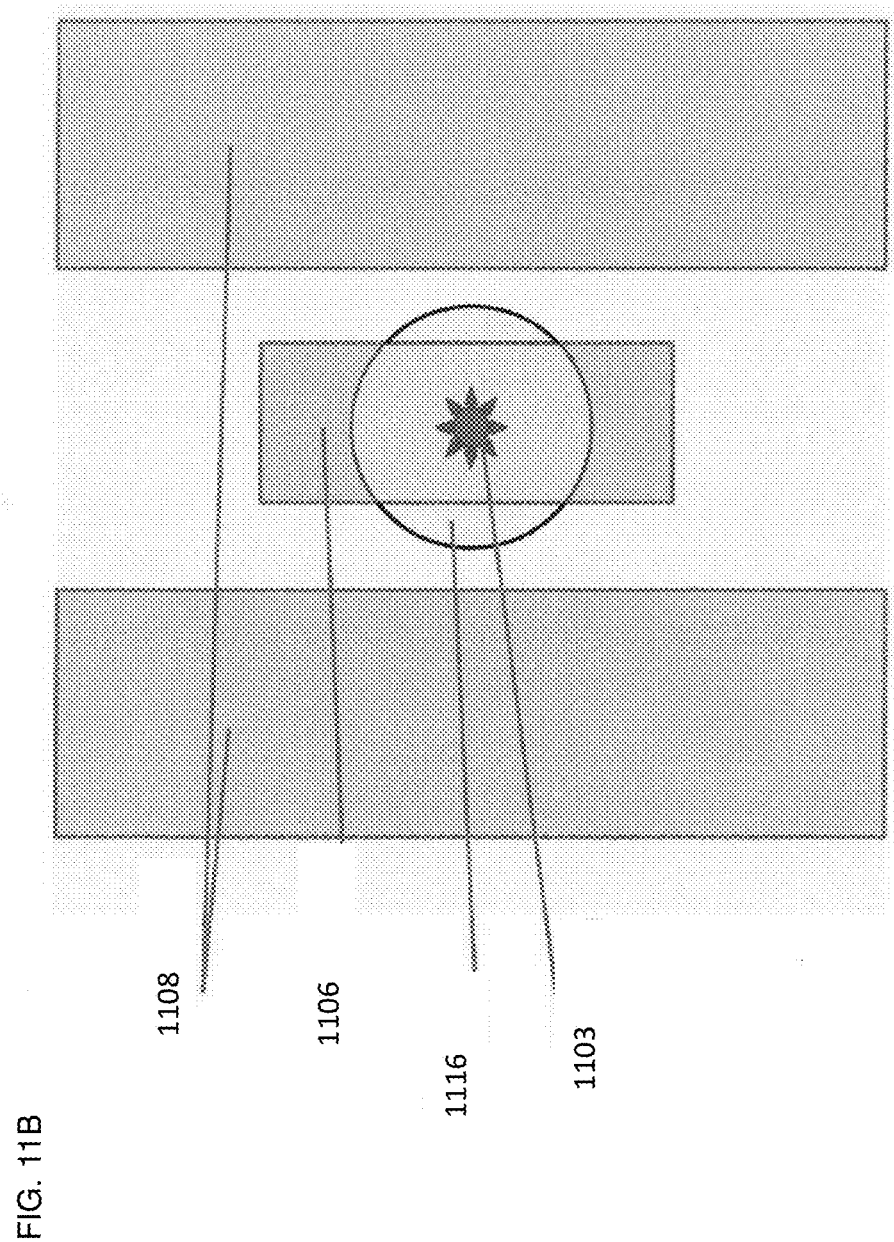

FIGS. 11A-11B illustrate an example of this aspect of the invention that includes an optional local field enhancement element to increase further the coupling of excitation energy to the illuminated volume. In particular, FIG. 11A, illustrates a cross-sectional view of the device down the length of the divided (i.e., "slot") waveguide cores 1108, surrounded by cladding of low refractive index 1110. As shown, the evanescent waves emanating from the separate cores overlap and jointly illuminate the sample "signal source" 1103 within a nanowell/aperture at the top of the drawing. The local field enhancement element 1106 is illustrated in this drawing as a rectangle below the sample. This element could, for example, correspond to a material of high dielectric constant or metal patterned in the area adjacent to the nanometer-scale apertures, as described above. As also described more fully above, this element serves to increase coupling between the waveguide core and the sample within the nanometer-scale apertures and thus increase signal emission from the sample. Such increased coupling could further increase the signal-to-background ratio in the devices of the invention by decreasing the size of the field necessary in the core and thus decreasing the associated autofluoresence and scattering.

FIG. 11A further illustrates the opaque layer 1114, which is positioned between the waveguide layer and the detector 1118, and the opening in the opaque layer to allow emission signal from the illuminated volume to pass to the detector. The opaque layer is fabricated from any material suitable for attenuating transmission of excited light from the waveguide core to the detector, e.g., a metal layer of sufficient thickness. As shown in FIG. 11A, the positioning of the waveguide cores away from a direct alignment between the nanometer-scale aperture (not shown, but surrounding the illuminated sample volume) and the detector does not greatly diminish the efficiency of excitation of the illuminated volume, particularly if an optional local enhancement element is included to enhance the coupling, but causes a significant decrease in the transmission of autofluorescence or scattered light to the detector, due to the presence of the opaque layer.

FIG. 11B provides a top-down view of the analytical device shown in FIG. 11A, including the divided waveguide cores 1108. The "signal source" 1103, which corresponds to the illuminated volume of the sample is above the plane of the drawing, and the opaque layer, including the "opening" 1116 in the opaque layer over the detector is below the plane of the drawing. The local enhancement element 1106 is illustrated as a rectangular block, but any of the local enhancement elements described above could usefully be included in the device to enhance coupling of excitation energy to the sample volume. The detector is not shown in this drawing but would be positioned below the opening and in line with the signal source.

Waveguide Frequency Conversion

As noted above, excitation light is typically provided to sample volumes via guided optics. Part of the motivation for this approach lies in the possibility of dispensing with the disadvantages of classic free-space optics by directing the sum total of excitation light needed to excite the illumination volumes in all of the nanometer-scale apertures through a single optical system and onto a single chip. The guided optical approach can involve some disadvantages of its own, however, including alignment complexity, cumulative autofluorescence, scattering, and cumulative laser heating. The latter three issues in particular are straightforward limitations that result from the material properties of the optical system. The traditional chemistry and chemical formulations used in fluorescence-based nucleic acid sequencing contribute to the difficulties, as photonic excitation must be delivered within a fairly narrow range of wavelengths, and the resulting emission wavelengths are only slightly longer. Consequently, autofluorescence of the system generally occurs within the same region of the spectrum as the desired fluorescence emission signals and can therefore be a significant limitation on the optical signal-to-noise ratio that can be achieved in a given system. Scattering can also be a detriment to signal-to-noise, because it is difficult to control the direction that scattered light travels as it leaves the guided mode, and some fraction may arrive at a sensor, adding noise. Such scattered light may be difficult to filter out based on its wavelength. Similarly, photonic heating caused by non-negligible absorption of the materials used to construct the optical system and the sample chip is a strong function of the excitation wavelength, and there is little flexibility in altering this parameter given the limitations in reagents used in typical sequencing reactions.

Accordingly, in another aspect of the invention, the limitations of a typical multiplexed sequencing system are addressed by using optical techniques such as harmonic generation, four-wave mixing, and stimulated raman scattering to manipulate the wavelengths of pump excitation away from those necessary for sample illumination and detection and toward spectral regions that are more suitable for the optical system, particularly with respect to the effects of the excitation photons on autofluorescence, laser heating, propagation loss, signal-to-background ratios, etc. Specifically, it is generally beneficial for excitation light to be transported as longer-wavelength photons, for example as infrared photons, which generate less autofluorescence within the device and which result in less laser heating. Shorter-wavelength light can be generated at predetermined locations, as desired, preferably only in the locations necessary to excite the relevant samples. Waveguide frequency conversion can be effected by only slight modifications in optical parameters through phase matching, or it can be actively switched on and off through electro-optical effects that modify the refractive index of one or more materials.

Thus, light can be transported as an infrared pump and then be efficiently coupled into shorter wavelength harmonic waveguide modes as desired. An additional advantage of such delivery of waveguide light is that scattering of light is dramatically reduced, because the infrared pump wavelength is significantly different in wavelength from the signal being collected by the detector, thereby reducing the detrimental impact of scattering on the signal-to-noise ratio.

Wavelength conversion in waveguides is typically effected through second harmonic generation (SHG), wherein efficient conversion involves three features: a nonlinear optical (NLO) material (in the case of SHG, for example, a noncentrosymmetric material that responds to electromagnetic fields with higher polarization multipoles), phase matching (typically with equal group velocities on both propagating modes), and sufficient overlap integral (for example, where the energy density overlaps between the fundamental mode, the harmonic mode, and the nonlinear material in the structure). All three features can be designed into a waveguide structure, and all three can be selected or adjusted by a variety of techniques that are well understood by those of ordinary skill in the art. Furthermore, the techniques are widely available and are already being used in numerous commercial applications. In addition to SHG, similar techniques have been applied to other nonlinear optical interactions including optical parametric amplification (OPA) and stimulated Raman scattering. Such alternative approaches should also be considered within the scope of the instant invention.

At a fundamental level, periodic poling may be used to determine where light is converted from longer wavelengths, for example infrared wavelengths, to wavelengths usefully utilized in the direct excitation of samples, for example visible wavelengths. Such periodic poling may be divided generally into two branches, a fixed periodic poling, which would not change in time, and a dynamic periodic poling, which can be used to fine-tune the wavelength conversion and to switch on or off the conversion at any location or set of locations, and at any time. The programmability of such approaches is of particular value in the application of periodic poling to wavelength conversion for use in the sequencing methods described herein. Application of these techniques, including, for example, materials used, methods of fabrication, optical properties, theoretical principles, methods of tuning, conversion efficiencies, and so forth, are known in the art. See, for example, Yao and Wang, *Quasi-Phase-Matching Technology*, in *Nonlinear Optics and Solid-State Lasers*, Springer Series in Optical Sciences 164, Springer-Verlag Berlin Heidelberg 2012. Specific examples of the use of fixed and dynamic periodic poling in wavelength conversion devices have also been reported. See Laurell et al. (2012) *Optics Express* 20, 22308; Chen et al. (2012) *Optics Letters* 37, 2814; Nava et al. (2010) *Electronics Letters* 46, 1686; Pan et al. (2010) *Optics Communications* 284, 429.

Figure 12A:
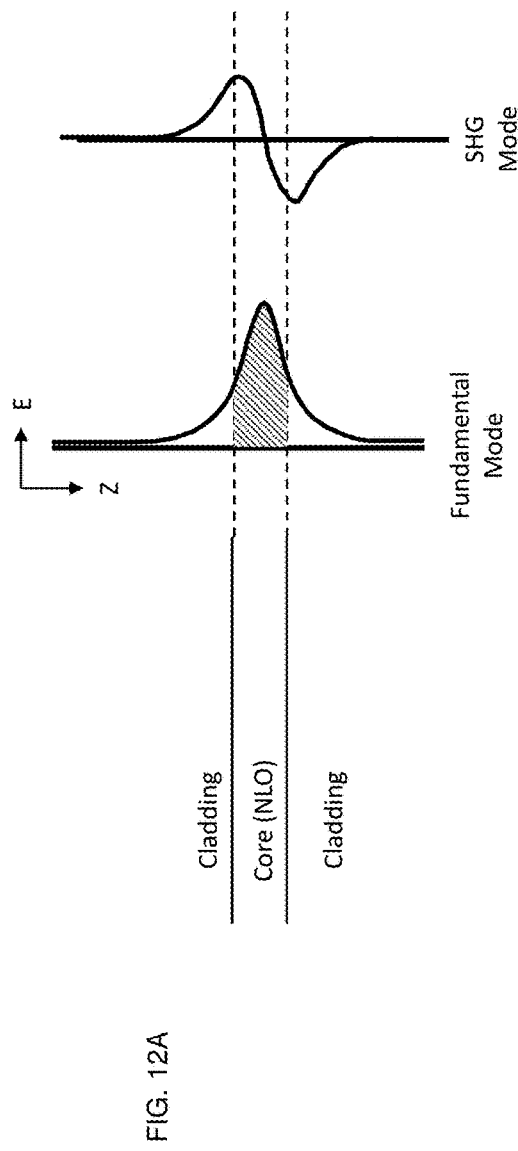
FIGS. 12A-12B show the configuration and optical modes of a waveguide containing a non-linear optical material in the core (FIG. 12A) and in part of the cladding (FIG. 12B).
Figure 12B:
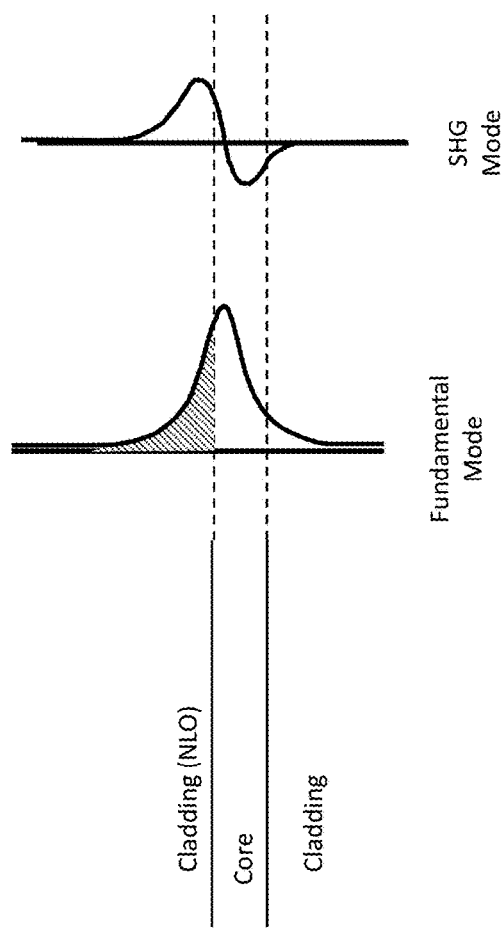

An example of a basic SHG waveguide usefully employed in the devices of the instant invention is illustrated in FIG. 12A, where the nonlinear medium is present in the core material of the waveguide, thus simplifying the overlap integral. An alternative structure, wherein the nonlinear medium is present in part of the cladding material, is shown in FIG. 12B.

Figure 13A:
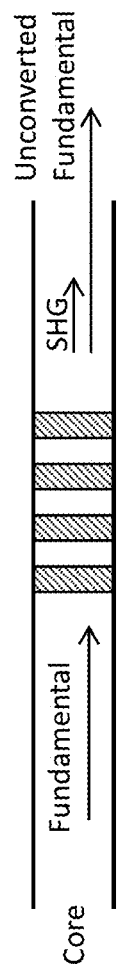
FIGS. 13A-13B illustrate configurations of waveguides containing non-linear optical materials.
Figure 13B:
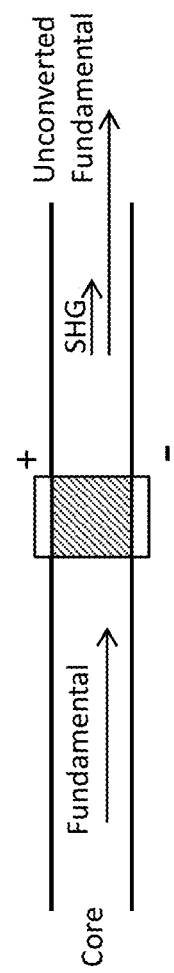

FIG. 13A illustrates phase matching by periodic NLO materials. Such an approach can allow significantly relaxed fabrication tolerances compared to situations where phase matching is not provided by such periodicity. FIG. 13B illustrates phase modulation by electro-optic effects. It should be noted in this context that virtually all SHG materials also exhibit the strong Pockels coefficients that are important for this electro-optical effect.

The approaches for waveguide frequency conversion described herein can be incorporated into the architecture of an analytical device in a variety of ways. For example, as shown in FIG. 14A, SHG conversion may take place just after light is coupled into the chip. Alternatively, or in addition, excitation light may be injected into the waveguide and converted into SHG at predetermined locations, as shown in FIG. 14B. In some embodiments, excitation light can be programmed such that different regions of nanometer-scale apertures and their corresponding illuminated volumes can be switched on and off independently.

Integrated Illumination

As described above, the analytical devices disclosed herein may be used to monitor single molecule real time sequencing reactions, wherein a template/polymerase primer complex is provided, typically immobilized, within an optically confined region, such as within a nanometer-scale aperture, e.g., a ZMW, nanohole, or "nanowell", or proximal to the surface of a transparent substrate. The optically confined region is illuminated with an excitation radiation appropriate for the fluorescently-labeled nucleotides that are to be used. Because the complex is within an optically confined region, or very small illumination volume, only the reaction volume immediately surrounding the complex is subjected to the excitation radiation.

Although the integrated analytical devices of the instant invention include, in some aspects, waveguides to provide the necessary illumination for monitoring these reactions from an external source, in another aspect, the source of illumination may, alternatively, or in addition, be provided by one or more illumination elements integrated directly into the device, such that the integrated illumination element optically excites a single nanowell or a subset of nanowells, either directly or in combination with a lateral waveguide. Such integrated illumination elements are generally useful for interrogating single molecule events, as they may break adverse scaling behavior or performance in highly multiplexed systems and may thus allow millions, or even more, of simultaneous measurements to be made.

In one aspect, the disclosure provides analytical devices containing one or more optical resonators, e.g., lasers, that are integrated directly into a waveguide disposed within the substrate of the device. Nanowells containing samples of interest may be disposed on the surface of the substrate, i.e., in a layer of the device above the layer of the device in which the waveguide is disposed, such that evanescent illumination emanating from the waveguide is optically coupled to the nanowells, thus exciting the sample. An optical resonator of the integrated illumination element may be positioned so that the evanescent illumination emanating from the resonator is coupled to one or more nanowells in a region directly adjacent to the resonator (see, e.g., FIGS. 15A and 15B), or the optical resonator may be positioned so that the evanescent illumination is coupled to one or more nanowells in a region remote from the resonator (see, e.g., FIG. 15D). In some embodiments, the optical resonator may be positioned so that evanescent illumination is coupled to one or more nanowells that are directly adjacent to and one or more nanowells that are remote from the resonator (see, e.g., FIG. 15C). In some embodiments, the optical resonator provides illumination to a single nanowell (see, e.g., FIG. 15B), whereas in other embodiments, the optical resonator provides illumination to multiple nanowells (see, e.g., FIGS. 15A, 15C, and 15D).

The optical resonator in this embodiment of an integrated illumination element is preferably fabricated directly into the waveguide within the substrate as the device itself is fabricated. The resonator, or cavity, contains a laser medium (also known as a gain medium) and two flanking mirrors disposed within the waveguide. The laser medium may be chosen from any suitable material, as would be understood by those skilled in the art. For example, crystal materials, typically doped with rare-earth ions (e.g. neodymium, ytterbium, or erbium) or transition metal ions (titanium or chromium) may be used (e.g., yttrium aluminium garnet (YAG), yttrium orthovanadate (YVO4), or sapphire ($Al_2O_3$) lasers). Alternatively, glasses (e.g. silicate or phosphate glasses, doped with laser-active ions), semiconductors (e.g. gallium arsenide (GaAs), indium gallium arsenide (InGaAs), or gallium nitride (GaN)), or even liquids or gases may prove suitable as a laser medium in these devices.

The mirrors of the optical resonator, which may also be referred to herein as reflectors, may also be chosen from any suitable material, as is well-known in the art. The choice of mirror will depend on the particular device configuration. For example, where the optical resonator is coupled to nanowells located in regions adjacent to the resonator, as, for example, those shown in FIGS. 15A and 15B, both of the laser mirrors, typically dielectric mirrors, may be highly reflective mirrors, such as, for example, distributed Bragg reflectors. Such optimized mirrors may have very high reflectivity, in some cases even higher than 99.9999%. For purposes of the instant disclosure, such mirrors may be termed in some situations "100% mirrors" or "100% reflection mirrors", although it should be understood that their reflectivity is not absolute, and indeed, mirrors with less than 100% reflectivity may be suitable for use in the instant optical resonators, depending on the specific requirements.

In some embodiments, the optical resonator will amplify light along the waveguide (see, e.g., FIGS. 15C and 15E) or will insert light into the waveguide such that the nanowells are optically coupled to the integrated illumination element by evanescent illumination emanating from the waveguide in a region remote from the location of the optical resonator (see, e.g., FIG. 15D). It will be understood that the mirrors used in such devices should be chosen according to the properties desired. For example, in embodiments where the optical resonator is used to insert light into the waveguide, for example as shown in FIGS. 15D, 15F, and 15G, one mirror will typically be chosen to be a high reflector (HF) mirror, whereas the other mirror will typically be chosen to be a partial reflector mirror, or output coupler (OC), because it allows some light to leave the laser cavity and enter the waveguide. Mirrors used in optical resonators suitable for amplifying light as it passes along the waveguide, for example, as shown in FIGS. 15C and 15E, are chosen to allow input coupling as well as output coupling. In some embodiments, doped fiber amplifiers may be used to amplify the optical signal along the waveguide. In-line fiber amplifiers are well known in the art of telecommunications.

It should be understood that further variations in the embodiments shown in FIGS. 15A-15G may be constructed without deviating from the scope of this aspect of the invention. For example, combinations of optical amplifiers and non-amplifiers within a waveguide may be usefully employed in the devices, as may be combinations of optical resonators that couple to one or more nanowells directly adjacent to the resonator and one or more nanowells that are remote from the resonator, as would be understood by the skilled artisan.

The gain medium within the optical resonator requires pumping in order to generate light. In some embodiments, the pump may be provided by an optical pump, for example through an opening along one side of the resonator cavity, as shown in FIG. 15F (large arrow). The optical pump may be, for example, flood illumination of an appropriate wavelength. In other embodiments, the pump may be provided electrically, as illustrated in the device of FIG. 15G. The choice of pump will depend on the situation, as would be understood by those of ordinary skill in the art.

In another aspect, the disclosure provides analytical devices that include an integrated illumination element disposed on the surface of the substrate. In other words, the nanowells and the integrated illumination element are disposed in the same layer of the device. In these devices, the integrated illumination element is partly surrounded by an opaque layer or layers, to control and direct transmission of excitation energy into the sample. Non-limiting examples of such devices are illustrated in FIGS. 16A-16G, 17A-17C, 18, 19, and 20. In each of these examples, a DNA polymerase-template complex is shown immobilized to the bottom of a nanowell. The integrated illumination element, which is represented by a large square on the left side of each nanowell, provides excitation energy to the nanowell, either directly from a side of the nanowell or indirectly through a waveguide from the bottom of the nanowell. The excitation energy, which is represented by a thick arrow, is directed into the nanowell through an opening in the opaque layer. The opaque layer, represented by a thick line that partly surrounds the integrated illumination element, may optionally form the sides of the nanowell. Emission energy from labeled nucleotides associated with the DNA polymerase-template complex is transmitted through the transparent substrate below the nanowell, as indicated by the thin arrows. A detector element (not shown) is optically coupled to the nanowell, so as to capture the light emitted from the sample.

It should be understood in the context of this aspect of the invention that the surface of the substrate may in some cases be defined relative to the surface where the reaction complex of interest is immobilized, i.e., the bottom of the nanowell. Accordingly, the integrated illumination element is disposed "in" the substrate in the devices illustrated in FIGS. 15A-15G, whereas the integrated illumination element is disposed "on" the surface of the substrate in the devices illustrated in FIGS. 16A-16G, 17A-17C, 18, 19, and 20.

In some embodiments, the device comprises an illumination element layer, an integrated illumination element, a plurality of illumination volumes, and a plurality of detector elements, wherein the integrated illumination element is disposed in the illumination element layer.

In specific embodiments, the integrated illumination element comprises an optical resonator within a waveguide, the optical resonator comprises a laser medium and a first and a second mirror disposed within the waveguide, and the plurality of illumination volumes are contained in a plurality of nanowells disposed in a layer above the illumination element layer, wherein at least a first nanowell is optically coupled to the waveguide and to one of the detector elements.

In other specific embodiments, the plurality of illumination volumes are contained in a plurality of nanowells disposed in the illumination element layer, the plurality of detector elements are disposed in a layer below the illumination element layer, and the integrated illumination element is partly surrounded by an opaque layer, wherein at least a first nanowell is optically coupled to the integrated illumination element and to one of the detector elements.

Figure 16B:
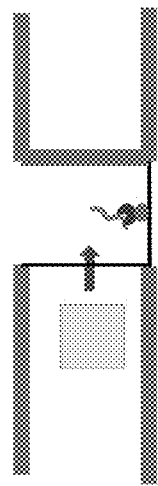
FIGS. 16A-16G illustrate exemplary devices with integrated illumination above the surface of the substrate. The illumination element may be either a waveguide source or a discrete light source, as further described herein. In each case, the illumination element is disposed in the same layer of the device as the nanowells. The opaque layer, as illustrated by thick lines in the drawings, may be a metallic layer.

The placement of the opaque layer or layers around the integrated illumination element controls and directs excitation light to the nanowell. For example, the configuration shown in FIG. 16A allows illumination to enter the nanowell from the lower portion of the nanowell. In some situations, however, it may be advantageous to place the opaque layer only above and below the integrated illumination element, and allow the entire side wall of the nanowell to transmit excitation light, as shown in FIG. 16B. In some embodiments, at least 10%, at least 30%, at least 50%, at least 70%, or even at least 90% of the side wall of the nanowell is covered by the opaque layer. In some embodiments, at least 95%, at least 98%, at least 99%, or even more of the side wall of the nanowell is covered by the opaque layer.

Figure 16D:
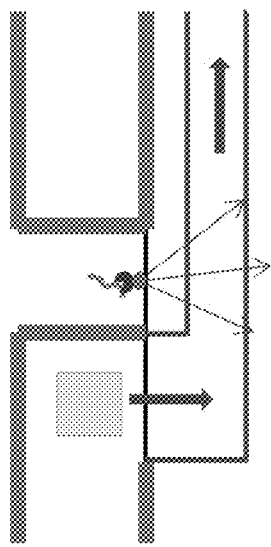
Figure 16A:
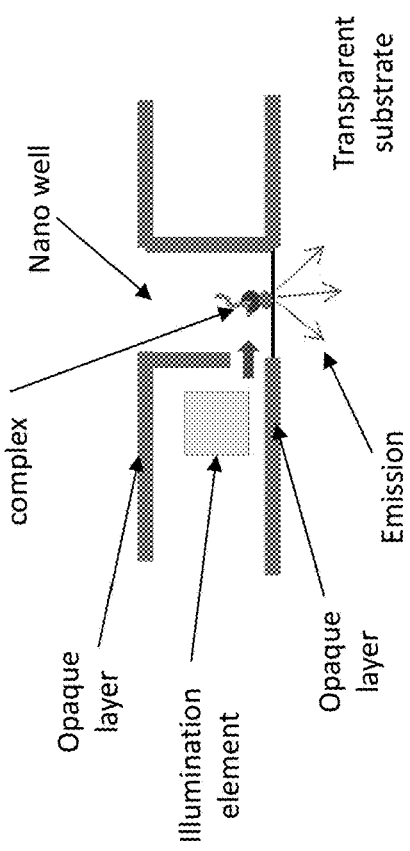
Figure 16C:
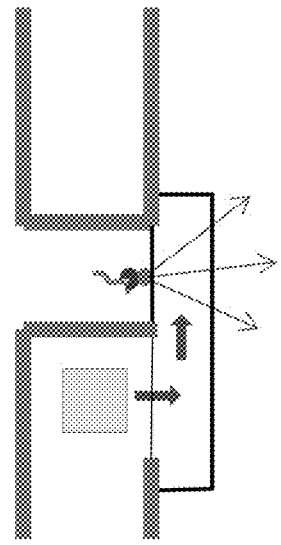

In some embodiments, the devices may further include a transfer waveguide, as shown in FIGS. 16C and 16D. The opaque layer in these embodiments completely covers the side wall of the nanowell but allows excitation light to be coupled through an opening in the opaque layer below the integrated illumination element. The waveguide may, in some embodiments, provide energy to the sample directly by coupling light from the waveguide into the nanowell as shown in FIG. 16C, or the waveguide may provide energy to the sample indirectly, for example by evanescent illumination, as shown in FIG. 16D. The waveguide may, in some embodiments, provide excitation energy to a single nanowell or row of nanowells, or may provide energy to a plurality of nanowells organized in another pattern.

As described above, the dimensions and shape of the nanowell will depend on the desired properties and the nanowell and the methods used to fabricate the device. The depth of the nanowell (i.e., the vertical dimension of the nanowells shown in FIGS. 16A-16G) is typically from 50 nm to 600 nm, but it may in some embodiments be from 100 nm to 500 nm or even from 150 nm to 300 nm. The width of the nanowell (i.e., the horizontal dimension of the nanowells shown in FIGS. 16A-16G) is typically from 50 to 600 nm, but it may in some embodiments be from 100 to 300 nm. The shape of the nanowell (as viewed from the top of the drawings in FIGS. 16A-16G) may be circular, elliptical, square, rectangular, or any other suitable shape. In some cases, the walls of the nanowell may be vertical, as shown for the nanowells of FIGS. 16A-16G, whereas in some cases, the walls of the nanowell may be sloped inward or outward. For example, the nanowells could be cylindrical, cone-shaped, or inverted cone-shaped if so desired.

Figure 16E:
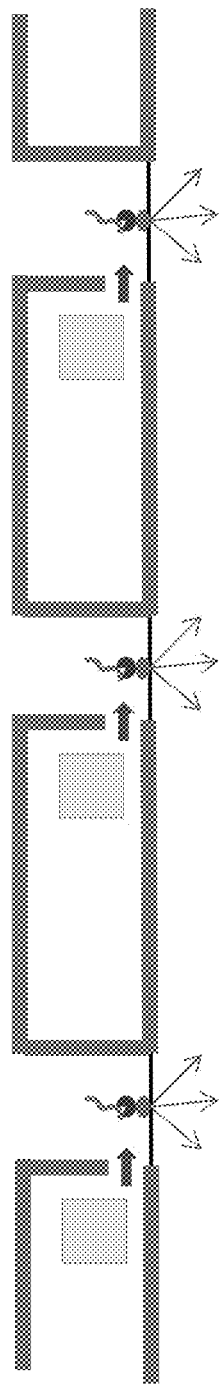

FIG. 16E represents an extension of the structure shown in FIG. 16A to illustrate how an array of nanowells could extend along one dimension, for example along the horizontal axis of the drawing. While not shown in the drawing it is understood that the arrays of nanowells can also extend in the direction extending into and out of the plane of the drawing, producing a two dimensional array of nanowells when viewed from above. For example, there can be rows of nanowells extending into and out of the plane of the drawing, each row adjacent to a waveguide, such that one waveguide illuminates all of the nanowells in a row. The drawing further illustrates that arrays of nanowells may be constructed using repetitive features, such as the opaque layers surrounding the illumination element. By repeating such structures along one dimension, it is possible to illuminate large number of nanowells in that dimension. In some embodiments, the repeating pattern would illuminate at least 100, at least 1000, at least 10,000, or even more nanowells. The repeating pattern could extend at least 10 μm, at least 100 μm, at least 1 mm, at least 10 mm, or even longer in that dimension.

When the nanowell is illuminated from the side, for example as shown in the nanowells exemplified in FIGS. 16A, 16B, 16E, 16F, and 16G, the opposite wall of the nanowell may be opaque, as shown, although under some circumstances it may be desirable for performance or processing reasons for the opposite side wall not to be coated, allowing for an excitation signal to pass through the opposite wall of the nanowell.

Figure 16G:
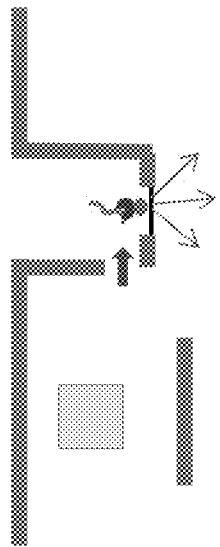
Figure 16F:
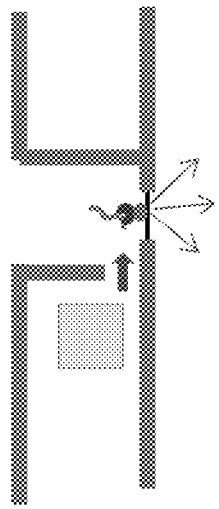

FIG. 16F illustrates another variation of the nanowell shown in FIG. 16A. In this nanowell, the opaque layer on the surface of the transparent substrate extends below the nanowell, resulting in an emission opening that is smaller than the cross-sectional dimensions of the nanowell itself. An exemplary device corresponding to the device of FIG. 16F is provided in Example 1. The emission opening with dimensions smaller than that of the nanowell can be used to limit the background signal from the nanowell. For example, when using this device for analysis such as single molecule sequencing, it is typically desired to observe fluorescent signal from species near the bottom of the nanowell (signal), but not to observe fluorescent signal from fluorescent species randomly diffusing through the nanowell (noise). Excitation light from the waveguide will extend into the nanowell and may interact with fluorophores diffusing through this volume. An emission opening that is smaller than the cross sectional dimensions of the nanowell allows for light emitted from fluorophores at the base of the well (e.g. labeled nucleotides in the active site of an immobilized polymerase) to pass into the layer below, but the emission opening will limit the amount of light emitted from diffusing fluorophores to pass into the layer below. This can result in an improved level of signal to noise (S/N) for the device. In some cases the emission opening has a cross sectional dimension of from about 40 nm to about 200 nm. In some cases, the emission opening has a cross sectional dimension from about 80 nm to about 150 nm. In some cases, the emissive opening is circular or substantially circular, but it can be elliptical, square, rectangular, or other shape. Where the emissive opening is circular, the cross sectional dimension is the diameter of the opening. The emission opening has a cross-sectional area that is smaller than the area of the base of the nanowell. The cross-sectional area of the nanowell can be from 10% to 80% of the area of the base of the nanowell, and is typically from 20% to 60% of the area of the base of the nanowell. Accordingly, in some embodiments of the device, the bottom surfaces of the plurality of nanowells of the device are at least partially opaque.

Accordingly, an exemplary analytical device that comprises structures of the type displayed in FIG. 16F comprises a cylindrical nanowell that is approximately 300 nm deep and 200 nm in diameter, and that has opaque walls that are approximately 20 nm thick and that extend 50% to 80% down the side wall of the nanowell. An opaque layer extends approximately 50 nm into the bottom of the nanowell and leaves an approximately 100 nm diameter emission opening to the transparent, e.g., silica, substrate. The illumination element consists of a waveguide comprising an aluminum nitride core and a silica cladding with cross-sectional dimensions of approximately 100 nm×200 nm. The waveguide is spaced approximately 100 nm from the opaque layer on the top, bottom, and side facing the nanowells. Each waveguide illuminates a row of from 100 to 10,000 nanowells, and this waveguide/nanowell pattern is repeated from 100 to 10,000 times orthogonally to the row of nanowells.

In some embodiments, for example as shown in FIG. 16G, it may advantageous for the position and size of the opaque layer below the waveguide to be adjusted so that the opaque layer blocks light from the waveguide that is directed toward the detector and that would therefore add to the background signal, while at the same time minimizing the amount of opaque layer used, and positioning the opaque layer as far away from the waveguide as possible, in order to limit propagation losses through the waveguide. In some situations, however, it may be beneficial for the portion of the opaque layer below the waveguide to be relatively close to the waveguide core. The size, composition, and position of the portion of the opaque layer below the waveguide core may be adjusted as desired in order to minimize the amount of background excitation signal reaching the detector and to maximize propagation of laser signal along the waveguide. Examples of alternative materials for use in the opaque layers, in particular opaque layers positioned between the waveguide core and the detectors, are provided below. It should also be noted that the materials used in the various regions of an opaque layer within a given analytical device may be the same or different, depending on the desired properties.

The opaque layers illustrated in FIGS. 16A-16G, 17A-17C, 18, 19, and 20 can be from about 5 nm to about 100 nm thick, are typically 5 nm to 30 nm thick but may, in some embodiments, be 5 nm to 20 nm thick. The distance between the illumination element and the nearest opaque layer is ideally at least 50 nm, although in some embodiments the distance may be at least 100 nm, at least 150 nm, or at least 300 nm. It should also be understood that different regions of the opaque layers illustrated in FIGS. 16A-16G, 17A-17C, 18, 19, and 20 may have different thicknesses or even been constructed of different materials, depending on the desired properties and behavior. Further examples of materials suitable for the construction of the opaque layers of the instant devices are provided below.

As noted above, an opaque layer may be a metallic layer, such as, for example, a layer of aluminum, but other suitable materials may also be utilized as an opaque layer within the scope of the invention. For example, an optical filter layer, such as, for example, a reflection interference filter layer or other suitable filter layer, may serve as an opaque layer, so long as the layer is chosen and configured appropriately according to wavelength of light being blocked.

An interference filter, as used herein, is typically a dichroic filter. The interference filter is an optical filter that reflects one or more spectral bands or lines and transmits others, while maintaining a low coefficient of absorption for wavelengths of interest. The interference filter may be high-pass, low-pass, bandpass, or band-rejection. The interference filter typically consists of multiple thin layers of dielectric material having different refractive indices. There also may be metallic layers within the interference filter.

Interference filters are wavelength-selective by virtue of the interference effects that take place between the incident and reflected waves at the thin-film boundaries. An interference filter used as the opaque layer, or as part of an opaque layer, in the instant invention is typically designed to block excitation light from a waveguide. In some cases, the interference filter has many layers, e.g. from 20 to 100 layers to block excitation light from the waveguide from reaching the detectors. In some cases, for example where an opaque layer is relatively close to the waveguide core, e.g. where the waveguide core is less than 500 nm, 300 nm, or 150 nm from the opaque layer, an interference filter with fewer layers, e.g. less than 10 layers or with 2, 3, 4, 5, 6, 7, 8, 9, or 10 layers may be used. In some cases, interference filters with 2, 4, or 6 layers is used. In some cases, an interference filter is used as an opaque layer instead of a metallic layer because the interference filter can block background laser light with lower propagation loss along the waveguide than with a metallic layer. In some cases, an optical layer is chosen as it can provide high levels of light blockage in a relatively thin layer.

Figure 17A:
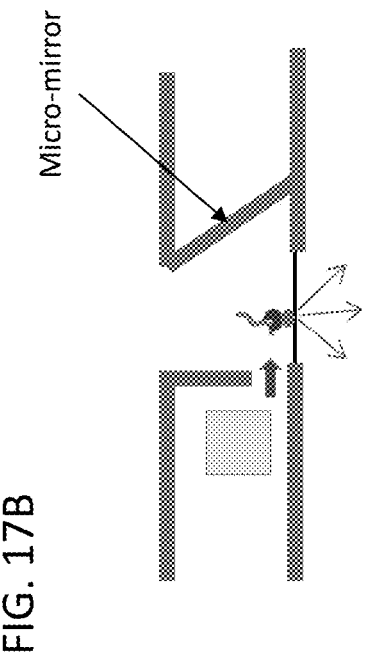
FIGS. 17A-17C illustrate variants of the devices of FIGS. 16A-16G with improved excitation coupling.
Figure 17B:
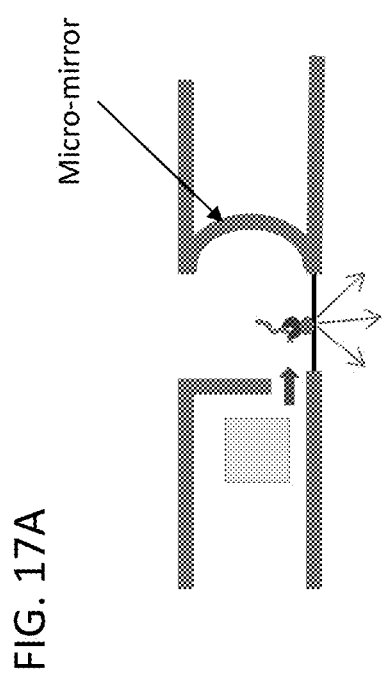
Figure 17C:
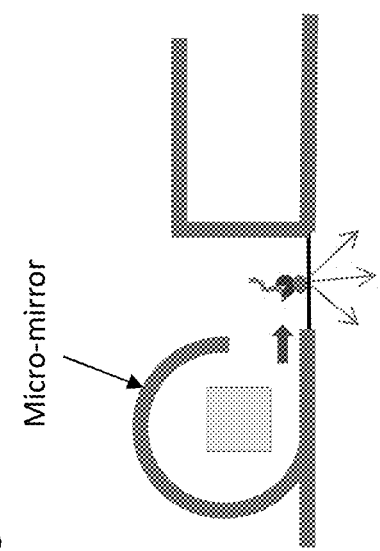

The devices containing an integrated illumination element may optionally include additional features, for example to improve the coupling of excitation energy to the sample. For example, as shown in FIGS. 17A and 17B, one or more walls of the nanowell may be coated with a reflective material and thus increase the efficiency of excitation of the sample by serving as a "micro-mirror" to reflect light back into the sample. Alternatively, or in addition, the surface of the opaque layer partly surrounding the integrated illumination element may itself be coated with a reflective material to form a "micro-mirror", as illustrated in FIG. 17C.

The efficiency of excitation coupling may optionally be further increased by altering the shapes of one or more side surfaces of the nanowell, for example by fabricating the side surface of the nanowell in a concave shape, as shown in FIG. 17A, or by angling the side surface of the nanowell toward the bottom surface of the nanowell, as shown in FIG. 17B. Alternatively, or in combination, the opaque layer partly surrounding the integrated illumination element may be cylindrical, as shown in FIG. 17C. Use of reflective materials on other surfaces of the nanowells and altering the shape of one or more side surfaces of the nanowells in other ways to improve coupling of excitation energy to the illumination volume are considered within the scope of the disclosure. Examples of the use of micromirrors to improve the coupling efficiency of emission energy from highly multiplexed samples to associated detectors are provided in U.S. Patent Application Publication No. 2010/0099100, which is incorporated by reference herein in its entirety for all purposes.

Figure 18:
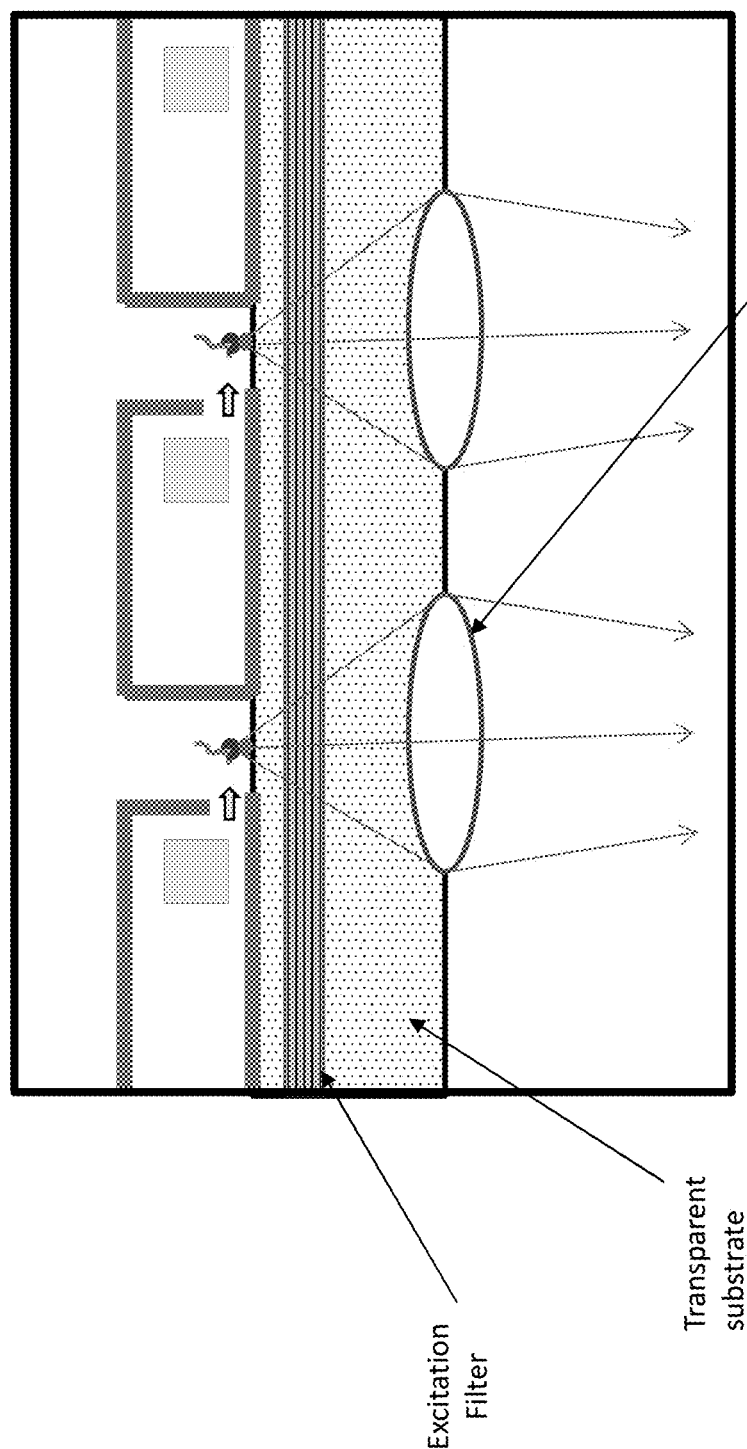
FIG. 18 illustrates a variant of the devices of FIGS. 16A-16G with improved detection.

The detection of emission signals from samples in the nanowells of any of the devices disclosed herein, including devices containing an integrated illumination element, may be further improved by the inclusion of additional optional components to improve collection of light by the detector elements. For example, as shown in FIG. 18, the provision of an excitation filter between the nanowells and the associated detector elements may improve the signal to noise ratio by blocking scattered excitation light from reaching the detectors. The design of the instant devices, wherein the excitation source is disposed on the surface of the substrate is already advantageous in this regard, because the emission signal does not need to pass through the excitation beam. In addition, the configuration of the opaque layer around the integrated illumination element advantageously minimizes the amount of stray excitation light able to reach the detectors and cause background signal.

FIG. 18 additionally illustrates the inclusion of a microlens optically coupled to each nanowell. Such microlenses focus light emitted from the nanowells and improve coupling of the emitted light to detachable detector elements. Alternatively, the microlenses may be substituted with integrated detector elements, such as, for example, charge coupled devices (CCDs), complementary metal oxide semiconductor (CMOSs), or the like, as would be understood by those of ordinary skill in the art.

Figure 19:
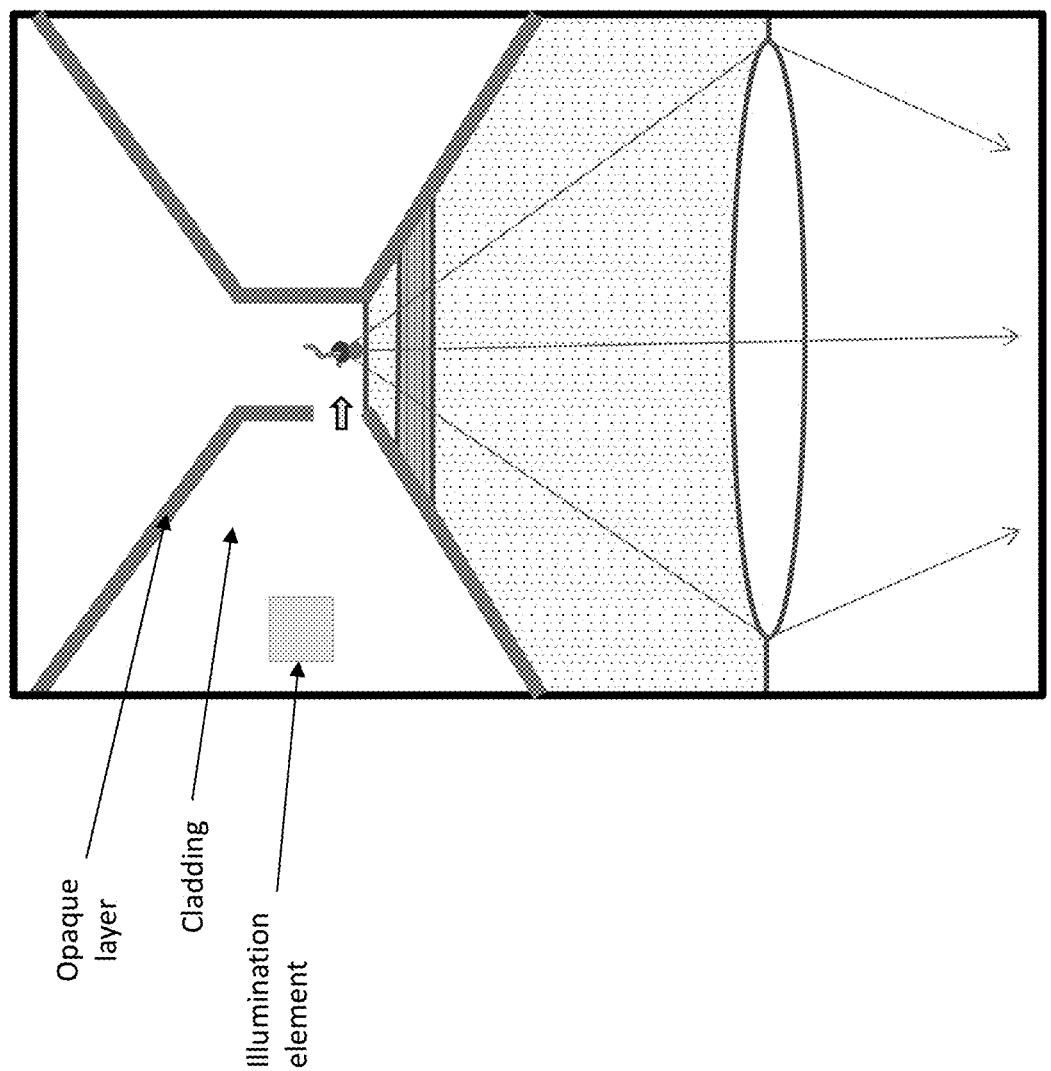
FIG. 19 illustrates a variant of the devices of FIGS. 16A-16G with additional spacing between the excitation source and the opaque layer.

The opaque layer of the devices illustrated in FIGS. 16A-16G, 17A-17C, 18, 19, and 20 may, in some embodiments, be a metallic layer. As described above, a metallic layer may cause propagation losses along a waveguide used to illuminate the samples, due to the proximity between the waveguide and the metallic layer, or may otherwise decrease the optical coupling from the waveguide to the sample. Accordingly, and as described above, it may be advantageous to increase the distance between a waveguide light source, such as may be employed in the integrated illumination element of these devices, and the opaque layer partly surrounding it. As shown in FIG. 19, this can be accomplished by increasing the thickness of the cladding surrounding the waveguide, in particular, by spreading the opaque layer above and below the waveguide, and, for example, by moving the waveguide away from the nanowell. As also described above, however, a metallic layer in the vicinity of the nanowell may serve as a local field enhancement element to improve the coupling of excitation light to the illuminated volume. The different effects should be considered and counterbalanced in the ultimate design of the integrated illumination element.

Figure 20:
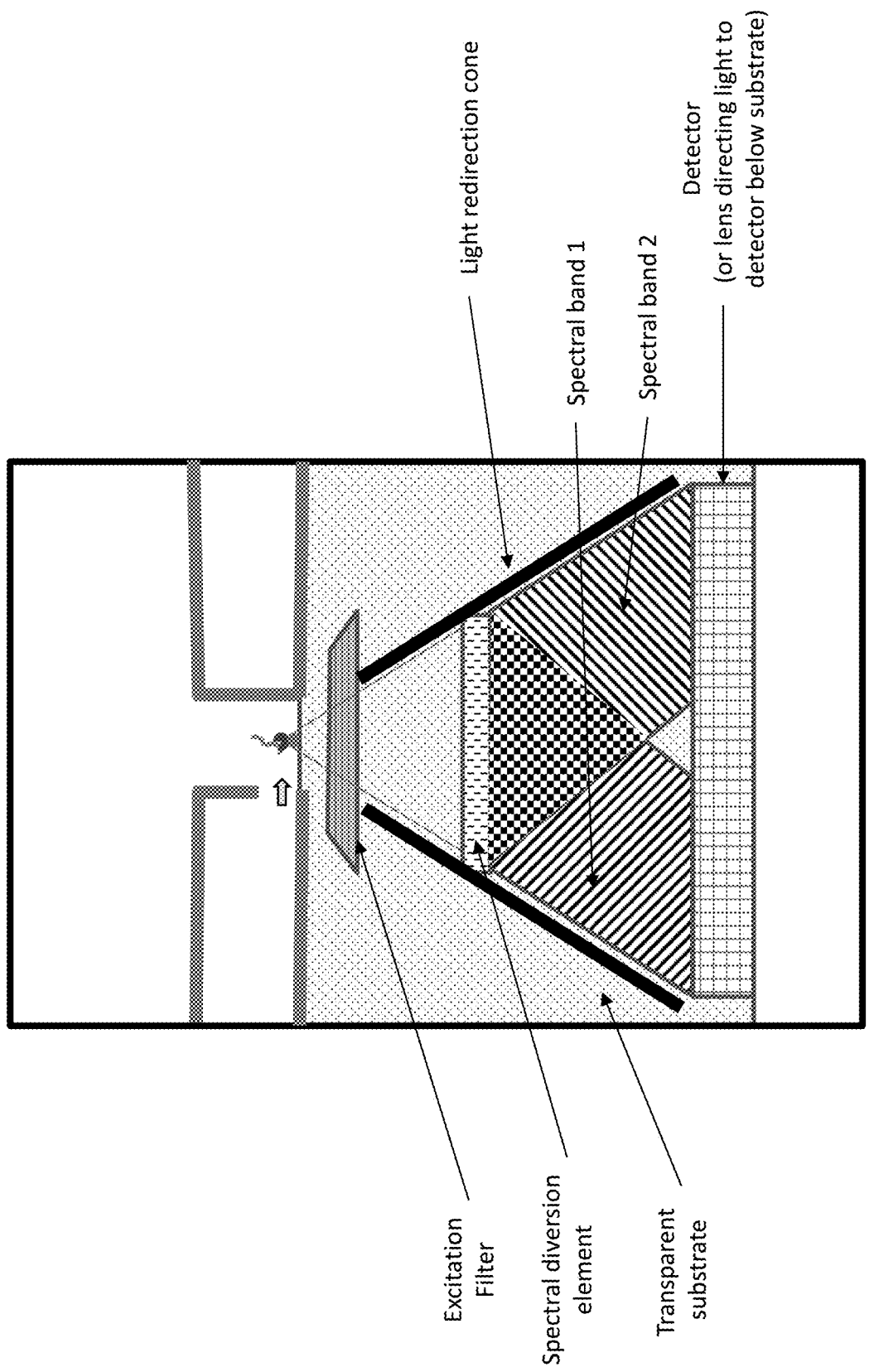
FIG. 20 illustrates a variant of the devices of FIGS. 16A-16G with additional detector features.

FIG. 20 illustrates two other optional components that may be incorporated into the transparent substrate of any of the instant devices. Specifically, this figure shows a spectral diversion element and a light redirection cone. The spectral diversion element according to this embodiment directs light emitted from each nanowell of the device to different locations according to wavelength. For example, light of spectral band 1 is directed to the left side of the device shown in FIG. 20, whereas light of spectral band 2 is directed to the right side of the device. As shown in the drawing, a detector, such as a CCD, a CMOS, or the like, positioned below the spectral diversion element can thus distinguish different wavelengths of emitted light according to position. Alternatively, a lens placed in this position can direct light to a detachable detector below the substrate. Intermediate cones or lenses to direct emitted light from the nanowells according to this embodiment may also facilitate further spectral separation.

The optional spectral diversion element of the instant devices, as illustrated graphically in FIG. 20, may be, for example, the spectral diversion element disclosed in U.S. Patent Application Publication No. 2012/0021525. Such an element serves to direct light emitted from the nanowell of the device to different spatial locations on a detector element, depending on the wavelength of the emitted light. In other words, the device creates a unique pattern on the detector that depends on wavelength. In some embodiments, the spectral diversion element may be a distinct layer within the emission zone, as illustrated in the embodiment shown in FIG. 20. In other embodiments, the spectral diversion element may be provided by a dispersive material that fills some or all of the space between the nanowell and the detector element. The spectral diversion element may in some embodiments be a prism, grating, or the like. It should be understood that spectral diversion elements capable of separating 2 colors, 3 colors, 4 colors, or even more colors are considered within the scope of the instant disclosure.

The optional light redirection cone of the instant devices, as illustrated graphically in FIG. 20, may include, or itself be a part of, additional optional features for improving the coupling of emitted light from the nanowell to the detector element. Such improved detection features are disclosed in detail, for example, in U.S. Patent Application Publication No. 2012/0021525. As described above, the use of micromirrors to improve the coupling efficiency of emission energy from highly multiplexed samples to associated detectors is disclosed in U.S. Patent Application Publication No. 2010/0099100.

It should be understood that the devices containing an integrated illumination element according to this aspect of the instant disclosure may additionally be combined with any of the local enhancement elements already described above.

The integrated illumination element of the devices illustrated in FIGS. 16A-16G, 17A-17C, 18, 19, and 20 may be any suitable light source. For example, the light source may be a waveguide configured so that it extends orthogonal to the plane of the drawings. The waveguide would therefore illuminate an entire row of nanowells along that dimension. In some embodiments, a single waveguide would illuminate at least 100, at least 1000, at least 10,000, or even more nanowells. The waveguide could extend at least 10 µm, at least 100 µm, at least 1 mm, at least 10 mm, or even longer. It should also be understood that the waveguide could be illuminated either by an external source, such as, for example, an external laser or other appropriate excitation device, or it could be illuminated by building laser elements, or other illumination elements, into the waveguide itself, as shown above and in FIGS. 15A-15G.

Alternatively, or in addition, to using a waveguide as the illumination element in the devices illustrated in FIGS. 16A-16G, 17A-17C, 18, 19, and 20, the light source may be a discrete light source, such as, for example, a semiconductor laser diode, a light-emitting diode, or a solid-state laser. Non-photonic sources of excitation energy, such as, for example, plasmonic excitation, may also be considered a discrete light source in these devices. The use of plasmonic excitation to illuminate samples in highly multiplexed analytical devices is described in U.S. Patent Application Publication No. 2012/0014837.

As just mentioned, among the discrete light sources usefully integrated into the instant analytical devices are semiconductor laser diodes. Semiconductor lasers are diodes that are typically electrically pumped. Most commonly, a semiconductor laser diode is formed from a p-n junction that is electrically pumped. The recombination of electrons and holes created by the applied current introduces optical gain. Reflection from the ends of the crystal results in an optical resonator. In some examples, the resonator may be external to the semiconductor.

Laser diodes are available with a wide variety of emission wavelengths, making them well suited to providing optical excitation in, for example, fluorescent DNA sequencing reactions. Laser diodes are likewise available having a wide variety of power outputs.

Vertical cavity surface-emitting lasers (VCSELs) are another type of semiconductor laser that may, in some embodiments, be integrated into the analytical devices of the instant disclosure as a discrete light source. In a VCSEL, the emission direction is perpendicular to the surface of the wafer. VCSEL devices typically have a more circular output beam than conventional laser diodes, and may, in some cases, be cheaper to manufacture.

Alternatively, instead of a diode material with a bandgap, a nonlinear optical material such as a second harmonic generation material could be used, so that when light of an appropriate angle shines on the medium, second harmonic generation creates light at a wavelength of half the illuminating wavelength. As described above, the use of a frequency conversion system, whether in a waveguide or as part of an integrated illumination system, has the advantage of being as monochromatic as the pump light and thus relatively easy to block from generating background signal in the detection zone.

As described above, a discrete light source, such as, for example, a light emitting diode (LED), a laser diode, a nonlinear optical element, or the like, may be added to each optical confinement independently to provide excitation light. Integration of the illumination device with each illuminated volume on a sample chip would simplify the system in several ways, for example with respect to energy input, since it would only be necessary to apply a DC voltage to the illumination element, and with respect to optical output, since no data collection electronics, high speed circuitry, filters, or complex CMOS pixel structures with multiple transistors would necessarily be needed. The following description relates to a 1-color illumination device, but the same principles apply equally to 1, 2, 3, 4, or more color illumination devices. The provision of additional colors would just entail duplicating the diodes. For example, a 4-color LED would be fabricated by integrating 4 different diodes together.

Figure 21:
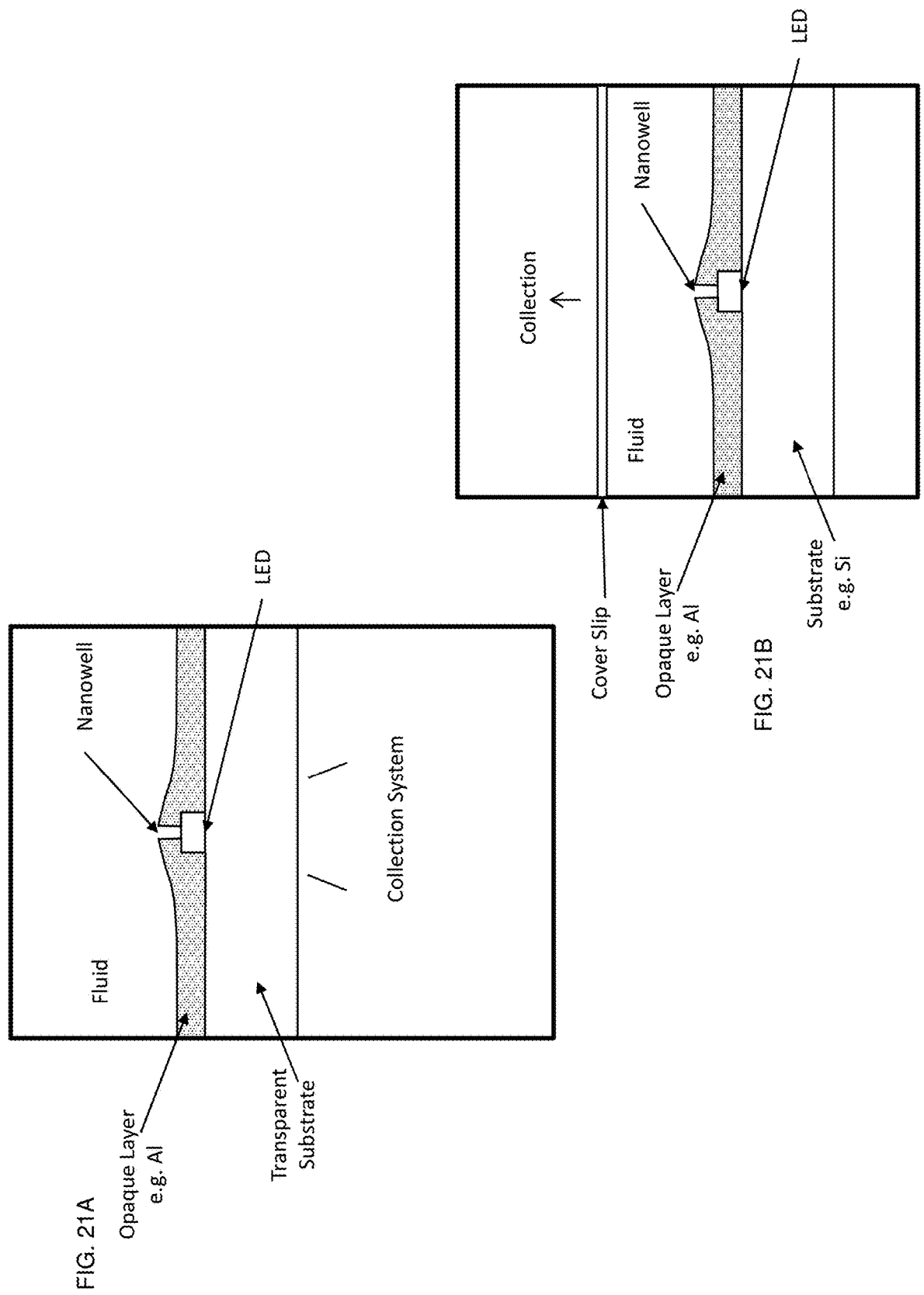
FIGS. 21A-21B show exemplary analytical devices with integrated LED elements, where detection is either below the device, through a transparent substrate (FIG. 21A), or above the device, where the substrate is opaque (FIG. 21B).

Turning to FIGS. 21A-21B, 22, 23A-23B, 24, 25, 26, 27, 28, and 29, various additional alternative approaches to integrating a discrete light source into an analytical device are provided. In FIGS. 21A-21B, for example, an LED, or other such light source, is placed on the surface of a substrate, directly below a nanowell, for example within an opaque, metallic layer. Where the LED and substrate are transparent to emitted light, the collection system, including a camera or integrated detector, may be placed below the light source, as shown in FIG. 21A. Alternatively, for example if the substrate and LED are not transparent, the collection system may be configured to collect emission light through the fluid above the chip, for example through a cover slip as shown in FIG. 21B. The latter configuration would allow for the use of silicon-based substrates, and may therefore offer more fabrication pathways and lower cost.

There are also at least two broad categories of LED structures that could be used as discrete light sources in such systems: opaque and transparent. Opaque LED structures, just as with opaque substrate structures, allow the full range of device structures and fabrication techniques, but when used with a transparent substrate, they are preferably arranged so as not to interfere with the collection, as illustrated schematically in FIG. 22. Transparent LED structures may be arranged "in series" with the collection path, as illustrated schematically in FIGS. 23A-23B, and collection can accordingly be performed either above or below the chip, as desired. Such configurations may potentially be more efficient in terms of getting the generated light to the illumination volume, but the choice of materials, device structures, and processes may be somewhat more limited.

It should also be understood that the emission of light from an LED may be highly directional. Specifically, light is typically emitted nearly perpendicularly from the surface of the p-type layer of an LED, in a cone shape. Fabrication of LEDs within the devices of the instant disclosure should therefore take this directionality into account, such that the light from the LED is appropriately targeted to the illumination volume, as desired. For example, the device shown in FIG. 22 would be fabricated such that light is emitted from the interior sidewall of the illustrated LED cylinder. Other similar device embodiments utilizing one or more LEDs to illuminate a non-cylindrical nanowell from the side could be readily envisioned by one of ordinary skill in the art. For example, a multi-sided nanowell could be illuminated by one or more LEDs built into one or more sidewalls of the nanowell.

There are several general approaches for patterning LEDs, as would be understood in the art, thus providing a great deal of flexibility in design. For example, a simple pillbox shape could be used to illuminate each nanowell, or simpler strip structures could be used to light up rows of nanowells. The latter could be easier to fabricate but may be less efficient in terms of electrical power required, thermal dissipation, and susceptibility to failure (e.g., a single failure could wipe out a larger number of nanowells).

Figure 22:
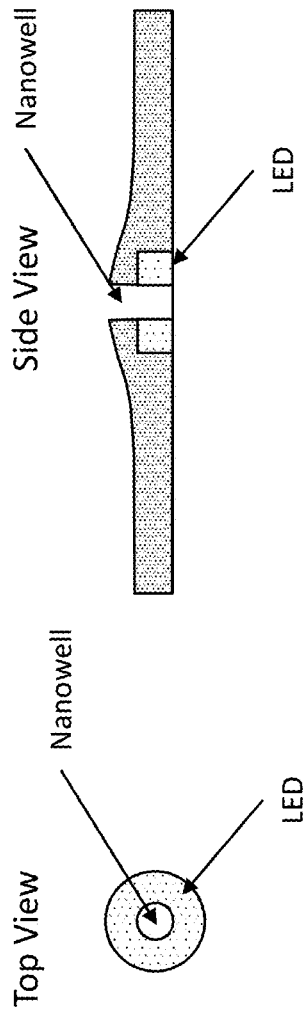
FIG. 22 shows an exemplary analytical device with an integrated LED element, where excitation is from the side of a nanowell and detection is above or below the nanowell.
Figure 23B:
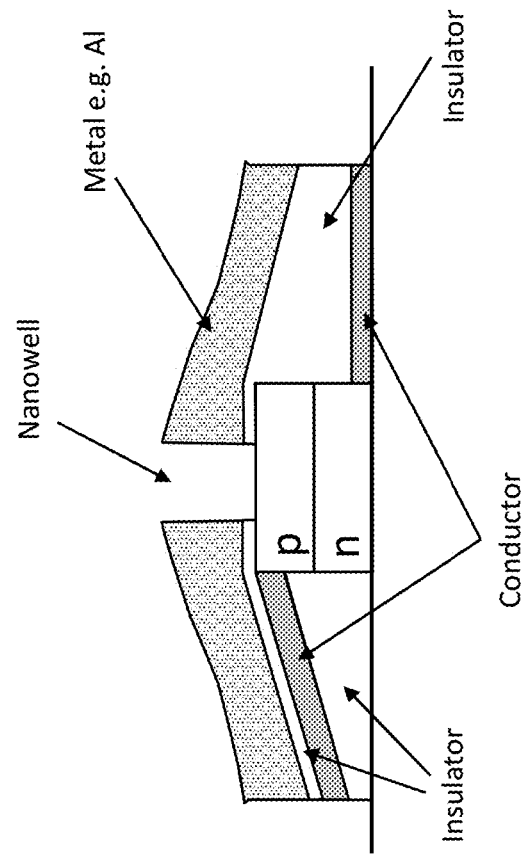
FIG. 23B shows in more detail the conductors connected to the LED and their insulation.
Figure 23A:
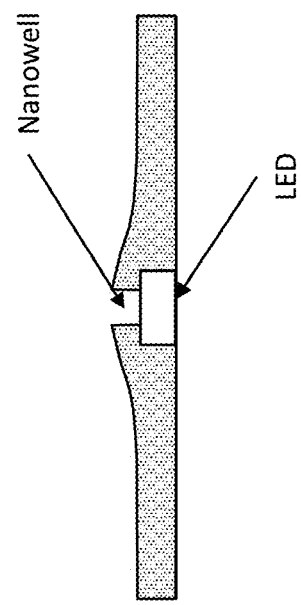
FIG. 23A shows an exemplary analytical device with an integrated, transparent LED element, where excitation is from below the nanowell and detection is above or below the nanowell.
Figure 24:
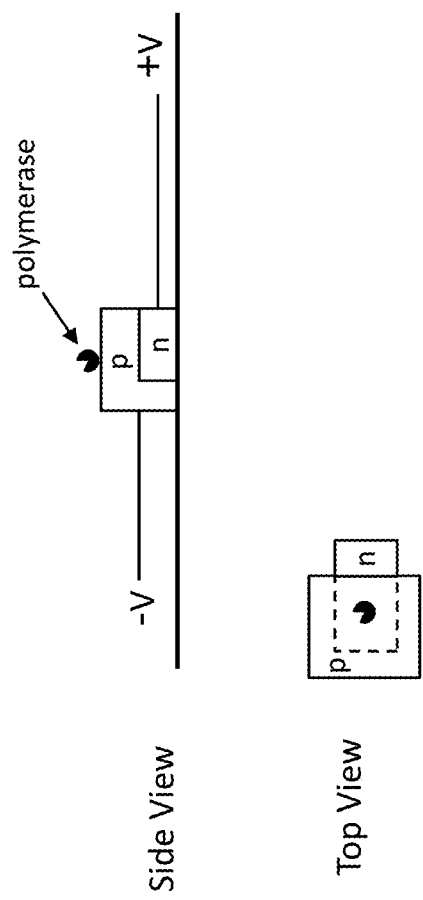
FIG. 24 illustrates an exemplary analytical device having an integrated LED element but no metallic layer or nanowell.
Figure 25:
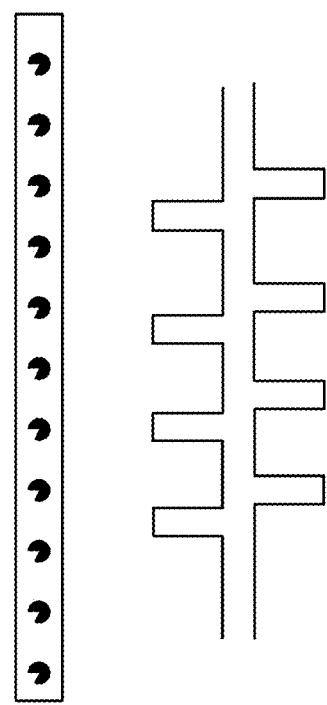
FIG. 25 illustrates various patterns of LEDs or other discrete light sources.

When a discrete light source is used to illuminate a nanowell, the depth of the nanowell, i.e., the vertical dimension of FIGS. 21A-21B and 23A-23B, and of the side view in FIG. 22, is ideally from 50 nm to 1000 nm, and the cross-sectional shape of the nanowell can be cylindrical, elliptical, square, rectangular, or any other suitable shape. The cross-sectional dimension of the nanowell in these embodiments is typically from 50 nm to 1000 nm, but may more specifically be from 100 nm to 400 nm.

Figure 26:
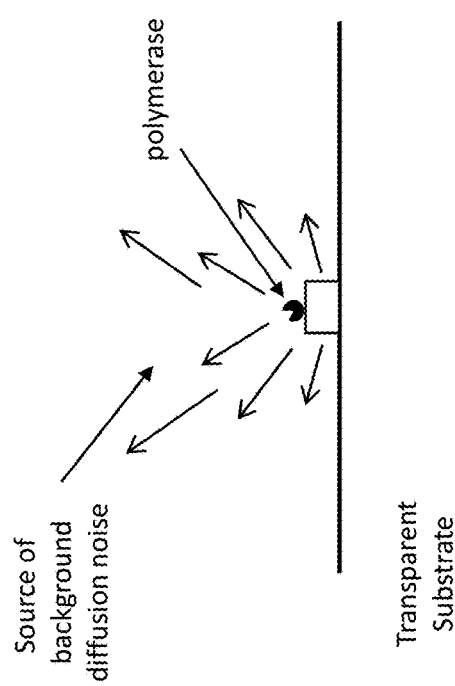
FIG. 26 shows the source of background diffusion noise in a device that lacks a nanowell for sample containment.
Figure 27:
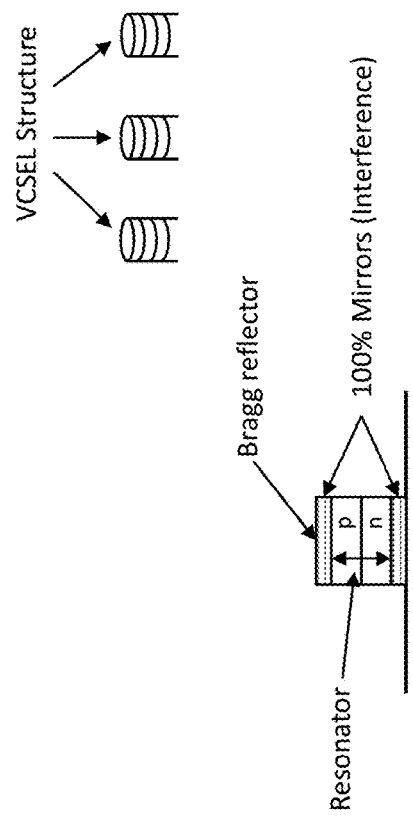
FIG. 27 shows the structure of an exemplary cavity resonator device with high reflector mirrors to minimize light emission.
Figure 28:
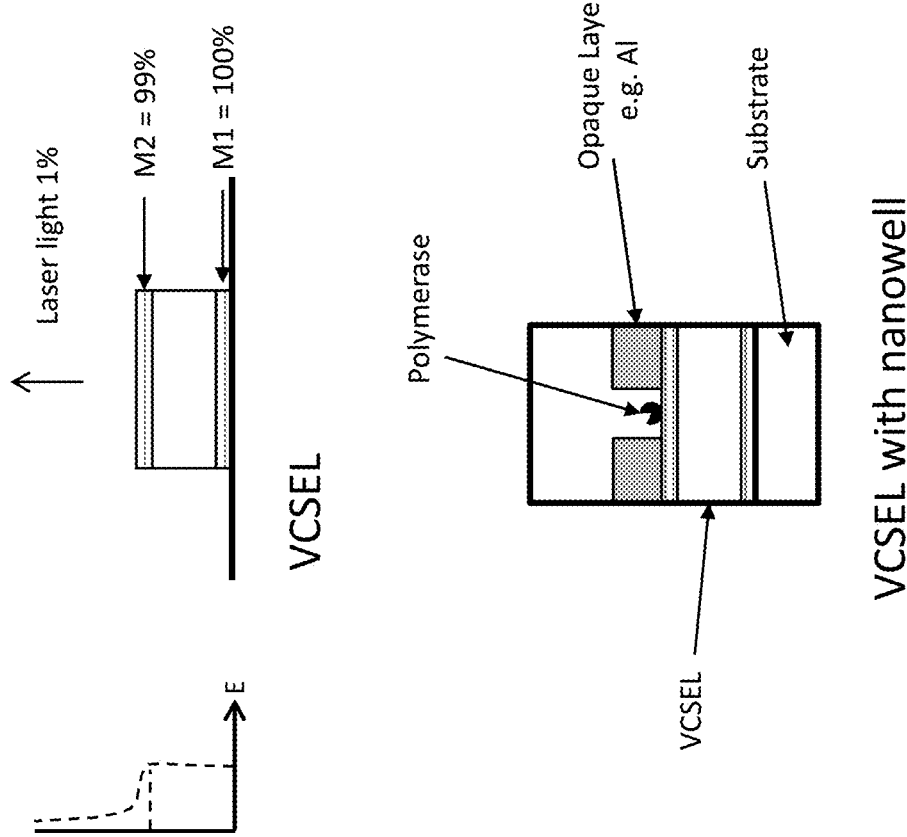
FIG. 28 illustrates the structure of a VCSEL (top) for use in an analytical device containing an opaque, metallic layer and a nanowell (bottom). The top mirror of the VCSEL is a partial reflector to allow for some light transmission.
Figure 29:
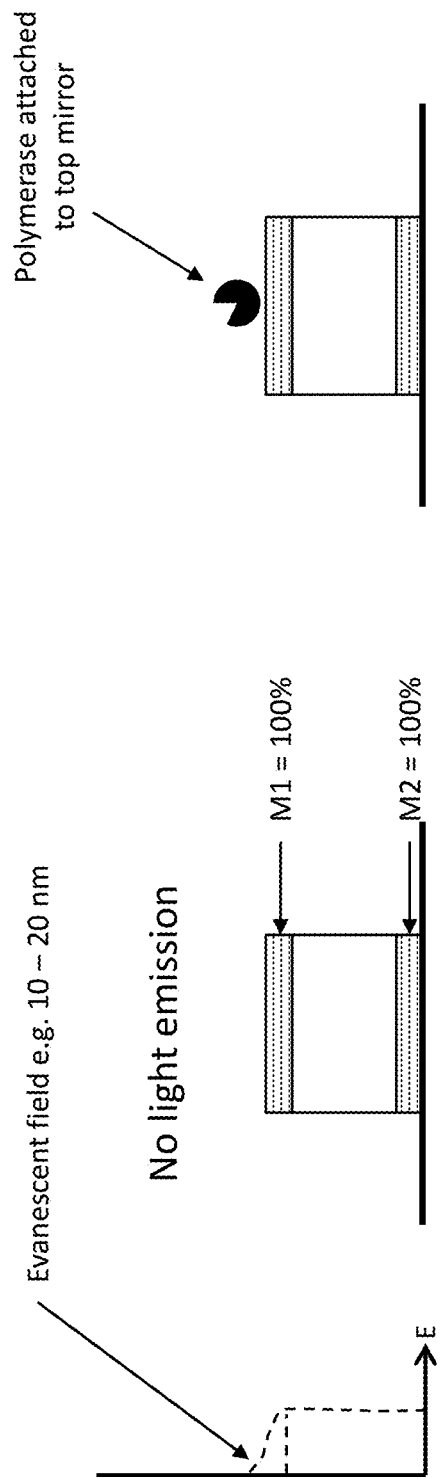
FIG. 29 illustrates another embodiment of a cavity resonator device (left) for use in an analytical device that may optionally include no nanowell (right). The device is tuned to minimize light emission. The graph on the left of the drawing illustrates an evanescent field emanating from the surface of the device. Excitation coupling of the sample results from the evanescent field.

In some embodiments of devices comprising a discrete light source, it may be possible to eliminate the need for nanowells on the surface of the device altogether. Although the devices illustrated in FIGS. 21A-21B, 22, and 23A-23B include a nanowell for sample containment, this function may not be necessary in devices incorporating LEDs or other integrated illumination. The devices could therefore potentially be fabricated without the metallic layer or the nanowells disposed in this layer. Specifically, the small size of the LED structure itself, and the high directionality of the emitted light, may provide lateral confinement in the sample plane, and such structures could be fabricated much smaller than the optical resolution limit. For example, circular emitting regions, such as the one illustrated schematically in FIG. 24, or strips or other complicated shapes, such as those illustrated schematically in FIG. 25, could be utilized in the design of an integrated illumination element. Of importance in designing these structures is to provide a small enough space for the lateral light confinement and then to balance the vertical confinement against the background noise introduced by excitation light that may be emitted up into the solution, for example, in the case of traditional DNA sequencing reactions, beyond the immobilized polymerase enzyme, for example, as shown in FIG. 26. With the integrated illumination schemes, autofluorescence accumulation does not contribute to the background signal, but noise from background diffusion should be minimized through design and layout as the devices are scaled up and multiplexed. Furthermore, where the device is used in the monitoring of an enzyme-catalyzed reaction, such as in DNA sequencing reactions, the surface of the LED is preferably fabricated to facilitate the anchoring of an enzyme, e.g., DNA polymerase, either directly to the LED emitting surface or to an additional layer designed into the structure.

For analytical devices using integrated LEDs, the flexibility in design of LED structure allows for a large variety of different approaches. For example, an LED in pillbox shape may be simple and straightforward, particularly where the devices lack nanowells for sample containment, although, as described above, background diffusion noise may be problematic in such devices. For devices that lack nanowells, the discrete light source may be designed with this in mind to minimize signal from background diffusion. For example, a discrete light source, such as a vertical cavity surface emitting laser (VCSEL), may be usefully employed to minimize the background signal. As illustrated schematically in FIG. 27, the laser resonator in a VCSEL device is a type of laser diode consisting of two distributed Bragg reflector mirrors parallel to the surface of the substrate. As shown in this figure, the upper region contains a p-type material, and the lower region contains an n-type material, together forming a diode junction. Such a structure generates laser beam emission from the top surface. As illustrated schematically in FIG. 28, the laser emission from a VCSEL device extends significantly away from the surface of the device (top panel), and it is therefore useful to fabricate nanowells on the surface of the VCSEL device by adding a metallic layer over the integrated device and patterning the nanowells, where, for example, a DNA polymerase molecule may be immobilized (bottom panel). The inclusion of the nanowell structure helps to minimize background diffusion noise. VCSELs are also ideally suited to highly multiplexed analytical devices, such as the devices of the instant disclosure, due to the orientation of their light emission and the ability to fabricate them in two-dimensional arrays.

In some embodiments, where the analytical devices display simplified structures lacking a metallic layer or nanowells, it may be advantageous to fabricate a modified structure that does not emit light at all. For example, if the mirror and cavity are re-tuned to the structure shown in the top panel of FIG. 29, for example, where the, e.g., 99% laser reflector is replaced by a 100% laser reflector, and the laser resonator becomes a cavity resonator (i.e., a vertical cavity resonator (VCR)), there is no laser light emission from the surface and thus no background diffusion noise. In such a device, the vertical light confinement function of the nanowell/ZMW is replaced by the evanescent field at the top surface of the resonator, which extends from the surface only 10-20 nm, and the lateral confinement function of the nanowell/ZMW is replaced by the small VCSEL geometry. In all cases, the geometries are balanced against the fluorophore concentration for the ultimate necessary signal to noise ratio. Depending on the substrate, collection of emission signal may be either below the device (for a transparent substrate) or above the device through the fluid sample (for an opaque substrate).

As described above, whether using an extended illumination element, such as a laser or waveguide illumination element, or using a discrete light source, such as an LED or other similarly configured light source, it is envisioned that the arrays of the instant analytical devices can extend in each direction by at least 100, at least 1000, at least 10,000, or even more nanowells. Depending on the exact layout of the devices, specifically on whether the nanowells are organized in regular rows or in some other pattern on the device, and whether the devices are shaped as squares, rectangles, or some other geometric shape, the devices are expected to comprise at least 1,000, at least 10,000, at least 100,000, at least 1,000,000, or even at least 10,000,000 illumination volumes within those nanowells.

In yet another aspect, the disclosure provides analytical devices of the following numbered paragraphs.

1. An analytical device comprising:
   an optical waveguide comprising an optical core and a cladding;
   a metallic layer disposed on a surface of the cladding;
   a plurality of nanometer-scale apertures disposed in the metallic layer in sufficient proximity to the optical waveguide to be illuminated by an evanescent field emanating from the waveguide when optical energy is passed through the optical core; and
   a plurality of local field enhancement elements associated with the plurality of apertures.

2. The analytical device of paragraph 1, wherein the local field enhancement elements comprise a high dielectric material or metal in the vicinity of the apertures.

3. The analytical device of paragraph 2, wherein the high dielectric material or metal is arranged in a geometric pattern around the apertures.

4. The analytical device of paragraph 3, wherein the geometric pattern is selected from the group consisting of a circle, a series of concentric circles, a C aperture, a triangle pair, and a diamond.

5. The analytical device of paragraph 2, wherein the high dielectric material or metal is $Al_2O_3$, copper, silver, gold, or aluminum.

6. The analytical device of paragraph 5, wherein the high dielectric material or metal is $Al_2O_3$.

7. The analytical device of paragraph 5, wherein the high dielectric material or metal is copper.

8. The analytical device of paragraph 1, wherein the apertures are recessed into the cladding.

9. The analytical device of paragraph 1, wherein the thickness of the cladding between the optical core and the metallic layer decreases in the vicinity of the apertures.

10. The analytical device of paragraph 9, wherein the thickness of the cladding is from 150 to 300 nm.

11. The analytical device of paragraph 10, wherein the thickness of the cladding is about 200 nm.

12. The analytical device of paragraph 1, wherein the local field enhancement elements comprise the shape of the nanometer-scale apertures.

13. The analytical device of paragraph 12, wherein the shape of the nanometer-scale apertures is selected from the group consisting of a C aperture, a triangle pair, and a diamond.

14. An analytical device comprising:
   an optical waveguide comprising an optical core and a cladding;
   a metallic layer disposed on the surface of the cladding; and
   a plurality of nanometer-scale apertures disposed in the metallic layer in sufficient proximity to the optical waveguide to be illuminated by an evanescent field emanating from the waveguide when optical energy is passed through the optical core;
   wherein the optical core has a thickness, a width, and a cross-sectional area, and wherein the cross-sectional area is decreased at locations where the evanescent field illuminates the apertures.

15. The analytical device of paragraph 14, wherein the cross-sectional area is decreased by adiabatic tapers.

16. The analytical device of paragraph 14, wherein the thickness of the optical core is maintained, and the cross-sectional area is decreased by decreasing the width of the optical core.

17. The analytical device of paragraph 16, wherein the optical energy is transverse electric polarized light.

18. The analytical device of paragraph 14, wherein the width of the optical core is maintained, and the cross-sectional area is decreased by decreasing the thickness of the optical core.

19. The analytical device of paragraph 18, wherein the optical energy is transverse magnetic polarized light.

20. The analytical device of paragraph 14, further comprising a plurality of local field enhancement elements associated with the plurality of apertures.

21. The analytical device of paragraph 20, wherein the local field enhancement elements comprise a high dielectric material or metal in the vicinity of the apertures.

22. The analytical device of paragraph 21, wherein the high dielectric material or metal is arranged in a geometric pattern around the aperture.

23. The analytical device of paragraph 22, wherein the geometric pattern is selected from the group consisting of a circle, a series of concentric circles, a C aperture, a triangle pair, and a diamond.

24. The analytical device of paragraph 21, wherein the high dielectric material or metal is $Al_2O_3$, copper, silver, gold, or aluminum.

25. The analytical device of paragraph 24, wherein the high dielectric material or metal is $Al_2O_3$.

26. The analytical device of paragraph 24, wherein the high dielectric material or metal is copper.

27. The analytical device of paragraph 20, wherein the apertures are recessed into the cladding.

28. The analytical device of paragraph 20, wherein the thickness of the cladding between the optical core and the metallic layer decreases in the vicinity of the apertures.

29. The analytical device of paragraph 28, wherein the thickness of the cladding is from 150 to 300 nm.

30. The analytical device of paragraph 29, wherein the thickness of the cladding is about 200 nm.

31. The analytical device of paragraph 20, wherein the local field enhancement elements comprise the shape of the nanometer-scale apertures.

32. The analytical device of paragraph 31, wherein the shape of the nanometer-scale apertures is selected from the group consisting of a C aperture, a triangle pair, and a diamond.

33. An analytical device comprising:
an optical waveguide comprising a plurality of optical cores and a cladding;
a plurality of nanometer-scale apertures disposed on a surface of the device in sufficient proximity to the optical waveguide to be illuminated by an evanescent field emanating from the waveguide when optical energy is passed through the plurality of optical cores; and
a plurality of detectors optically coupled to the plurality of nanometer-scale apertures;
wherein the optical cores are not in direct alignment between the nanometer-scale apertures and their optically coupled detectors.

34. The analytical device of paragraph 33, wherein the plurality of nanometer-scale apertures are illuminated by an evanescent field emanating from at least two optical cores.

35. The analytical device of paragraph 33, further comprising an opaque layer disposed between the optical waveguide and the plurality of optical detectors, wherein the opaque layer comprises a plurality of openings in direct alignment with the nanometer-scale apertures and their optically coupled detectors.

36. The analytical device of paragraph 33, wherein the device further comprises a plurality of local field enhancement elements associated with the plurality of apertures.

37. The analytical device of paragraph 36, wherein the local field enhancement element comprises a high dielectric material or metal in the vicinity of the aperture.

38. The analytical device element of paragraph 37, wherein the high dielectric material or metal is arranged in a geometric pattern around the aperture.

39. The analytical device element of paragraph 38, wherein the geometric pattern is selected from the group consisting of a circle, a series of concentric circles, a C aperture, a triangle pair, and a diamond.

40. The analytical device element of paragraph 37, wherein the high dielectric material or metal is $Al_2O_3$, copper, silver, gold, or aluminum.

41. The analytical device element of paragraph 40, wherein the high dielectric material or metal is $Al_2O_3$.

42. The analytical device element of paragraph 40, wherein the high dielectric material or metal is copper.

43. The analytical device element of paragraph 33, wherein the apertures are recessed into the cladding.

44. The analytical device of paragraph 33, wherein the thickness of the cladding decreases in the vicinity of the apertures.

45. The analytical device of paragraph 44, wherein the thickness of the cladding thickness is from 150 to 300 nm.

46. The analytical device of paragraph 45, wherein the thickness of the cladding is about 200 nm.

47. An analytical device comprising:
an optical waveguide comprising an optical core and a cladding; and
a plurality of nanometer-scale apertures disposed on a surface of the device in sufficient proximity to the optical waveguide to be illuminated by an evanescent field emanating from the waveguide when optical energy of a defined wavelength is passed through the optical core;
wherein the wavelength of the optical energy is modulated as it passes through the optical core.

48. The analytical device of paragraph 47, wherein the optical waveguide comprises a non-linear optical material.

49. The analytical device of paragraph 48, wherein the non-linear optical material is placed periodically within the optical core.

50. The analytical device of paragraph 48, wherein the non-linear optical material is placed within the cladding.

51. The analytical device of paragraph 47, wherein the wavelength conversion is effected through phase matching.

52. The analytical device of paragraph 47, wherein the wavelength conversion is effected through electro-optical effects.

53. The analytical device of paragraph 47, wherein the optical energy is modulated by second harmonic generation.

54. The analytical device of paragraph 47, wherein the optical energy is modulated by third harmonic generation.

55. The analytical device of paragraph 47, wherein the optical energy is modulated by optical parametric amplification.

56. The analytical device of paragraph 47, further comprising a plurality of local field enhancement elements associated with the plurality of apertures.

57. The analytical device of paragraph 56, wherein the local field enhancement elements comprise a high dielectric material or metal in the vicinity of the aperture.

58. The analytical device of paragraph 57, wherein the high dielectric material or metal is arranged in a geometric pattern around the aperture.

59. The analytical device of paragraph 58, wherein the geometric pattern is selected from the group consisting of a circle, a series of concentric circles, a C aperture, a triangle pair, and a diamond.

60. The analytical device of paragraph 57, wherein the high dielectric material or metal is $Al_2O_3$, copper, silver, gold, or aluminum.

61. The analytical device of paragraph 60, wherein the high dielectric material or metal is $Al_2O_3$.

62. The analytical device of paragraph 60, wherein the high dielectric material or metal is copper.

63. The analytical device of paragraph 56, wherein the apertures are recessed into the cladding.

64. The analytical device of paragraph 56, wherein the thickness of the cladding decreases in the vicinity of the apertures.

65. The analytical device of paragraph 64, wherein the thickness of the cladding is from 150 to 300 nm.

66. The analytical device of paragraph 65, wherein the thickness of the cladding is about 200 nm.

67. The analytical device of paragraph 56, wherein the local field enhancement elements comprise the shape of the nanometer-scale apertures.

68. The analytical device of paragraph 67, wherein the shape of the nanometer-scale apertures is selected from the group consisting of a C aperture, a triangle pair, and a diamond.

69. The analytical device of any one of paragraphs 1-68, wherein the analytical device further comprises a plurality of analytes disposed in analyte regions within the plurality of nanometer-scale apertures.

70. The analytical device of paragraph 69, wherein the plurality of analytes comprise a plurality of biological samples.

71. The analytical device of paragraph 70, wherein the plurality of biological samples comprise a plurality of nucleic acids.

72. The analytical device of any one of paragraphs 1-68, wherein the analytical device comprises at least 1,000, at least 10,000, at least 100,000, at least 1,000,000, or at least 10,000,000 nanometer-scale apertures.

It will be readily apparent to one of ordinary skill in the relevant arts that other suitable modifications and adaptations to the analytical devices described herein may be made without departing from the scope of the invention or any embodiment thereof. Having now described the present invention in detail, the same will be more clearly understood by reference to the following Example, which is included herewith for purposes of illustration only and is not intended to be limiting of the invention.

EXAMPLE

Example 1: Analytical Device with Side Waveguide Illumination of Nanoscale Apertures FIG. 30 shows a cross-sectional view of a portion of an analytical device of the invention for side waveguide illumination of nanoscale apertures/nanowells. The cross-section shows a nanowell 3066 illuminated by waveguide core 3065. The analytical device has one million nanowells in an array of 1000 by 1000. The waveguide core 3065 extends into and out of the plane of the drawing, illuminating 1000 nanowells. There are 1000 waveguides, aligned parallel to one another, each illuminating a row of 1000 nanowells.

The device is produced using semiconductor processing technology on a CMOS wafer 3010. The CMOS wafer in this example is a detector having two million pixels. In FIG. 30, two pixels are represented in cross-section as 3012 and 3014. Each nanowell within this exemplary device is optically associated with two pixels.

A filter layer 3020 is positioned on top of the CMOS wafer. The filter layer is produced such that a specific filter is associated with the pixel directly below it. For each set of two pixels associated with a particular nanowell, there are two different filters, e.g. 3022 and 3024, each allowing a different set of wavelengths of light to pass to the pixel below. The filter layer is approximately 1 micron thick.

A lens layer 3030 is positioned on top of the filter layer. In the device of FIG. 30, this lens layer is a Fresnel lens layer comprising a bottom oxide layer 3032 and a top layer 3034 comprising, for example, alpha-silicon. The lens layer directs light emitted from the nanowell 3066 through the filter layer and onto the pixels 3012 and 3014. The thickness of the lens layer is approximately 5 microns. The thickness of the bottom oxide layer is selected to allow for the light redirected by the lens elements to be effectively separated and directed to the appropriate pixel.

A laser interference rejection filter 3040 is positioned on top of the lens layer. This laser rejection filter specifically reflects laser light from the waveguide while allowing signal light of longer wavelength emitted from the nanowell to pass. In the exemplary device, an antireflective coating 3042, about 80 nm thick, is positioned on the top surface of the laser interference rejection filter. The antireflective coating is designed to transmit the wavelengths of signal light. The exemplary device additionally includes an optional light transmission layer 3050 comprising silicon dioxide on the top surface of the laser interference rejection filter. This transparent layer acts as a spacer for controlling the manner in which light emitted from the nanowell enters the layers below. The transparent layer is about 2 microns thick.

A waveguide/nanowell layer, or illumination element layer, 3060 is positioned on the top surface of the transparent layer. The waveguide/nanowell layer includes a waveguide core 3065 which is disposed to the side of nanowell 3066. The waveguide is composed of a relatively high refractive index material such as silicon nitride. The waveguide is approximately 150 nm thick and 400 nm wide. The edge of the waveguide core 3065 is approximately 500 nm from the nanowell 3066. In the exemplary device, the waveguide is surrounded by silicon dioxide having a thickness of approximately 300 nm. The lower part of the waveguide/nanowell layer includes an opaque layer 3062 composed of aluminum that is 10 nm to 20 nm thick. In the device of FIG. 30, the opaque layer 3062 is a continuous layer except for an emission opening 3067, which is positioned under the nanowell 3066. The emission opening is round with a diameter of about 100 nm. The nanowell itself is cylindrical with a diameter of about 300 nm. An opaque aluminum layer 3064 is positioned on the top surface of the waveguide/nanowell layer. The opaque aluminum layer is approximately 20 nm to 30 nm thick. This layer typically covers the entire top surface of the device, except for the nanowell. It protects the solution above the device from exposure to excitation light from the waveguide.

In the exemplary device, the overall thickness of the portion of the device above CMOS layer 3010 is approximately 9 microns.

For performing single-molecule sequencing using the exemplary analytical device, a single polymerase-template complex is immobilized within the emission opening 3067 at the bottom of nanowell 3066. The top of the device is exposed to the reagents required for carrying out nucleic acid synthesis including phospho-labeled nucleic acids. Laser excitation light is passed through waveguide 3065 as the polymerase-dependent nucleic acid synthesis occurs at the polymerase-template complex. Excitation light from the evanescent field emanating from the waveguide is coupled into the nanowell 3066, exciting fluorophores within the nanowell. Nucleotides which are incorporated can be distinguished from freely diffusing nucleotides, as incorporated nucleotides have a longer residence time. In addition, the emission opening 3067 preferentially allows the passage of light from species near the bottom and center of the nanowell, such as those associated with the polymerase enzyme.

Emitted light from the labels is directed to the filters by the lens layer toward the two pixels below the nanowell. The four nucleotides are differently labeled, for example with two different colors, each at two different amplitudes. Thus, one pixel, e.g. 3012 will detect the events corresponding to two of the nucleotides, and the identity of each can be distinguished by differences in amplitude. The other pixel will detect events corresponding to the other two nucleotides. By monitoring the incorporation events for the four nucleotides over time, the sequence of the template nucleic acid can be determined. The signals from the CMOS detector are sent to a computer system for analyzing the data including making the best base calls based on the information available.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. An analytical device comprising:
a substrate;
an integrated illumination element;
a plurality of illumination volumes; and
a plurality of detector elements; wherein
the integrated illumination element is disposed in the substrate;
the integrated illumination element comprises an optical resonator within a waveguide;
the optical resonator comprises a laser medium and a first and a second mirror disposed within the waveguide; and
the plurality of illumination volumes are contained in a plurality of nanowells disposed on a surface of the substrate, wherein at least a first nanowell is optically coupled to the waveguide and to one of the detector elements.

2. The analytical device of claim 1, wherein the at least a first nanowell is optically coupled to the waveguide by evanescent illumination emanating from the waveguide.

3. The analytical device of claim 2, wherein the first mirror and the second mirror are 100% reflection mirrors, and wherein the at least a first nanowell is optically coupled to the waveguide at a region directly adjacent to the optical resonator.

4. The analytical device of claim 3, wherein no more than one nanowell or no more than one row of nanowells is coupled to the waveguide.

5. The analytical device of claim 2, wherein the first mirror is a high reflector mirror and the second mirror is a partial reflector mirror.

6. The analytical device of claim 2, wherein the optical resonator amplifies optical energy in the waveguide.

7. The analytical device of claim 2, wherein the at least a first nanowell is optically coupled to the waveguide at a region remote from the optical resonator.

8. The analytical device of claim 7, wherein no more than one nanowell or no more than one row of nanowells is coupled to the waveguide.

9. The analytical device of claim 2, further comprising a second nanowell optically coupled to the waveguide by evanescent illumination emanating from the waveguide, wherein the at least a first nanowell is optically coupled to the waveguide at a region directly adjacent to the optical resonator and the second nanowell is optically coupled to the waveguide at a region remote from the optical resonator.

10. The analytical device of claim 9, wherein no more than one nanowell or no more than one row of nanowells is coupled to the waveguide.

11. The analytical device of claim 1, wherein the integrated illumination element comprises a plurality of optical resonators within a waveguide, each optical resonator comprising a laser medium and a first and a second mirror disposed within the waveguide; and wherein the at least a first nanowell is optically coupled to the integrated illumination element.

12. The analytical device of claim 11, wherein at least one of the optical resonators amplifies optical energy in the waveguide.

13. The analytical device of claim 12, wherein the at least a first nanowell is optically coupled to the waveguide at a region remote from the optical resonators.

14. The analytical device of claim 1, wherein at least one optical resonator is optically pumped.

15. The analytical device of claim 1, wherein at least one optical resonator is electrically pumped.

16. The analytical device of claim 1, further comprising an analyte disposed within at least one illumination volume.

17. The analytical device of claim 16, wherein the analyte comprises a biological sample.

18. The analytical device of claim 17, wherein the biological sample comprises a nucleic acid.

19. The analytical device of claim 17, wherein the biological sample comprises a polymerase enzyme.

20. The analytical device of claim 1, wherein the analytical device comprises at least 1,000, at least 10,000, at least 100,000, at least 1,000,000, or at least 10,000,000 illumination volumes.

21. The analytical device of claim 1, wherein at least one detector element of the plurality of detector elements further comprises a spectral diversion element.

22. The analytical device of claim 1, wherein at least one detector element of the plurality of detector elements further comprises a light redirection cone.

* * * * *